US011278356B2

(12) United States Patent
Fahey et al.

(10) Patent No.: US 11,278,356 B2
(45) Date of Patent: Mar. 22, 2022

(54) SYSTEMS AND METHODS FOR LOCATING BLOOD VESSELS IN THE TREATMENT OF RHINITIS

(71) Applicant: Arrinex, Inc., Redwood City, CA (US)

(72) Inventors: Brian Fahey, Menlo Park, CA (US); William Jason Fox, San Mateo, CA (US); Bryant Lin, Menlo Park, CA (US); Mojgan Saadat, Atherton, CA (US); Vahid Saadat, Atherton, CA (US)

(73) Assignee: Arrinex, Inc., Redwood City, CA (US)

( * ) Notice: Subject to any disclaimer, the term of this patent is extended or adjusted under 35 U.S.C. 154(b) by 693 days.

(21) Appl. No.: 15/967,498

(22) Filed: Apr. 30, 2018

(65) Prior Publication Data
US 2018/0344411 A1 Dec. 6, 2018

Related U.S. Application Data

(60) Provisional application No. 62/492,074, filed on Apr. 28, 2017.

(51) Int. Cl.
*A61B 34/20* (2016.01)
*A61B 8/08* (2006.01)
(Continued)

(52) U.S. Cl.
CPC .............. *A61B 34/20* (2016.02); *A61B 8/06* (2013.01); *A61B 8/085* (2013.01); *A61B 8/12* (2013.01);
(Continued)

(58) Field of Classification Search
CPC .......... A61B 34/20; A61B 8/06; A61B 8/085; A61B 18/02; A61B 18/06; A61B 18/1492;
(Continued)

(56) References Cited

U.S. PATENT DOCUMENTS

| 4,582,067 A | 4/1986 | Silverstein et al. |
| 4,887,605 A | 12/1989 | Angelsen et al. |

(Continued)

FOREIGN PATENT DOCUMENTS

| CN | 102008283 | 5/2012 |
| CN | 103385736 | 7/2015 |

(Continued)

OTHER PUBLICATIONS

Anggard, "The Effects of Parasympathetic Nerve Stimulation on the Microcirculation and Secretion in the Nasal Musosa of the Cat", Acta Oto-Laryngologica, vol. 78, Nos. 1-6, Jul. 8, 2009, pp. 98-105.

(Continued)

*Primary Examiner* — Amanda Lauritzen Moher
*Assistant Examiner* — Amy J Shafqat
(74) *Attorney, Agent, or Firm* — McDonnell Boehnen Hulbert & Berghoff LLP

(57) ABSTRACT

Apparatus and methods for treating and monitoring conditions such as rhinitis are disclosed herein. The technology utilizes ultrasound scans to identify target treatment sites, and monitor the treatment of a patient undergoing a treatment. The treatment may be an ablation treatment of a nasal nerve, for example the PNN for the treatment of nasal conditions, such as rhinitis. The ultrasound scans are performed within the nasal cavity with an ultrasound probe or a combined ultrasound and ablation probe and may use Doppler, A-mode, B-mode, M-mode or other ultrasound and non-ultrasound modalities to detect and monitor the target treatment sites.

26 Claims, 31 Drawing Sheets

(51) Int. Cl.
| | |
|---|---|
| *A61B 18/02* | (2006.01) |
| *A61B 18/06* | (2006.01) |
| *A61B 18/14* | (2006.01) |
| *A61B 34/00* | (2016.01) |
| *A61B 8/12* | (2006.01) |
| *A61B 8/06* | (2006.01) |
| *A61B 90/00* | (2016.01) |
| *A61B 8/00* | (2006.01) |
| *A61B 18/00* | (2006.01) |
| *A61B 17/00* | (2006.01) |
| *A61B 18/08* | (2006.01) |

(52) U.S. Cl.
CPC .............. *A61B 18/02* (2013.01); *A61B 18/06* (2013.01); *A61B 18/1492* (2013.01); *A61B 34/76* (2016.02); *A61B 8/0858* (2013.01); *A61B 8/4466* (2013.01); *A61B 8/4477* (2013.01); *A61B 8/463* (2013.01); *A61B 18/082* (2013.01); *A61B 2017/00026* (2013.01); *A61B 2017/00084* (2013.01); *A61B 2017/00106* (2013.01); *A61B 2018/0022* (2013.01); *A61B 2018/0088* (2013.01); *A61B 2018/00303* (2013.01); *A61B 2018/00327* (2013.01); *A61B 2018/00577* (2013.01); *A61B 2018/00642* (2013.01); *A61B 2018/00904* (2013.01); *A61B 2018/0212* (2013.01); *A61B 2018/0262* (2013.01); *A61B 2034/2051* (2016.02); *A61B 2034/2063* (2016.02); *A61B 2090/061* (2016.02); *A61B 2090/064* (2016.02); *A61B 2090/3784* (2016.02)

(58) Field of Classification Search
CPC ..... A61B 34/76; A61B 8/12; A61B 2090/061; A61B 2017/00084; A61B 2018/00303; A61B 2090/064; A61B 8/463; A61B 2034/2051; A61B 2017/00026; A61B 2018/0088; A61B 2018/0262; A61B 2090/3784; A61B 8/0858; A61B 8/4466; A61B 8/4477; A61B 18/082; A61B 2018/00327; A61B 2018/00577; A61B 2018/0212; A61B 2034/2063; A61B 2018/0022; A61B 2017/00106; A61B 2018/00642; A61B 2018/00904; A61B 2018/00875

See application file for complete search history.

(56) References Cited

U.S. PATENT DOCUMENTS

| | | |
|---|---|---|
| 5,348,008 A | 9/1994 | Bornn et al. |
| 5,527,351 A | 6/1996 | Friedman |
| 5,533,499 A | 7/1996 | Johnson |
| 5,542,916 A | 8/1996 | Hirsch et al. |
| 5,570,692 A | 11/1996 | Morinaga |
| 5,611,796 A | 3/1997 | Kamami |
| 5,624,439 A | 4/1997 | Edwards et al. |
| 5,674,191 A | 10/1997 | Edwards et al. |
| 5,707,349 A | 1/1998 | Edwards |
| 5,718,702 A | 2/1998 | Edwards |
| 5,728,094 A | 3/1998 | Edwards |
| 5,730,719 A | 3/1998 | Edwards |
| 5,733,280 A | 3/1998 | Avitall |
| 5,738,114 A | 4/1998 | Edwards |
| 5,743,870 A | 4/1998 | Edwards |
| 5,743,904 A | 4/1998 | Edwards |
| 5,746,224 A | 5/1998 | Edwards |
| 5,800,429 A | 9/1998 | Edwards |
| 5,807,306 A | 9/1998 | Shapland et al. |
| 5,816,095 A | 10/1998 | Nordell, II et al. |
| 5,817,049 A | 10/1998 | Edwards |
| 5,820,580 A | 10/1998 | Edwards et al. |
| 5,823,197 A | 10/1998 | Edwards |
| 5,827,277 A | 10/1998 | Edwards |
| 5,843,021 A | 12/1998 | Edwards et al. |
| 5,843,077 A | 12/1998 | Edwards |
| 5,846,235 A | 12/1998 | Pasricha et al. |
| 5,879,349 A | 3/1999 | Edwards |
| 5,899,898 A | 5/1999 | Arless et al. |
| 5,899,899 A | 5/1999 | Arless et al. |
| 5,938,659 A | 8/1999 | Tu et al. |
| 5,971,979 A | 10/1999 | Joye et al. |
| 6,045,549 A | 4/2000 | Smethers et al. |
| 6,096,033 A | 8/2000 | Tu et al. |
| 6,102,907 A | 8/2000 | Smethers et al. |
| 6,106,518 A | 8/2000 | Wittenberger et al. |
| 6,109,268 A | 8/2000 | Thapliyal et al. |
| 6,126,657 A | 10/2000 | Edwards et al. |
| 6,131,579 A | 10/2000 | Thorson et al. |
| 6,139,546 A | 10/2000 | Koenig et al. |
| 6,152,143 A | 11/2000 | Edwards |
| 6,165,173 A | 12/2000 | Kamdar et al. |
| 6,179,803 B1 | 1/2001 | Edwards et al. |
| 6,210,355 B1 | 4/2001 | Edwards et al. |
| 6,217,519 B1 | 4/2001 | Grund et al. |
| 6,228,079 B1 | 5/2001 | Koenig |
| 6,231,569 B1 | 5/2001 | Bek et al. |
| 6,270,476 B1 | 8/2001 | Santoianni et al. |
| 6,283,959 B1 | 9/2001 | Lalonde et al. |
| 6,293,941 B1 | 9/2001 | Strul et al. |
| 6,309,386 B1 | 10/2001 | Bek |
| 6,355,029 B1 | 3/2002 | Joye et al. |
| 6,361,531 B1 | 3/2002 | Hissong |
| 6,371,926 B1 | 4/2002 | Thorson et al. |
| 6,375,654 B1 | 4/2002 | McIntyre |
| 6,383,181 B1 | 5/2002 | Johnston et al. |
| 6,391,028 B1 | 5/2002 | Fanton et al. |
| 6,416,491 B1 | 7/2002 | Edwards et al. |
| 6,425,151 B2 | 7/2002 | Barnett |
| 6,428,534 B1 | 8/2002 | Joye et al. |
| 6,431,174 B1 | 8/2002 | Knudson et al. |
| 6,432,102 B2 | 8/2002 | Joye et al. |
| 6,451,013 B1 | 9/2002 | Bays et al. |
| 6,502,574 B2 | 1/2003 | Stevens et al. |
| 6,506,157 B1 | 1/2003 | Teigman et al. |
| 6,514,245 B1 | 2/2003 | Williams et al. |
| 6,517,533 B1 | 2/2003 | Swaminathan |
| 6,537,271 B1 | 3/2003 | Murray et al. |
| 6,551,310 B1 | 4/2003 | Ganz et al. |
| 6,562,036 B1 | 5/2003 | Ellman et al. |
| 6,575,966 B2 | 6/2003 | Lane et al. |
| 6,575,969 B1 | 6/2003 | Rittman, III et al. |
| 6,589,235 B2 | 7/2003 | Wong et al. |
| 6,595,988 B2 | 7/2003 | Wittenberger et al. |
| 6,602,276 B2 | 8/2003 | Dobak, III et al. |
| 6,648,879 B2 | 11/2003 | Joye et al. |
| 6,659,106 B1 | 12/2003 | Hovda et al. |
| 6,666,858 B2 | 12/2003 | Lafontaine |
| 6,673,066 B2 | 1/2004 | Werneth |
| 6,685,732 B2 | 2/2004 | Kramer |
| 6,736,809 B2 | 5/2004 | Capuano et al. |
| 6,786,900 B2 | 9/2004 | Joye et al. |
| 6,786,901 B2 | 9/2004 | Joye et al. |
| 6,805,130 B2 | 10/2004 | Tasto et al. |
| 6,811,550 B2 | 11/2004 | Holland et al. |
| 6,875,209 B2 | 4/2005 | Zvuloni et al. |
| 6,905,494 B2 | 6/2005 | Yon et al. |
| 6,908,462 B2 | 6/2005 | Joye et al. |
| 6,911,027 B1 | 6/2005 | Edwards et al. |
| 6,949,096 B2 | 9/2005 | Davison et al. |
| 6,972,015 B2 | 12/2005 | Joye et al. |
| 6,978,781 B1 | 12/2005 | Jordan |
| 6,989,009 B2 | 1/2006 | Lafontaine |
| 6,991,631 B2 | 1/2006 | Woloszko et al. |
| 7,001,378 B2 | 2/2006 | Yon et al. |
| 7,055,523 B1 | 6/2006 | Brown |
| 7,060,062 B2 | 6/2006 | Joye et al. |
| 7,081,112 B2 | 7/2006 | Joye et al. |
| 7,101,368 B2 | 9/2006 | Lafontaine |

(56) References Cited

U.S. PATENT DOCUMENTS

| | | |
|---|---|---|
| 7,104,984 B2 | 9/2006 | Ryba |
| 7,114,495 B2 | 10/2006 | Lockwood, Jr. |
| 7,189,227 B2 | 3/2007 | Lafontaine |
| 7,288,089 B2 | 10/2007 | Yon et al. |
| 7,291,144 B2 | 11/2007 | Dobak, III et al. |
| 7,300,433 B2 | 11/2007 | Lane et al. |
| 7,322,993 B2 | 1/2008 | Metzger et al. |
| 7,354,434 B2 | 4/2008 | Zvuloni et al. |
| 7,416,550 B2 | 8/2008 | Protsenko et al. |
| 7,418,292 B2 | 8/2008 | Shafer |
| 7,442,190 B2 | 10/2008 | Abboud et al. |
| 7,442,191 B2 | 10/2008 | Hovda et al. |
| 7,449,018 B2 | 11/2008 | Kramer |
| 7,488,292 B2 | 2/2009 | Adachi |
| 7,527,622 B2 | 5/2009 | Lane et al. |
| 7,641,679 B2 | 1/2010 | Joye et al. |
| 7,648,497 B2 | 1/2010 | Lane et al. |
| 7,678,069 B1 | 3/2010 | Baker et al. |
| 7,727,191 B2 | 6/2010 | Mihalik et al. |
| 7,727,228 B2 | 6/2010 | Abboud et al. |
| 7,740,627 B2 | 6/2010 | Gammie et al. |
| 7,769,442 B2 | 8/2010 | Shafer |
| 7,780,730 B2 | 8/2010 | Saidi |
| 7,794,455 B2 | 9/2010 | Abboud et al. |
| 7,824,394 B2 | 11/2010 | Manstein |
| 7,842,031 B2 | 11/2010 | Abboud et al. |
| 7,850,683 B2 | 12/2010 | Elkins et al. |
| 7,862,557 B2 | 1/2011 | Joye et al. |
| 7,892,230 B2 | 2/2011 | Woloszko |
| 8,043,283 B2 | 10/2011 | Dobak, III et al. |
| 8,043,351 B2 | 10/2011 | Yon et al. |
| 8,088,127 B2 | 1/2012 | Mayse et al. |
| 8,137,345 B2 | 3/2012 | McNall, III et al. |
| 8,142,424 B2 | 3/2012 | Swanson |
| 8,157,794 B2 | 4/2012 | Dobak, III et al. |
| 8,177,779 B2 | 5/2012 | Joye et al. |
| 8,187,261 B2 | 5/2012 | Watson |
| 8,206,304 B1 | 6/2012 | Suchdev et al. |
| 8,231,613 B2 | 7/2012 | Baxter et al. |
| 8,235,976 B2 | 8/2012 | Lafontaine |
| 8,292,887 B2 | 10/2012 | Woloszko et al. |
| 8,298,217 B2 | 10/2012 | Lane et al. |
| 8,317,781 B2 | 11/2012 | Owens et al. |
| 8,317,782 B1 | 11/2012 | Ellman et al. |
| 8,333,758 B2 | 12/2012 | Joye et al. |
| 8,382,746 B2 | 2/2013 | Williams et al. |
| 8,382,747 B2 | 2/2013 | Abboud et al. |
| 8,388,600 B1 | 3/2013 | Eldredge |
| 8,394,075 B2 | 3/2013 | Ansarinia |
| 8,425,456 B2 | 4/2013 | Mihalik et al. |
| 8,425,457 B2 | 4/2013 | John et al. |
| 8,439,906 B2 | 5/2013 | Watson |
| 8,465,481 B2 | 6/2013 | Mazzone et al. |
| 8,475,440 B2 | 7/2013 | Abboud et al. |
| 8,480,664 B2 | 7/2013 | Watson et al. |
| 8,491,636 B2 | 7/2013 | Abboud et al. |
| 8,512,324 B2 | 8/2013 | Abboud et al. |
| 8,545,491 B2 | 10/2013 | Abboud et al. |
| 8,591,504 B2 | 11/2013 | Tin |
| 8,617,149 B2 | 12/2013 | Lafontaine et al. |
| 8,632,529 B2 | 1/2014 | Bencini |
| 8,663,211 B2 | 3/2014 | Fourkas et al. |
| 8,672,930 B2 | 3/2014 | Wittenberger |
| 8,676,324 B2 | 3/2014 | Simon et al. |
| 8,679,104 B2 | 3/2014 | Abboud et al. |
| 8,679,105 B2 | 3/2014 | Wittenberger et al. |
| 8,715,274 B2 | 5/2014 | Watson |
| 8,715,275 B2 | 5/2014 | Burger et al. |
| 8,747,401 B2 | 6/2014 | Gonzalez et al. |
| 8,764,740 B2 | 7/2014 | Watson |
| 8,771,264 B2 | 7/2014 | Abboud et al. |
| 8,827,952 B2 | 9/2014 | Subramaniam et al. |
| 8,840,608 B2 | 9/2014 | Anderson et al. |
| 8,900,222 B2 | 12/2014 | Abboud et al. |
| 8,911,434 B2 | 12/2014 | Wittenberger |
| 8,926,602 B2 | 1/2015 | Pageard |
| 8,936,594 B2 | 1/2015 | Wolf et al. |
| 8,945,107 B2 | 2/2015 | Buckley et al. |
| 8,986,293 B2 | 3/2015 | Desrochers |
| 8,986,301 B2 | 3/2015 | Wolf et al. |
| 8,996,137 B2 | 3/2015 | Ackermann et al. |
| 9,050,073 B2 | 6/2015 | Newell et al. |
| 9,050,074 B2 | 6/2015 | Joye et al. |
| 9,060,754 B2 | 6/2015 | Buckley et al. |
| 9,060,755 B2 | 6/2015 | Buckley et al. |
| 9,066,713 B2 | 6/2015 | Turovskiy |
| 9,072,597 B2 | 7/2015 | Wolf et al. |
| 9,084,590 B2 | 7/2015 | Wittenberger et al. |
| 9,084,592 B2 | 7/2015 | Wu et al. |
| 9,089,314 B2 | 7/2015 | Wittenberger |
| 9,101,346 B2 | 8/2015 | Burger et al. |
| 9,125,677 B2 | 9/2015 | Sobol et al. |
| 9,168,079 B2 | 10/2015 | Lalonde |
| 9,168,081 B2 | 10/2015 | Williams et al. |
| 9,179,964 B2 | 11/2015 | Wolf et al. |
| 9,179,967 B2 | 11/2015 | Wolf et al. |
| 9,211,393 B2 | 12/2015 | Hu et al. |
| 9,220,556 B2 | 12/2015 | Lalonde et al. |
| 9,237,924 B2 | 1/2016 | Wolf et al. |
| 9,241,752 B2 | 1/2016 | Nash et al. |
| 9,254,166 B2 | 2/2016 | Aluru et al. |
| 9,265,956 B2 | 2/2016 | Ackermann et al. |
| 9,333,023 B2 | 5/2016 | Wittenberger |
| 9,414,878 B1 | 8/2016 | Wu et al. |
| 9,415,194 B2 | 8/2016 | Wolf et al. |
| 9,433,463 B2 | 9/2016 | Wolf et al. |
| 9,439,709 B2 | 9/2016 | Duong et al. |
| 9,445,859 B2 | 9/2016 | Pageard |
| 9,452,010 B2 | 9/2016 | Wolf et al. |
| 9,452,087 B2 | 9/2016 | Holm et al. |
| 9,474,915 B2 | 10/2016 | Gonzales et al. |
| 9,480,521 B2 | 11/2016 | Kim et al. |
| 9,486,278 B2 | 11/2016 | Wolf et al. |
| 9,522,030 B2 | 12/2016 | Harmouche et al. |
| 9,526,571 B2 | 12/2016 | Wolf et al. |
| 9,555,223 B2 | 1/2017 | Abboud et al. |
| 9,572,536 B2 | 2/2017 | Abboud et al. |
| 9,687,288 B2 | 6/2017 | Saadat |
| 9,687,296 B2 | 6/2017 | Wolf et al. |
| 9,700,707 B2 | 7/2017 | Deem et al. |
| 9,724,119 B2 | 8/2017 | Hissong et al. |
| 9,763,723 B2 | 9/2017 | Saadat |
| 9,788,886 B2 | 10/2017 | Wolf et al. |
| 9,801,752 B2 | 10/2017 | Wolf et al. |
| 9,888,957 B2 | 2/2018 | Wolf et al. |
| 9,913,682 B2 | 3/2018 | Wolf et al. |
| 9,943,361 B2 | 4/2018 | Wolf et al. |
| 10,028,781 B2 | 7/2018 | Saadat |
| 2002/0016588 A1 | 2/2002 | Wong et al. |
| 2002/0049464 A1 | 4/2002 | Donofrio et al. |
| 2002/0128641 A1 | 9/2002 | Underwood et al. |
| 2003/0114843 A1 | 6/2003 | Lafontaine |
| 2003/0144659 A1 | 7/2003 | Edwards |
| 2003/0208194 A1 | 11/2003 | Hovda et al. |
| 2003/0225403 A1 | 12/2003 | Woloszko et al. |
| 2004/0024412 A1 | 2/2004 | Clements et al. |
| 2004/0220644 A1 | 11/2004 | Shalev et al. |
| 2005/0020901 A1 | 1/2005 | Belson et al. |
| 2005/0119643 A1 | 6/2005 | Sobol et al. |
| 2005/0222565 A1 | 10/2005 | Manstein |
| 2005/0234439 A1 | 10/2005 | Underwood |
| 2006/0195169 A1* | 8/2006 | Gross .................. A61N 1/0546 607/116 |
| 2006/0235377 A1 | 10/2006 | Earley et al. |
| 2006/0235474 A1 | 10/2006 | Demarais |
| 2006/0253117 A1 | 11/2006 | Hovda et al. |
| 2006/0276817 A1 | 12/2006 | Vassallo et al. |
| 2006/0276852 A1 | 12/2006 | Demarais et al. |
| 2007/0066944 A1 | 3/2007 | Nyte |
| 2007/0073282 A1 | 3/2007 | McGaffigan et al. |
| 2007/0173899 A1 | 7/2007 | Levin et al. |
| 2007/0219600 A1 | 9/2007 | Gertner et al. |
| 2007/0265687 A1 | 11/2007 | Deem et al. |
| 2007/0299433 A1 | 12/2007 | Williams et al. |

(56) References Cited

U.S. PATENT DOCUMENTS

| | | |
|---|---|---|
| 2008/0009851 A1 | 1/2008 | Wittenberger et al. |
| 2008/0009925 A1 | 1/2008 | Abboud et al. |
| 2008/0027423 A1 | 1/2008 | Choi et al. |
| 2008/0027480 A1 | 1/2008 | van der Burg et al. |
| 2008/0082090 A1 | 4/2008 | Manstein |
| 2008/0119693 A1 | 5/2008 | Makower et al. |
| 2009/0018485 A1 | 1/2009 | Krespi et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0143821 A1 | 6/2009 | Stupak |
| 2009/0182318 A1 | 7/2009 | Abboud et al. |
| 2009/0234345 A1 | 9/2009 | Hon |
| 2009/0292358 A1 | 11/2009 | Said |
| 2009/0318804 A1 | 12/2009 | Avital et al. |
| 2010/0057150 A1 | 3/2010 | Demarais et al. |
| 2010/0063398 A1 | 3/2010 | Halmann et al. |
| 2010/0137860 A1 | 6/2010 | Demarais et al. |
| 2010/0137952 A1 | 6/2010 | Demarais et al. |
| 2010/0144996 A1 | 6/2010 | Kennedy et al. |
| 2010/0152730 A1 | 6/2010 | Makower et al. |
| 2010/0168569 A1 | 7/2010 | Silwa et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0174283 A1 | 7/2010 | McNall, III et al. |
| 2010/0191112 A1 | 7/2010 | Demarais et al. |
| 2011/0009737 A1 | 1/2011 | Manstein |
| 2011/0125026 A1 | 5/2011 | Neto |
| 2011/0152855 A1 | 6/2011 | Mayse et al. |
| 2011/0184402 A1 | 7/2011 | Baust et al. |
| 2011/0245671 A1* | 10/2011 | Sato .............. A61B 8/0808 600/443 |
| 2011/0282268 A1 | 11/2011 | Baker et al. |
| 2012/0029493 A1 | 2/2012 | Wittenberger et al. |
| 2012/0039954 A1 | 2/2012 | Cupit et al. |
| 2012/0078377 A1 | 3/2012 | Gonzales et al. |
| 2012/0143130 A1 | 6/2012 | Subramaniam et al. |
| 2012/0197245 A1 | 8/2012 | Burnett et al. |
| 2012/0298105 A1 | 11/2012 | Osorio |
| 2012/0316473 A1 | 12/2012 | Bonutti et al. |
| 2012/0316557 A1 | 12/2012 | Sartor et al. |
| 2012/0323227 A1 | 12/2012 | Wolf et al. |
| 2012/0323232 A1 | 12/2012 | Wolf et al. |
| 2013/0006326 A1 | 1/2013 | Ackermann et al. |
| 2013/0018366 A1 | 1/2013 | Wu et al. |
| 2013/0218151 A1 | 8/2013 | Mihalik et al. |
| 2013/0218158 A1 | 8/2013 | Danek et al. |
| 2013/0253387 A1 | 9/2013 | Bonutti et al. |
| 2013/0310822 A1 | 11/2013 | Mayse et al. |
| 2013/0324989 A1 | 12/2013 | Leung et al. |
| 2013/0345700 A1 | 12/2013 | Hlavka et al. |
| 2014/0031726 A1 | 1/2014 | Chernomorsky et al. |
| 2014/0058369 A1 | 2/2014 | Hon |
| 2014/0088463 A1 | 3/2014 | Wolf et al. |
| 2014/0114233 A1 | 4/2014 | Deem et al. |
| 2014/0186341 A1 | 7/2014 | Mayse |
| 2014/0207130 A1 | 7/2014 | Fourkas et al. |
| 2014/0236148 A1 | 8/2014 | Hlavka et al. |
| 2014/0257271 A1 | 9/2014 | Mayse et al. |
| 2014/0276783 A1 | 9/2014 | Srivastava |
| 2014/0276792 A1 | 9/2014 | Kaveckis et al. |
| 2014/0277429 A1 | 9/2014 | Kuzma et al. |
| 2014/0316310 A1 | 10/2014 | Ackermann et al. |
| 2014/0316396 A1 | 10/2014 | Wolf et al. |
| 2014/0371812 A1 | 12/2014 | Ackermann et al. |
| 2014/0378873 A1 | 12/2014 | Chernomorsky et al. |
| 2015/0011843 A1 | 1/2015 | Toth et al. |
| 2015/0031946 A1 | 1/2015 | Saadat et al. |
| 2015/0045781 A1 | 2/2015 | Abboud et al. |
| 2015/0073395 A1 | 3/2015 | Wolf et al. |
| 2015/0080870 A1 | 3/2015 | Wittenberger |
| 2015/0087975 A1 | 3/2015 | Salcudean et al. |
| 2015/0119868 A1 | 4/2015 | Lalonde et al. |
| 2015/0126986 A1 | 5/2015 | Kelly et al. |
| 2015/0141987 A1* | 5/2015 | Caplan .............. A61B 18/14 606/41 |
| 2015/0157382 A1 | 6/2015 | Avitall et al. |
| 2015/0157395 A1 | 6/2015 | Wolf et al. |
| 2015/0164401 A1 | 6/2015 | Toth et al. |
| 2015/0164571 A1 | 6/2015 | Saadat |
| 2015/0190188 A1 | 7/2015 | Lalonde |
| 2015/0196345 A1 | 7/2015 | Newell et al. |
| 2015/0196740 A1 | 7/2015 | Mallin et al. |
| 2015/0202003 A1 | 7/2015 | Wolf et al. |
| 2015/0223860 A1 | 8/2015 | Wittenberger et al. |
| 2015/0238754 A1 | 8/2015 | Loudin et al. |
| 2015/0250524 A1 | 9/2015 | Moriarty et al. |
| 2015/0265329 A1 | 9/2015 | Lalonde et al. |
| 2015/0265812 A1 | 9/2015 | Lalonde |
| 2015/0272663 A1 | 10/2015 | Wolf et al. |
| 2015/0297285 A1 | 10/2015 | Wolf et al. |
| 2015/0313661 A1 | 11/2015 | Wu et al. |
| 2016/0015450 A1 | 1/2016 | Wolf et al. |
| 2016/0022992 A1 | 1/2016 | Franke et al. |
| 2016/0038212 A1 | 2/2016 | Ryba et al. |
| 2016/0045277 A1 | 2/2016 | Lin et al. |
| 2016/0066975 A1 | 3/2016 | Fourkas et al. |
| 2016/0074090 A1 | 3/2016 | Lalonde et al. |
| 2016/0089200 A1 | 3/2016 | Wolf et al. |
| 2016/0114163 A1 | 4/2016 | Franke et al. |
| 2016/0114172 A1 | 4/2016 | Loudin et al. |
| 2016/0012118 A1 | 5/2016 | Sirer et al. |
| 2016/0143683 A1 | 5/2016 | Aluru et al. |
| 2016/0151646 A1 | 6/2016 | Bonutti et al. |
| 2016/0158548 A1 | 6/2016 | Ackermann et al. |
| 2016/0166305 A1 | 6/2016 | Nash et al. |
| 2016/0166306 A1 | 6/2016 | Pageard |
| 2016/0220295 A1 | 8/2016 | Wittenberger |
| 2016/0287315 A1 | 10/2016 | Wolf et al. |
| 2016/0310042 A1 | 10/2016 | Kesten et al. |
| 2016/0317794 A1 | 11/2016 | Saadat |
| 2016/0331433 A1 | 11/2016 | Wu et al. |
| 2016/0331459 A1 | 11/2016 | Townley et al. |
| 2016/0354134 A1 | 12/2016 | Pageard |
| 2016/0354135 A1 | 12/2016 | Saadat |
| 2016/0354136 A1 | 12/2016 | Saadat |
| 2016/0361112 A1 | 12/2016 | Wolf et al. |
| 2017/0007316 A1 | 1/2017 | Wolf et al. |
| 2017/0014258 A1 | 1/2017 | Wolf et al. |
| 2017/0042601 A1 | 2/2017 | Kim et al. |
| 2017/0056087 A1 | 3/2017 | Buckley et al. |
| 2017/0056632 A1 | 3/2017 | Jenkins et al. |
| 2017/0095288 A1 | 4/2017 | Wolf et al. |
| 2017/0209199 A1 | 7/2017 | Wolf et al. |
| 2017/0231651 A1 | 8/2017 | Dinger et al. |
| 2017/0245924 A1 | 8/2017 | Wolf et al. |
| 2017/0252089 A1 | 9/2017 | Hester et al. |
| 2017/0252100 A1 | 9/2017 | Wolf et al. |
| 2017/0360494 A1 | 12/2017 | Saadat |
| 2017/0360495 A1 | 12/2017 | Wolf et al. |
| 2018/0000535 A1 | 1/2018 | Wolf et al. |
| 2018/0008229 A1 | 1/2018 | Govari et al. |
| 2018/0133460 A1 | 5/2018 | Townley et al. |
| 2018/0177542 A1 | 6/2018 | Wolf et al. |
| 2018/0177546 A1 | 6/2018 | Dinger et al. |
| 2018/0185085 A1 | 7/2018 | Wolf et al. |

FOREIGN PATENT DOCUMENTS

| | | |
|---|---|---|
| DE | 102006052710 | 5/2008 |
| EP | 2532300 | 12/2012 |
| EP | 2662027 | 11/2013 |
| EP | 2662046 | 11/2013 |
| EP | 2662116 | 11/2013 |
| EP | 3017770 | 5/2016 |
| WO | 9920185 | 4/1999 |
| WO | 9927862 | 6/1999 |
| WO | 9930655 | 6/1999 |
| WO | 0009053 | 2/2000 |
| WO | 0047118 | 8/2000 |
| WO | 0054684 | 9/2000 |
| WO | 0143653 | 6/2001 |
| WO | 0164145 | 9/2001 |

(56) References Cited

FOREIGN PATENT DOCUMENTS

| | | |
|---|---|---|
| WO | 0195819 | 12/2001 |
| WO | 0204042 | 1/2002 |
| WO | 0207628 | 4/2002 |
| WO | 02069862 | 9/2002 |
| WO | 0200128 | 11/2002 |
| WO | 02083196 | 2/2003 |
| WO | 03013653 | 2/2003 |
| WO | 03026719 | 4/2003 |
| WO | 03051214 | 6/2003 |
| WO | 03028524 | 10/2003 |
| WO | 03020334 | 12/2003 |
| WO | 03088857 | 12/2003 |
| WO | 2004000092 | 12/2003 |
| WO | 2005089853 | 11/2005 |
| WO | 2004108207 | 12/2005 |
| WO | 2006002337 | 1/2006 |
| WO | 2006118725 | 11/2006 |
| WO | 2006119615 | 11/2006 |
| WO | 2006124176 | 11/2006 |
| WO | 2006017073 | 4/2007 |
| WO | 2007037895 | 4/2007 |
| WO | 2007134005 | 11/2007 |
| WO | 2007145759 | 12/2007 |
| WO | 2008000065 | 1/2008 |
| WO | 2008042890 | 4/2008 |
| WO | 2008046183 | 4/2008 |
| WO | 2008051918 | 5/2008 |
| WO | 2008157042 | 12/2008 |
| WO | 2009114701 | 9/2009 |
| WO | 2009146372 | 12/2009 |
| WO | 2010077980 | 7/2010 |
| WO | 2010081221 | 7/2010 |
| WO | 2010083281 | 7/2010 |
| WO | 2010111122 | 9/2010 |
| WO | 2011014812 | 2/2011 |
| WO | 2011091507 | 8/2011 |
| WO | 2011091508 | 8/2011 |
| WO | 2011091509 | 8/2011 |
| WO | 2011091533 | 8/2011 |
| WO | 2012012868 | 2/2012 |
| WO | 2012012869 | 2/2012 |
| WO | 2012015636 | 2/2012 |
| WO | 2012019156 | 2/2012 |
| WO | 2012051697 | 4/2012 |
| WO | 2012027641 | 5/2012 |
| WO | 2012058156 | 5/2012 |
| WO | 2012058159 | 5/2012 |
| WO | 2012058160 | 5/2012 |
| WO | 2012058161 | 5/2012 |
| WO | 2012058165 | 5/2012 |
| WO | 2012058167 | 5/2012 |
| WO | 2012174161 | 12/2012 |
| WO | 2013035192 | 3/2013 |
| WO | 2013110156 | 8/2013 |
| WO | 2013173481 | 11/2013 |
| WO | 2013163325 | 2/2014 |
| WO | 2014113864 | 7/2014 |
| WO | 2014138866 | 9/2014 |
| WO | 2014138867 | 9/2014 |
| WO | 2015038523 | 3/2015 |
| WO | 2015047863 | 4/2015 |
| WO | 2015048806 | 4/2015 |
| WO | 2015061883 | 5/2015 |
| WO | 2015081420 | 6/2015 |
| WO | 2015106335 | 7/2015 |
| WO | 2015114038 | 8/2015 |
| WO | 2015139117 | 9/2015 |
| WO | 2015139118 | 9/2015 |
| WO | 2015153696 | 10/2015 |
| WO | 2016183337 | 11/2016 |
| WO | 2016186964 | 11/2016 |
| WO | 2017034705 | 3/2017 |
| WO | 2017047543 | 3/2017 |
| WO | 2017047545 | 3/2017 |

OTHER PUBLICATIONS

Arora et al., "Cryodestruction of Vidian Nerve Branches", Indian Journal of Otolaryngology, vol. 32, Issue 3, Sep. 1980, pp. 80-82.
Bicknell, "CryoSurrgery for Allergic and Vasomotor Rhinitis", The Journal of Laryngology and Otology, vol. 93, Feb. 1979, pp. 143-146.
Bluestone et al., "Intranasal Freezing for Severe Epistaxis", Arch Otolaryng, vol. 85, Apr. 1967, pp. 119-121.
Buckley et al., "High-Resolution Spatial Mapping of Shear Properties in Cartilage", Journal of Biomechanics, vol. 43, No. 4, Mar. 3, 2010, pp. 796-800.
Buckley et al., "High-Resolution Spatial Mapping of Shear Properties in Cartilage", J Biomech., vol. 43, No. 4, Nov. 2009, pp. 796-800.
Buckley et al., "Mapping the Depth Dependence of Shear Properties in Articular Cartilage", Journal of Biomechanics, vol. 41, Issue 11, Aug. 7, 2008, pp. 2430-2437.
Buckley et al., "Mapping the Depth Dependence of Shear Properties in Articular Cartilage", Journal of Biomechanics, vol. 41, No. 11, Aug. 7, 2008, pp. 2430-2437.
Bumsted, "Cryotherapy for Chronic Vasomotor Rhinitis: Technique and Patient Selection for Improved Results", Laryngoscope, vol. 94, Issue 4, Aug. 1984, pp. 539-544.
Cole et al., "Biophysics of Nasal Airflow: A Review", American Journal of Rhinology & Allergy, vol. 14, No. 4, Jul. 1, 2000, pp. 245-249.
Cole, "Biophysics of Nasal Airflow: A Review", American Journal of Rhinology, vol. 14, No. 4, Jul.-Aug. 2000, pp. 245-249.
Cole, "The Four Components of the Nasal Valve", American Journal of Rhinology, vol. 17, No. 2, Mar.-Apr. 2003, pp. 107-110.
Cole et al., "The Four Components of the Nasal Valve", American Journal of Rhinology & Allergy, vol. 17, Issue 2, Mar.-Apr. 2003, pp. 107-110.
Costa et al., "Radiographic and Anatomic Characterization of the Nasal Septal Swell Body", Arch Otolaryngol Head Neck Surg., vol. 136, No. 11, Nov. 15, 2010, pp. 1107-1110.
Girdhar-Gopal et al., "An Assessment of Postganglionic Cryoneurolysis for Managing Vasomotor Rhinitis", American Journal of Rhinology, vol. 8, Issue 4, Jul.-Aug. 1994, pp. 157-164.
Golhar et al., "The effect of Cryodestruction of Vidian Nasal Branches on Nasal Mucus Flow in Vasomotor Rhinitis", Indian Journal of Otolaryngology, vol. 33, Issue 1, Mar. 1981, pp. 12-14.
Goode, "A Liquid Nitrogen Turbinate Probe for Hypertrophic Rhinitis", Arch Otolaryngol., vol. 103, No. 7, Jul. 1977, p. 431.
Griffin et al., "Effects of Enzymatic Treatments on the Depth-Dependent Viscoelastic Shear Properties of Articular Cartilage", Journal of Orthopaedic Research, vol. 32, Issue 12, Dec. 2014, pp. 1652-1657.
Griffin et al., "Effects of Enzymatic Treatments on the Depth-Dependent Viscoelastic Shear Properties of Articular Cartilage", Journal of Orthopaedic Research, vol. 32, No. 12, Dec. 2014, pp. 1652-1657.
Gurelik et al., "The Effects of the Electrical Stimulation of the Nasal Mucosa on Cortical Cerebral Blood Flow in Rabbits", Neuroscience Letters, vol. 365, Jan. 13, 2004, pp. 210-213.
Kjaergaard et al., "Relation of Nasal Air Flow to Nasal Cavity Dimensions", Arch Otolaryngol Head Neck Surg, vol. 135, No. 6, Jun. 2009, pp. 565-570.
Mehra et al., "Cryosurgery in Vasomotor Rhinitis-An Analysis of 156 Patients", Indian Journal of Otolaryngology, vol. 42, Issue 3, Sep. 1990, pp. 95-98.
Ozenberger, "Cryosurgery for the Treatment of Chronic Rhinitis", Laryngoscope, vol. 83, Issue 4, Apr. 1973, pp. 508-516.
Ozenberger, "Cryosurgery in Chronic Rhinitis", The Laryngoscope, vol. 80, Issue 5, May 1970, pp. 723-734.
Principato, "Chronic Vasomotor Rhinitis: Cryogenic and Other Surgical Modes of Treatment", The Laryngoscope, vol. 89, Issue 4, Apr. 1979, pp. 619-638.
Rao, "Cryosurgery on Inferior Turbinate Hypertrophy Under Topical Anaesthesia—Is it Boon in Electricity Deprived Places?", National Journal of Otorhinolaryngology and Head & Neck Surgery, vol. 10, No. 1, Apr. 2013, pp. 7-9.

(56) References Cited

OTHER PUBLICATIONS

Sanu et al., "Postnasal Drip Syndrome : Two Hundred Years of Controversy Between UK and USA", Rhinology, vol. 46, Apr. 6, 2008, pp. 86-91.
Schwartz , "Autonomix Neurophysiologic Sensing Technology", Autonomix Medical, Inc. Paper, Aug. 1, 2016, 4 pages.
Settipane et al., "Update on Nonallergic Rhinitis", Annals of Allergy, Asthma & Immunology, vol. 86, No. 5, May 2001, pp. 494-508.
Silverberg et al., "Structure-Function Relations and Rigidity Percolation in the Shear Properties of Articular Cartilage", Biophysical Journal, vol. 107, No. 7, Oct. 7, 2014, pp. 1721-1730.
Stewart et al., "Development and Validation of the Nasal Obstruction Symptom Evaluation (NOSE) Scale", Otolaryngology-Head and Neck Surgery, vol. 130, No. 2, Feb. 2004, pp. 157-163.
Strome , "A Long-term Assessment of Cryotherapy for Treating Vasomotor Instability", vol. 69, Issue 12, Dec. 1990, pp. 1-2.
Stupak , "A Perspective on the Nasal Valve", Dept. of Otorhinolaryngology, Nov. 6, 2009.
Stupak , "Endonasal Repositioning of the Upper Lateral Cartilage and the Internal Nasal Valve", Annals of Otology, Rhinology & Laryngology, vol. 120, No. 2, Feb. 2011, pp. 88-94.
Terao et al., "Cryosurgery on Postganglionic Fibers (Posterior Nasal Branches) of the Pterygopalatine Ganglion for Vasomotor Rhinitis", Acta Otolaryngol., vol. 96, Issue 1-2, Jul.-Aug. 1983, pp. 139-148.

\* cited by examiner

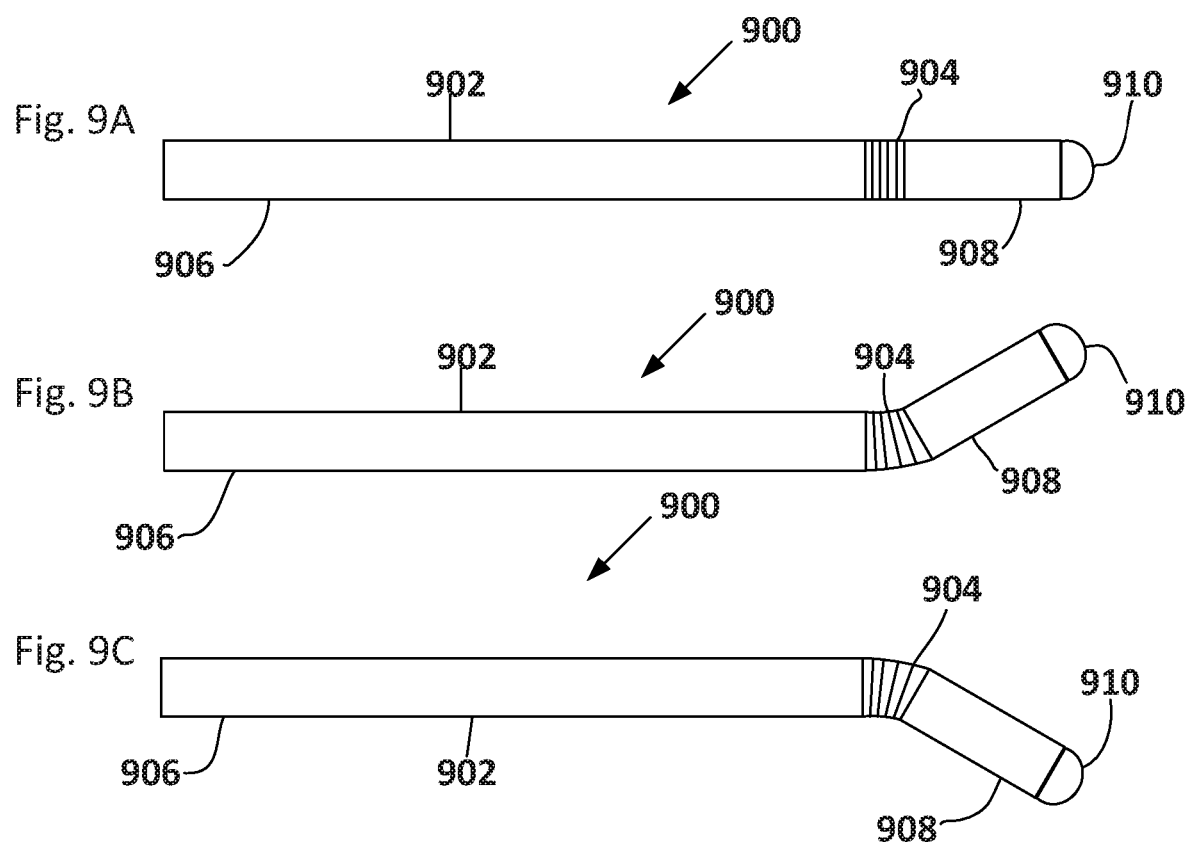
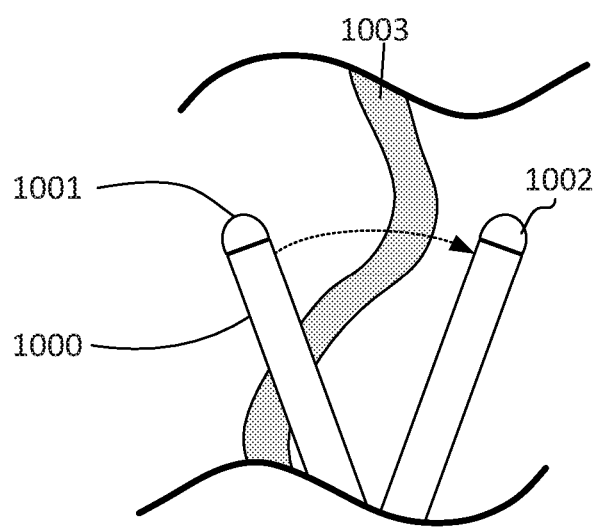
Fig. 10A
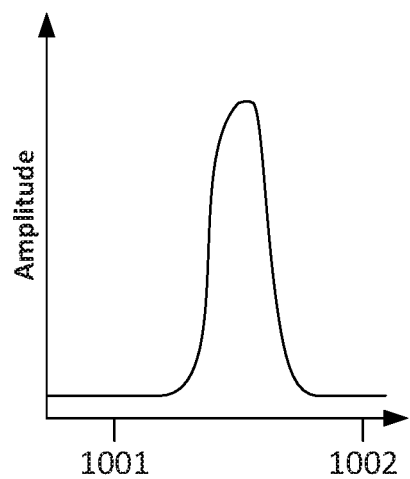
Fig. 10B

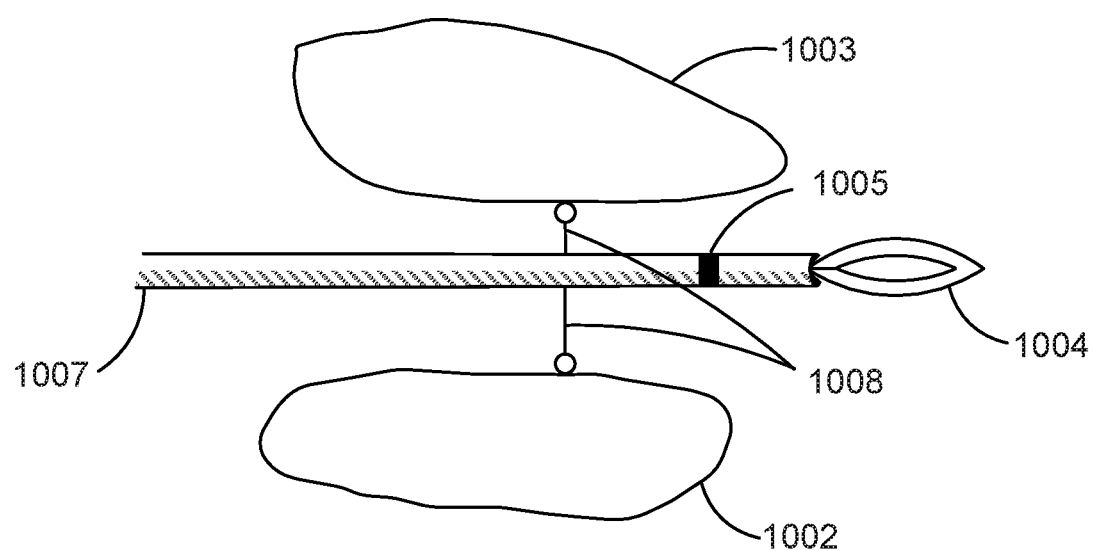
Fig. 32A
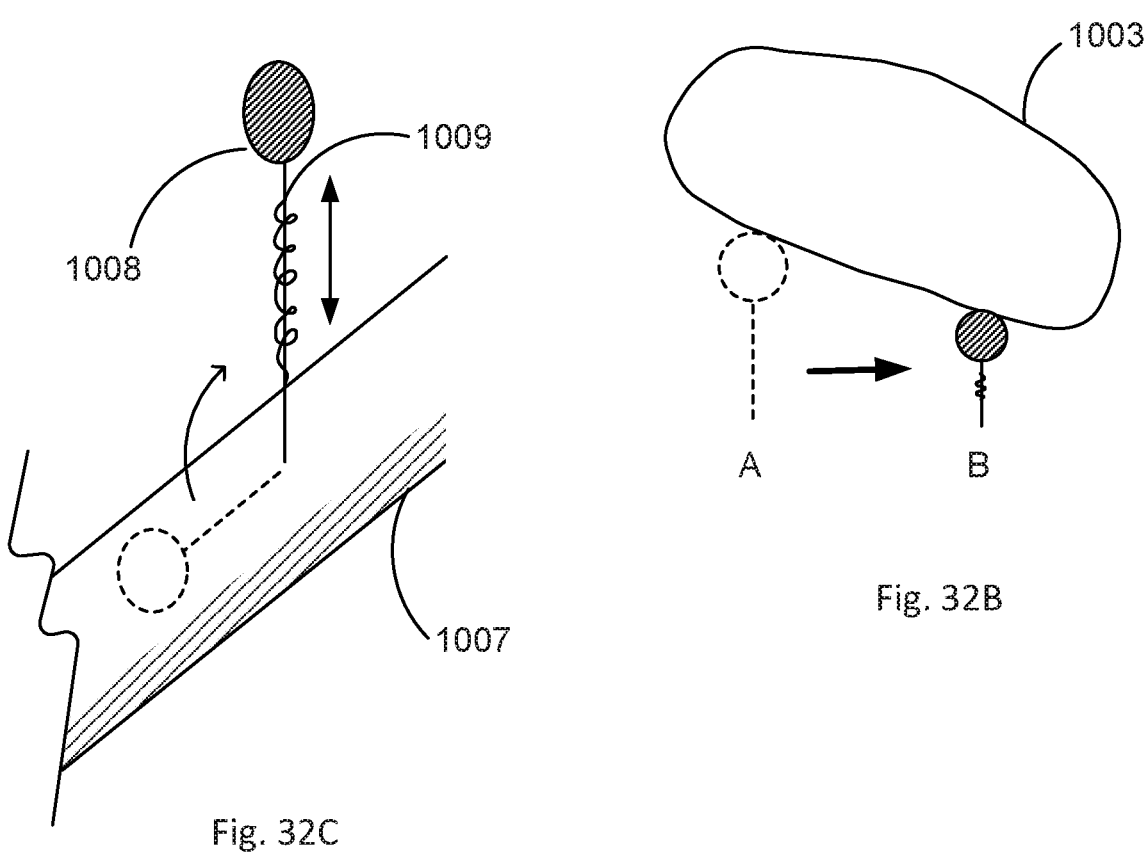
Fig. 32B
Fig. 32C

SYSTEMS AND METHODS FOR LOCATING BLOOD VESSELS IN THE TREATMENT OF RHINITIS

CROSS-REFERENCE TO RELATED APPLICATIONS

The present application claims the benefit of U.S. Provisional Application Ser. No. 62/492,074 filed Apr. 28, 2017, the entire contents of which are incorporated herein by reference in their entirety for all purposes. The present application is related to U.S. application Ser. No. 15/693,216, filed Aug. 31, 2017; U.S. application Ser. No. 15/786,306, filed Oct. 17, 2017; U.S. application Ser. No. 15/682,804, filed Aug. 22, 2017; U.S. application Ser. No. 15/431,740, filed Feb. 13, 2017 and U.S. application Ser. No. 15/624,632, filed Jun. 15, 2017 each of which is assigned to the same assignee as the present application and incorporated by reference herein in its entirety for all purposes.

FIELD OF THE INVENTION

The present invention is related to systems, devices and methods for identifying and monitoring treatment sites for ablating regions of tissue. More particularly, the present invention relates to locating treatment sites in the nasal cavity to ablate for treating nasal conditions, such as rhinitis, while inhibiting or reducing any collateral vessel damage (e.g., arterial bleeding).

BACKGROUND OF THE INVENTION

Rhinitis is defined as inflammation of the membranes lining the nose, characterized by nasal symptoms, including itching, sneezing, anterior nasal drainage (rhinorrhea), posterior nasal drainage (Post nasal drip), and/or nasal congestion. Chronic Rhinitis affects tens of millions of people in the US and is a leading cause for patients to seek medical care. Medical treatment has been shown to have limited effects for chronic rhinitis sufferers and requires daily medication use or onerous allergy treatments and up to 20% of patients may be refractory.

Selectively interrupting the Post Nasal Nerves (PNN) in patients with chronic rhinitis improves their symptoms while avoiding the morbidities associated with vidian neurectomy. Specifically, selective interruption of the PNN, interrupts the somatic afferent innervation to the nasal mucosa, and can reduce the hypersensitivity and axon reflexes of the nasal mucosa. While ablation of the PNN is a less invasive procedure with fewer complication and side effects than previous surgical methods for treating rhinitis, there can be complications if large blood vessels are damaged during the ablation.

As shown in FIGS. 1 and 2, the PNN generally follow the sphenopalatine artery (SPA). In some patient anatomies, the SPA may be co-located with the PNN. As such, during ablation of the PNN, unintentional collateral damage to the SPA may occur which may lead to excessive bleeding or other injury to the patient. In some cases, an excessive nose bleed may require subsequent surgical treatment or intervention to repair the damaged SPA. Thus, there is a need for improved systems, device, and methods that address some of these therapy challenges.

BRIEF SUMMARY

The present technology relates to systems, devices and methods for using ultrasound to identify target treatment sites, and monitor the treatment of a patient undergoing ablation treatment of a nasal nerve, for example the PNN for the treatment of nasal conditions, such as rhinitis. Such systems, devices, and methods provide for ablation of the PNN while inhibiting and/or reducing unintentional collateral vessel damage (e.g., bleeding of the SPA or a branch associated therewith). The present technology may also be used in the treatment of nasal valve collapse. The present technology may also be used in the treatment of post nasal drip and other related conditions, as disclosed in U.S. Pat. No. 9,801,752 which is incorporated by reference herein in its entirety for all purposes. The present technology may also be used with neuromodulation and other related treatments, as disclosed in U.S. published application 2016/0331459A1, which is incorporated by reference herein in its entirety for all purposes.

Embodiments include methods for treating rhinitis of a patient comprising advancing a surgical probe into a nasal cavity of a patient. The surgical probe may comprise an elongated probe shaft with a proximal end and a distal end, a handle coupled to the proximal end, an ultrasound transducer coupled to the probe shaft, and a cryo-ablation element coupled to the probe shaft. The method may further comprise determining a location of a target treatment site within the nasal cavity with the ultrasound transducer, positioning the cryo-ablation element at the target treatment site location; and cryogenically ablating the target treatment site in order to ablate at least one nasal nerve to reduce at least one symptom of rhinitis.

In embodiments the method may further comprise determining the location of the target treatment site comprises detecting relative thicknesses of mucosal tissue in the nasal cavity with the ultrasound transducer to identify an anatomical landmark correlated to the location of the target treatment site.

In embodiments the method may further comprise determining the location of the target treatment site by detecting relative thicknesses of a palatine or sphenoid bone in the nasal cavity with the ultrasound transducer to identify an anatomical landmark correlated to the location of the target treatment site.

In embodiments the method may further comprise determining the location of the target treatment site by detecting a relative boundary or transition between two bones in the nasal cavity or between a bone and cartilage in the nasal cavity with the ultrasound transducer to identify an anatomical landmark correlated to the location of the target treatment site. The transition may comprise 0.5-1 mm of cartilage adjacent to 1-3 mm of bone used to identify a perpendicular claims of a palatine bone.

In embodiments the method may further comprise using a surgical probe further comprising a second ultrasound transducer coupled to the probe shaft. The ultrasound transducer may be coupled to the probe shaft towards the distal end of the probe shaft and distal of the cryo-ablation element. The second ultrasound transducer may be coupled to the probe shaft towards the proximal end of the probe shaft and proximal the cryo-ablation element. Determining the location of the target treatment site may comprise detecting tissue properties with both the ultrasound transducer and the second ultrasound transducer.

In embodiments the method may further comprise detecting tissue properties with the ultrasound transducer and the second ultrasound transducer to determine the location of the target treatment site by identifying relative mucosal tissue thicknesses indicating that the cryo-ablation element is positioned proximate to the location of the target treatment site.

In embodiments the method may further comprise detecting tissue properties with the ultrasound transducer and the second ultrasound transducer to determine the location of the target treatment site by identifying relative bone thicknesses indicating that the cryo-ablation element is positioned proximate to the location of the target treatment site. The relative bone thickness may indicate that the ultrasound transducer is detecting a sphenoid bone and the second ultrasound transducer is detecting a palatine bone.

In embodiments the method may further comprise a surgical probe with the cryo-ablation element and the ultrasound transducer are coupled to the probe shaft at a predetermined distance relative to each other. The predetermined distance may correspond to a distance between an anatomical feature detectable with the ultrasound transducer and the at least one nasal nerve. Determining the location of the target treatment site may comprise locating the anatomical feature with the ultrasound transducer. Cryogenically ablating the target treatment site may comprise ablating the at least one nasal nerve while the ultrasound transducer is detecting a signal indicating that the ultrasound transducer is proximate to the anatomical feature.

In embodiments the method may further comprise the anatomical feature being a blood vessel.

In embodiments the method may further comprise advancing the surgical probe into the nasal cavity by determining that the surgical probe is advancing through a middle meatus by detecting a middle turbinate in the nasal cavity with the ultrasound transducer.

In embodiments the method may further comprise a surgical probe with the probe shaft comprising an articulation joint configured to facilitate articulation of the ultrasound transducer relative to the cryo-ablation element. Determining the location of the target treatment site with the ultrasound transducer may comprise articulating the ultrasound transducer with the articulation joint to sweep an area of tissue within the nasal cavity.

In embodiments the method may further comprise the surgical probe having a light emitting element coupled to the probe shaft. When the location of the target treatment site is determined the light emitting element may emit a visual indication within the nasal cavity.

In embodiments the method may further comprise a surgical probe with a haptic feedback element coupled to the handle. When the location of the target treatment site is determined the haptic feedback element may emit a haptic indication.

In embodiments the method may further comprise the cryo-ablation element comprising an expandable structure. Further, cryogenically ablating the target treatment site may comprise inflating the expandable structure through evaporation of a cryogenic fluid within the expandable structure.

In embodiments the method may further comprise monitoring a size of an ice ball formed while cryogenically ablating the target treatment site with the ultrasound transducer or a second ultrasound transducer coupled to the probe shaft. The ultrasound transducer or the second ultrasound transducer may emit an ultrasound beam at an angle relative a longitudinal axis of the probe shaft in order to intersect tissue in the nasal cavity where the ice ball forms.

In embodiments the method may further comprise terminating cryogenic ablation when the size of the ice ball reaches a predetermined size range.

In embodiments the method may further comprise the cryo-ablation element being slidably coupled to the probe shaft. In embodiments, after the location of the target treatment site is determined the cryo-ablation element is advanced into the nasal cavity by sliding the cryo-ablation element along the shaft toward the distal end of the surgical probe shaft to the target treatment site.

Embodiments further include methods for treating rhinitis by advancing a surgical probe into a nasal cavity of a patient. The surgical probe may comprise an elongated probe shaft with a proximal end and a distal end, a handle coupled to the proximal end, and an ultrasound transducer coupled at the distal end of the probe shaft. The method may comprise detecting an anatomical feature within the nasal cavity with the ultrasound transducer in order to determine a location of a target treatment site, advancing a cryo-ablation element slidably coupled to the probe shaft toward the distal end to the determined target treatment site location while the ultrasound transducer is positioned proximate to the detected anatomical feature; and cryogenically ablating the target treatment site, while the ultrasound transducer is positioned proximate to the detected anatomical feature, in order to ablate at least one nasal nerve to reduce at least one symptom of rhinitis.

In embodiments the method may further comprise the anatomical feature being a blood vessel, and detecting the location of the anatomical feature by detecting a blood flow in the blood vessel.

In embodiments the method may further comprise the blood vessel being the sphenopalatine artery or vein.

In embodiments the method may further comprise the cryo-ablation element being, and wherein cryogenically ablating the target treatment site comprises inflating the expandable structure through evaporation of a cryogenic fluid within the expandable structure.

In embodiments the method may further comprise the expandable structure having a lumen, and wherein advancing the cryo-ablation element comprises sliding the probe shaft through the lumen.

In embodiments the method may further comprise a distance between the detected anatomical feature and the target treatment site location corresponding to a distance between a sphenopalatine artery or vein and the at least one nasal nerve.

Embodiments include methods for evaluating a treatment procedure within a nasal cavity of a patient based on a tissue characteristic measured with ultrasound. The method comprise evaluating a pre-treatment tissue characteristic with a first ultrasound scan of the nasal cavity, performing a treatment procedure within the nasal cavity, evaluating a post-treatment tissue characteristic with a second ultrasound scan of the nasal cavity, and evaluating a change between the pre-treatment tissue characteristic and the post-treatment tissue characteristic to assess an effectiveness of the treatment procedure.

In embodiments the method may further comprise performing the treatment procedure comprises cryogenically ablating at least one nasal nerve to reduce at least one symptom of rhinitis. The pre-treatment tissue characteristic and the post-treatment characteristic may be mucosal tissue thickness, edema, or fluid content.

In embodiments the method may further comprise evaluating the change between the pre-treatment tissue characteristic and the post-treatment tissue characteristic by accounting for a contact force applied to a nasal cavity wall by an ultrasound transducer or an angle of incidence of an ultrasound beam.

In embodiments the method may further comprise the first and second ultrasound scans comprise echogenicity, elastography, or elasticity measurements of the mucosal tissue.

In embodiments the method may further comprise re-treating the nasal cavity in response to the evaluation of the change between pre-treatment tissue characteristic and the post-treatment tissue characteristic.

In embodiments the method may further comprise performing the treatment procedure comprises mechanically, chemically, electrically, or thermally treating the nasal cavity.

Embodiments include surgical probes for treating rhinitis of a patient, comprising, an elongated probe shaft with a proximal end and a distal end, a handle coupled to the proximal end, an ultrasound transducer coupled to the probe shaft, and a cryo-ablation element coupled to the probe shaft. The ultrasound transducer may be configured to determine a location of a target treatment site within a nasal cavity of the patient. The cryo-ablation element may be configured to be positioned at the target treatment site location to cryogenically ablate the target treatment site in order to ablate at least one nasal nerve to reduce at least one symptom of rhinitis.

In embodiments the surgical probes may further comprise the ultrasound transducer being configured to detect relative thicknesses of mucosal tissue in the nasal cavity to identify an anatomical landmark correlated to the location of the target treatment site.

In embodiments the surgical probes may further comprise the ultrasound transducer being configured to determine the location of the target treatment site by detecting relative thicknesses of a palatine or sphenoid bone in the nasal cavity in order to identify an anatomical landmark correlated to the location of the target treatment site.

In embodiments the surgical probes may further comprise the ultrasound transducer being configured to determine the location of the target treatment site by detecting a relative boundary or transition between two bones in the nasal cavity or between a bone and cartilage in the nasal cavity to identify an anatomical landmark correlated to the location of the target treatment site. The transition may comprises 0.5-1 mm of cartilage adjacent to 1-3 mm of bone used to identify a perpendicular claims of a palatine bone.

In embodiments the surgical probes may further comprise a second ultrasound transducer coupled to the probe shaft, wherein the ultrasound transducer is coupled to the probe shaft towards the distal end of the probe shaft and distal of the cryo-ablation element, and wherein the second ultrasound transducer is coupled to the probe shaft towards the proximal end of the probe shaft and proximal the cryo-ablation element, and wherein the ultrasound transducer and the second ultrasound transducer are configured to determine the location of the target treatment site by both detecting tissue properties with both.

In embodiments the surgical probes may further comprise the ultrasound transducer and the second ultrasound transducer being configured to detect tissue properties to determine the location of the target treatment site by identifying relative mucosal tissue thicknesses indicating that the cryo-ablation element is positioned proximate to the location of the target treatment site.

In embodiments the surgical probes may further comprise the ultrasound transducer and the second ultrasound transducer being configured to detect tissue properties to determine the location of the target treatment site by identifying relative bone thicknesses indicating that the cryo-ablation element is positioned proximate to the location of the target treatment site. The relative bone thickness may indicate that the ultrasound transducer is detecting a sphenoid bone and the second ultrasound transducer is detecting a palatine bone.

In embodiments the surgical probes may further comprise the cryo-ablation element and the ultrasound transducer being coupled to the probe shaft at a predetermined distance relative to each other. The predetermined distance may corresponds to a distance between an anatomical feature detectable with the ultrasound transducer and the at least one nasal nerve. The ultrasound transducer may be configured to determine the location of the target treatment site by locating the anatomical feature. The cryo-ablation element may be configured to cryogenically ablate the target treatment site by ablating the at least one nasal nerve while the ultrasound transducer is detecting a signal indicating that the ultrasound transducer is proximate to the anatomical feature. The anatomical feature may be a blood vessel.

In embodiments the surgical probes may further comprise the ultrasound transducer being configured to determine that the surgical probe is advancing through a middle meatus by detecting a middle turbinate in the nasal cavity.

In embodiments the surgical probes may further comprise the probe shaft comprising an articulation joint configured to facilitate articulation of the ultrasound transducer relative to the cryo-ablation element, and wherein the ultrasound transducer is configured to determine the location of the target treatment site by articulating the ultrasound transducer with the articulation joint to sweep an area of tissue within the nasal cavity.

In embodiments the surgical probes may further comprise a light emitting element coupled to the probe shaft. The light emitting element may be configured to emit a visual indication within the nasal cavity when the location of the target treatment site is determined.

In embodiments the surgical probes may further comprise a haptic feedback element coupled to the handle, and configured to emit a haptic indication when the location of the target treatment site is determined.

In embodiments the surgical probes may further comprise the cryo-ablation element comprising an expandable structure. The expandable structure is configured to inflate through evaporation of a cryogenic fluid within the expandable structure to cryogenically ablate the target treatment.

In embodiments the surgical probes may further comprise the ultrasound transducer being configured to monitor a size of an ice ball formed while cryogenically ablating the target treatment site. The ultrasound transducer may be configured to emit an ultrasound beam at an angle relative a longitudinal axis of the probe shaft in order to intersect tissue in the nasal cavity where the ice ball forms.

In embodiments the surgical probes may further comprise the cryo-ablation element being configured to terminate cryogenic ablation when the size of the ice ball reaches a predetermined size range.

In embodiments the surgical probes may further comprise the cryo-ablation element being slidably coupled to the probe shaft. The cryo-ablation element may be configured to be advanced into the nasal cavity by sliding the cryo-ablation element along the shaft toward the distal end of the surgical probe shaft to the target treatment site after the location of the target treatment site is determined with the ultrasound transducer.

Embodiments may include a surgical probe for treating rhinitis of a patient, comprising an elongated probe shaft with a proximal end and a distal end, a handle coupled to the proximal end, an ultrasound transducer coupled at the distal end of the probe shaft and a cryo-ablation element slidably coupled to the probe shaft. The ultrasound transducer may be configured to detect an anatomical feature within the nasal cavity in order to determine a location of a target treatment site. The cryo-ablation element may be configured to be advanced toward the distal end to the determined target treatment site location while the ultrasound transducer is positioned proximate to the detected anatomical feature and cryogenically ablate the target treatment site, while the ultrasound transducer is positioned proximate to the detected anatomical feature, in order to ablate at least one nasal nerve to reduce at least one symptom of rhinitis. The anatomical feature may be a blood vessel, and the ultrasound transducer may be configured to detect the location of the anatomical feature by detecting a blood flow in the blood vessel. The blood vessel may be the sphenopalatine artery or vein.

In embodiments the surgical probes may further comprise the cryo-ablation element comprising an expandable structure. The cryo-ablation element may be configured to cryogenically ablate the target treatment site by inflating the expandable structure through evaporation of a cryogenic fluid within the expandable structure. The expandable structure may have a lumen. The cryo-ablation element may be configured to be advanced by sliding the probe shaft through the lumen.

In embodiments the surgical probes may further be configured so that a distance between the detected anatomical feature and the target treatment site location corresponds to a distance between a sphenopalatine artery or vein and the at least one nasal nerve.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

FIGS. 9A-C show an embodiments of a ultrasound probe.
FIGS. 10A-B show a method of locating an SPA using ultrasound and a Doppler signal.

FIGS. 32A-C show embodiments that uses mechanical sensors to guide positioning.

DETAILED DESCRIPTION OF THE INVENTION

In the following description, various embodiments of the present technology will be described. For purposes of explanation, specific configurations and details are set forth in order to provide a thorough understanding of the embodiments. However, it will also be apparent to one skilled in the art that the present technology may be practiced without the specific details. Furthermore, well-known features may be omitted or simplified in order not to obscure the embodiment being described.

In embodiments, ultrasound transducers may be used to detect a Doppler signal indicating the presence of a blood vessel. For example in embodiments the Sphenopalatine Artery (SPA) may be located. Further, in embodiments other blood vessels may be located, for example branches of the SPA or the Anterior Ethmoid Artery. The located blood vessels may be used in determining target ablation sites to treat nerves that may be located based on the location of the blood vessel(s), and the locations of the blood vessels may also be used in order to avoid damage to located blood vessel(s). For example, in embodiments the SPA may be located and the position of the SPA may be used to determine a target ablation site for treating the PNN while avoiding ablating and damaging the SPA. In embodiments, the located blood vessels may then be used in determining target ablation sites that may selectively damage the SPA or other vessels.

Figure 1:
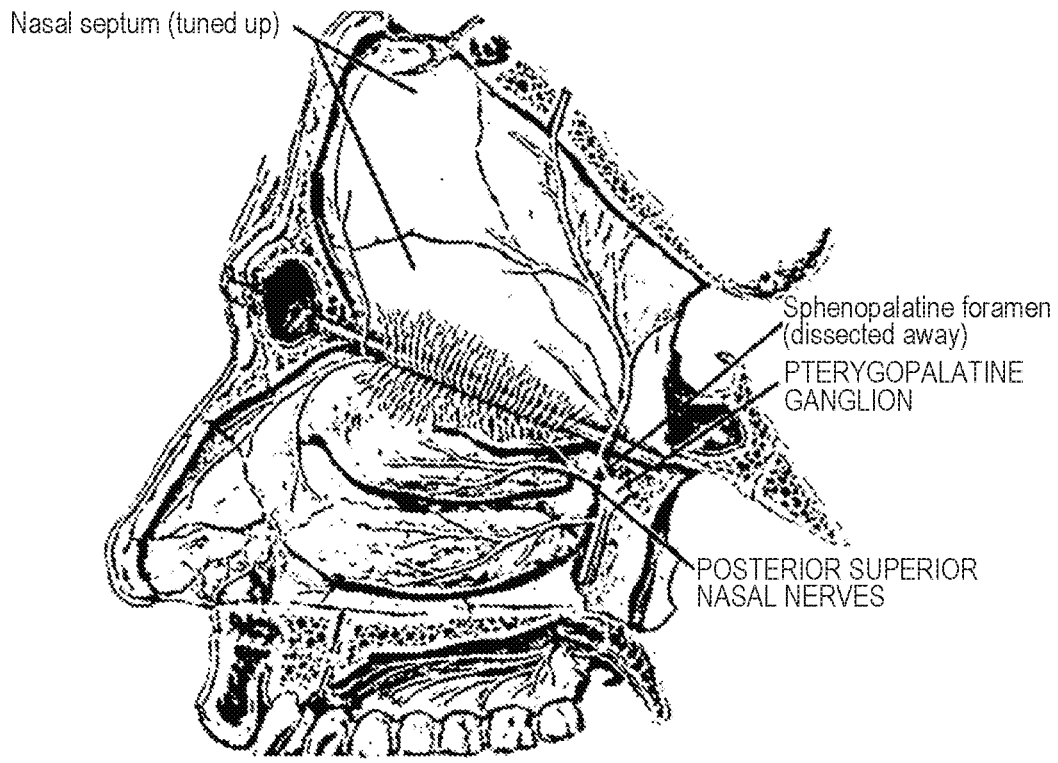
FIG. 1 shows the anatomy of nerves in the nasal canal.
Figure 2:
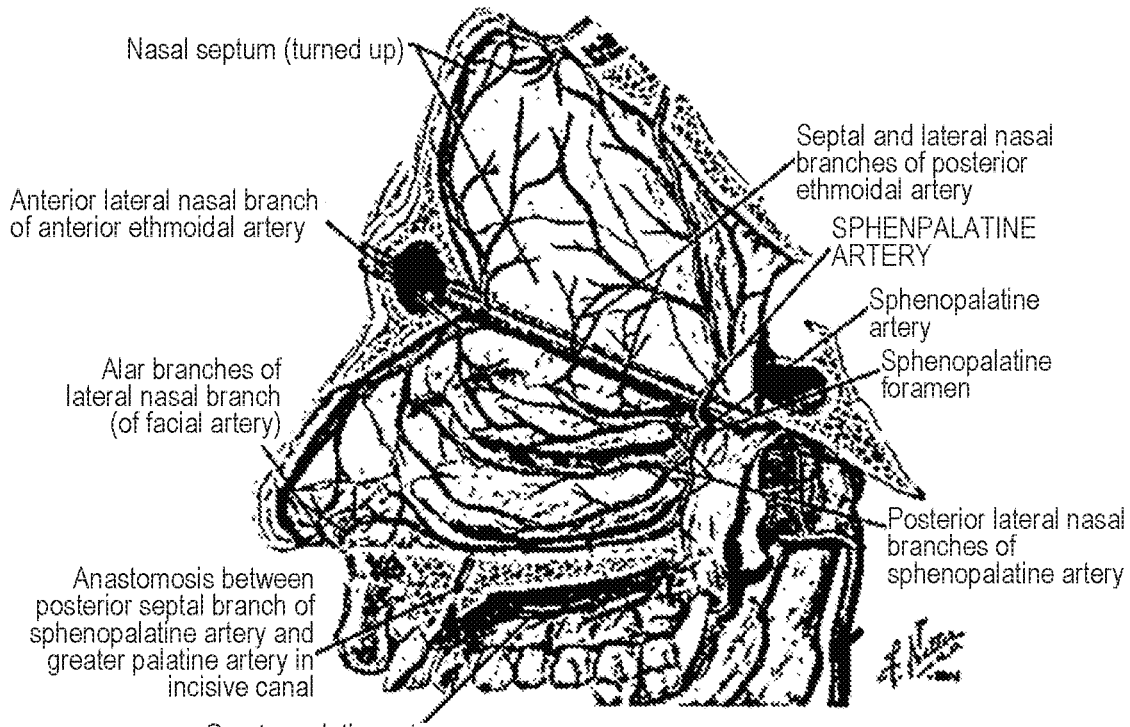
FIG. 2 shows the anatomy of blood vessels in the nasal canal.
Figure 3:
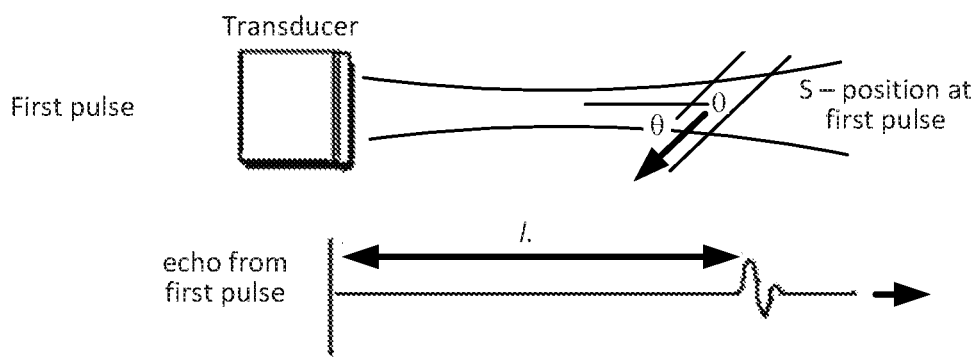
FIGS. 3-5 shows illustrations of detecting a Doppler signal.
Figure 4:
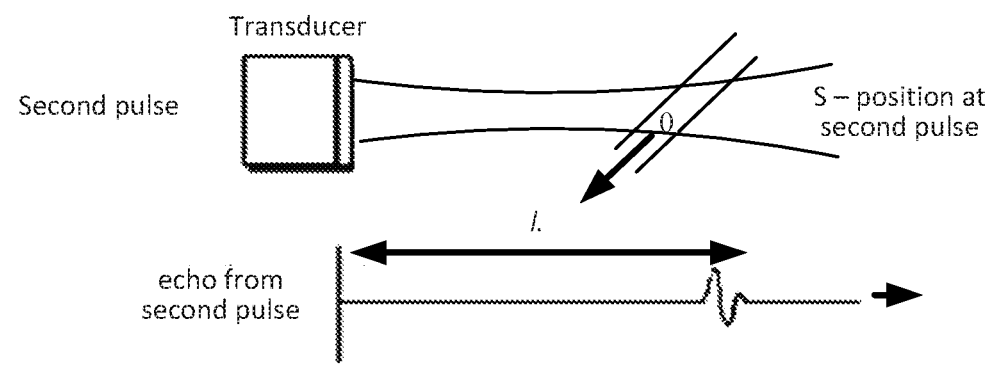

FIGS. 3 and 4 illustrate a method of using multiple pulses being transmitted through a fluid containing moving particles, and shows detected reflections of the pulses as echoes which are time-shifted. Time-shift methods are one mechanism by which tissue motion and/or velocity may be estimated using ultrasound and other imaging modalities. Other mechanisms include frequency-shift analyses and phase-shift estimators. As used herein the terms 'measuring a Doppler shift,' 'measuring a Doppler signal,' or similar language refer to using any of these stated methods, or related methods for estimating tissue movements.

Figure 5:
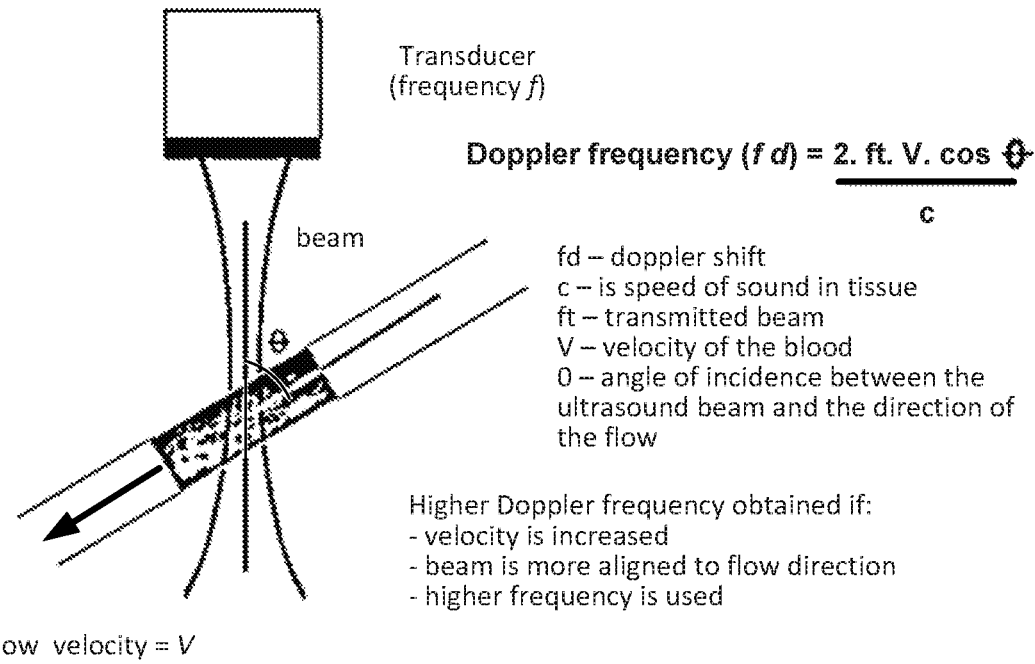

FIG. 5. illustrates an arrangement of a transducer and blood vessel and provides an equation which may be used to determine the velocity of the blood flow. The equation shown is based on sound waves, for example ultrasound, however the Doppler shift can also be observed with other forms of energy, for example visible light, IR, or other acoustic or electromagnetic waves in order to detect blood flow. These forms of energy may be emitted from an emitter and then reflected signals may be received by a receiver and used to detect areas of the body with blood flow in the tissue. Similar methods may be employed to determine other types of tissue motion or movements. The sensing area in which energy is emitted and received may be small and by traversing a sensor for detecting a Doppler shift around a larger area of tissue, as will be discussed in greater detail below, specific areas of the tissue that include blood flow, and therefore a blood vessel, may be determined.

In embodiments, an ultrasound probe may also be used to detect the location of the SPA using other characteristics of vasculature independent of blood flow including ultrasonic reflections and velocity changes through vessel walls and the intraluminal space compared to surrounding tissue.

In embodiments, as discussed in greater detail below, blood vessels, for example the SPA, may be located using an ultrasound probe. The determined location may then be used to inform the operator in order to determine a target treatment site. Ablation therapy at the target treatment site to provide treatment for rhinitis symptoms may then be delivered while avoiding a level of damage to the SPA and its branches which may require repair. As will be discussed in greater detail below, in embodiments a system may include an ultrasound probe and an ablation probe, for example, an ablation probe as disclosed in U.S. Ser. No. 14/503,060, which is incorporated by reference.

In addition to using ultrasound signals to detect blood flow by detecting Doppler shifts, ultrasound signals may also be used to detect anatomical features such as tissue thickness including bone and mucosal thickness, as well as transitions between different types or different thicknesses of tissue. This detection may be performed for example using A-mode or B-mode ultrasound. The detection of anatomical features may be used to determine a location of a target treatment site for ablation. For example, the locations of bony prominences and areas of varying mucosal thickness may correspond to the location of a target nerve in the nasal cavity. Identifying the anatomical features may be used to determine a location of a target treatment site to ablation a target nerve.

A-mode (amplitude mode) ultrasound is a mode in which an ultrasonic pulse is emitted into the tissue and the reflected components of the signal are measured over time. Tissue acoustic impedance is a function of tissue stiffness and the speed of sound in that tissue. A propagating ultrasound wave is reflected at interfaces between tissues with different acoustic impedance, with the degree of signal reflection increasing with increasing differences. Small differences create small echoes and large differences create larger echoes.

The time between ultrasound signal emission and the detection of the reflected signal is a function of the speed of sound in tissue and of the depth at which the signal was reflected. During A-Mode scanning, where the amplitude of received echoes from a transmitted ultrasound pulse is recorded over a period of time, signals reflected from deeper tissues will appear later in the recording than signals reflected more superficially. The table below shows the speed of sound in different common tissues.

To convert echo delay (the time elapsed between transmission of an ultrasound pulse and the detection of the corresponding echo) to depth, the average speed of sound may be used. In soft tissue, the speed of sound is generally considered a constant and attributed a value of 1540 m/s.

$$\text{depth (m)} = \text{avg speed of sound (m/s)} * \tfrac{1}{2} * \text{delay (s)}$$

In the relationship above, the factor of ($\tfrac{1}{2}$) accounts for the fact that the echo delay is comprised of the round-trip travel time of the ultrasound pulse (i.e. the time it takes an ultrasound wave to reach the depth of the reflecting surface plus the time it takes the wave to travel back to the transducer from this point of reflection).

TABLE 1

| Speed of sound in common tissues | |
|---|---|
| Tissue Type | Speed of Sound (m/s) |
| Skin | 1600 |
| Fat | 1400 |
| Muscle | 1600 |
| Bone | 3500 |

The table below shows the percentage of incident signal reflected at the boundaries between different tissues.

TABLE 2

| Percentage reflection of ultrasound at boundaries: From: Aldrich: Crit Care Med, Volume 35(5) Suppl. May 2007.S131-S137 | |
|---|---|
| Boundary | % Reflected |
| Fat/muscle | 1.08 |
| Fat/kidney | 0.6 |
| Soft tissue/water | 0.2 |
| Bone/fat | 49 |
| Soft tissue/air | 99 |

Figure 6:
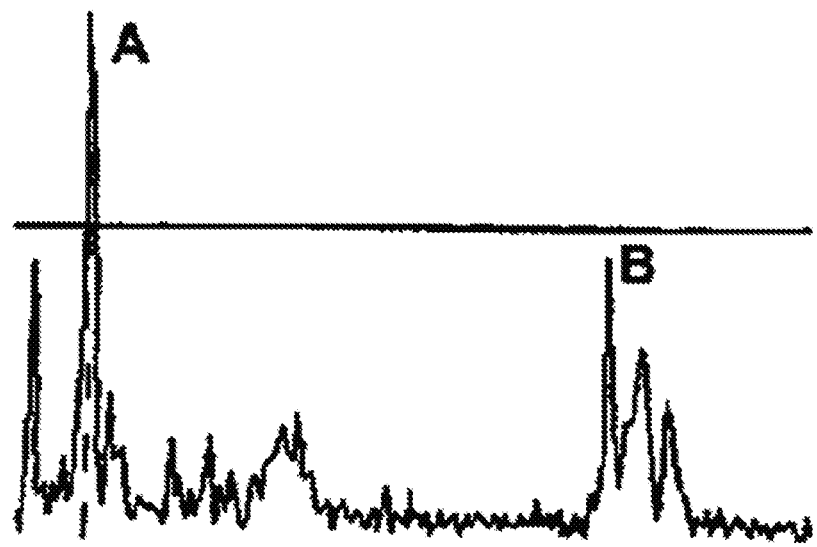
FIG. 6 shows an A-mode scan with the y-axis representing reflected signal intensity and the x-axis representing the time between signal emission and the time of signal detection.
Figure 7A:
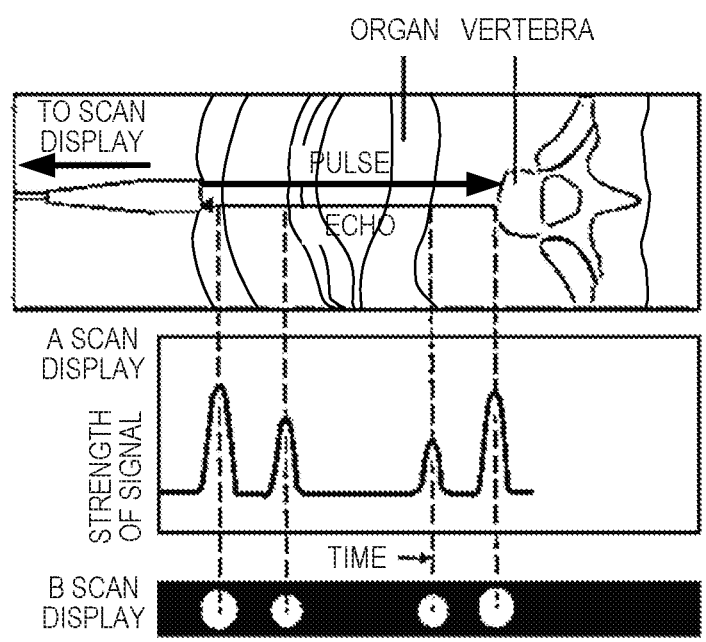
FIG. 7A shows A-mode and B-mode scans showing tissue interfaces and their associated ultrasonic echoes in the back/spine.
Figure 7B:
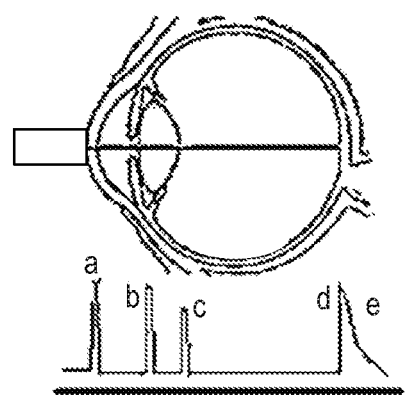
FIG. 7B shows an A-mode scan showing tissue interfaces and their associated ultrasonic echoes in the eye.

FIGS. 6 and 7A-B show examples of A-mode scans. In FIG. 6 the y-axis represents reflected signal intensity and the x-axis represents the time between signal emission and the time of signal detection. In FIG. 6, spikes A and B represent interfaces between tissues of markedly different acoustic impedances. Spike A represents an interface which is more superficial than spike B and in which the difference in acoustic impedance between the tissues is greater than that in spike B. The depths of tissue interfaces represented by spikes A and B can be estimated by multiplying the average speed of sound in tissue by ½ the delay between signal emission and detection of the associated reflections.

In embodiments, the depth of mucosal tissue, the depth of bones, the thickness of bones in the nasal cavity, and transitions between different tissue thicknesses and densities may be determined using A-mode scans. In embodiments, the detectable spikes on an A-mode trace, corresponding to the interfaces of tissues with markedly different acoustic impedances, may be used to estimate the superficial and deep boundaries of the mucosal tissue. From these estimations, thickness measurements may be made. For example, in embodiments, a large A-mode spike may be detected that corresponds to the interface of a coupling balloon and the superficial mucosal wall, and a second large A-mode spike may be produced that corresponds to the interface of the deep mucosal tissue and bony tissue. The distance between these spikes, calculated using time delays and estimated ultrasound propagation speeds, allows for calculation of the thickness of mucosal tissue. In embodiments, mucosal tissue thickness may not be measured directly, and bony landmarks may instead be identified. In embodiments that identifying bony landmarks, A-mode ultrasound may be used to locate the area of treatment by determining where there are bony landmarks including areas in which bone thickness changes.

FIG. 7A shows example A-mode and B-mode scans showing tissue interfaces and their associated ultrasonic echoes in the back/spine. FIG. 7B. shows an A-mode scan showing tissue interfaces and their associated ultrasonic echoes in the eye. A-mode and B-mode scans within the nasal cavity will show similar spikes due to interfaces of various tissue types.

In embodiments, ultrasound techniques, such as A-mode and B mode scans, may be used to locate bony landmarks such as foramen, and more particularly the sphenopalatine foramen. The sphenopalatine foramen is an opening in the bone through which the SPA and posterior nasal nerves run. For example, as described above an A-mode signal may be used to show a thickness and/or reflection amplitude measurement for palatine and sphenoid bone surrounding the foramen, and may show different signal characteristics when the ultrasound beam is aimed at the foramen. For example, there may be reduced acoustic shadowing and/or reflection associated with the foramen.

In embodiments, ultrasound may be used to detect the differences between cartilage and bone. The impedance differences between cartilage and mucosal tissue are smaller than those between bone and mucosal tissue, and A-mode measurements of echoes from areas of underlying cartilage result in lower amplitude signals than measurements in areas of underlying bone. These differences in signal amplitude may be used to differentiate between areas or to locate the transition between areas.

In embodiments, mucosal tissue thickness may be measured using A-mode ultrasound prior to treatment. These measurements may be used to guide operator in administration of decongestants. Tissue thickness information may also be used prior to treatment to determine treatment dosage including ablation member target temperature and treatment duration and, in multi-cycle treatment paradigms, the number of cycles or treatment time. For example, thicker mucosal tissues may require longer treatment times, lower temperatures, and/or more treatment cycles than thinner mucosal tissues. Treatment time may be tailored using the tissue thickness and tissue penetration rates.

Ultrasound measurements may be used during treatment to detect changes in tissue properties that are associated with freezing, or may be used post-treatment to assess any tissue changes that were produced as a result of the ablation treatment. For example, both during and post-treatment, ultrasound signals may detect changes in tissue acoustic impedance (as indicated by changes in echogenicity of the target area).

Ultrasound measurements may be performed at the treatment site before treatment to measure baseline characteristics of the tissue to be treated. These characteristics may include tissue thickness, echogenicity, elasticity, local blood flow, or degree or type of motions (physiological or otherwise) measured.

In embodiments, gain compensation may be used to compensate for known losses in ultrasound signal strength that will be present in echoes arising from deeper regions of tissue. As an ultrasound wave propagates through tissue, its intensity decreases exponentially with depth as a result of both scattering and absorption. This loss in intensity is proportional to the ultrasound frequency used and dependent on the properties of the tissues interrogated. The attenuation coefficient is generally specified in units of dB/cm/MHz, where dB refers to decibels. In soft tissues, the attention coefficient ranges generally from 0.5 to 1.0, though it is lower (~0.2) in blood and much higher (~10+) in bone. Gain compensation may be performed by estimating the signal intensity loss expected over a depth of interest and mathematically adjusting measured signals to compensate. In embodiments, this may aid in comparisons of tissue interfaces, for example by allowing for nearly identical tissue interfaces to produce similar A-mode amplitudes even if these interfaces occur at meaningfully different depths from the transducer.

Using techniques similar to those described above, A-mode ultrasound may be used to measure bone thickness, distinguish between cartilage and bone, or distinguish between bone of different thickness. A-mode ultrasound may also be used to identify transitions between cartilage and bone or between bones of differing thickness.

The sphenopalatine foramen through which the sphenopalatine artery and posterior nasal nerves enter the nasal cavity is at the intersection of the palatine bone and the much thicker sphenoid bone superior to the posterior fontanelle of the Maxillary sinus. A-mode ultrasound may detect differences in mucosal thicknesses in regions proximate to these bones and fontanelle, where the mucosal tissue is thicker overlying the palatine bone than the sphenoid bone. The interface between these bones and cartilage may also be determined by examining mucosal thickness in various locations and searching for a transition. In embodiments, a transition may be located using an array of two or more transducers and comparing measured mucosal thickness, as will be discussed in greater detail below. In embodiments, a transition is located by mechanically sweeping one or more transducers across a region of interest, making multiple mucosal thickness measurements at points within this region, and indicating to the operator (either in real-time or retrospectively) when the thickness change has exceeded a predefined threshold corresponding to the transition. For example, this indicator may be an LED, as will be discussed in greater detail below, that illuminates when measured mucosal thickness has changed to indicate that the transducer has moved from being over the sphenoid bone to being over the palatine bone (or vice-versa). In embodiments, ultrasound scans may also be used to approximate the routing of the nerves branching inferiorly from the SPF and the nerves innervating through the palatine bone. The perpendicular plate of the palatine bone anteriorly meets and connects with a very thin eggshell cartilage which is the medial wall of the maxillary sinus. The cartilage in this area is less than 0.8 mm thick and the palatine bone is ~2 mm thick. Using ultrasound this transition could be detected and provide feedback to the user that they have reached the target area for the posterior nasal nerves. A-mode or B-mode ultrasound measurements may be used to detect the thickness of palatine and sphenoid bone or otherwise identify the transition between these two bones. In embodiments, ultrasound may be used to detect differences in the amplitude of the signal reflected by thin palatine and thick sphenoid bones. More energy may pass through the palatine bone resulting in a lower amplitude reflection. Conversely, the sphenoid bone may reflect more signal resulting in the detection of a larger amplitude echo.

In embodiments, the amount of ultrasound energy propagating beyond the bony interface may be used to identify the transition between the two bones in the nasal cavity. For example, the sphenoid bone is relatively thick compared to the palatine bone and will result in increased attenuation, via absorption, scattering, and/or reflection, of the ultrasound beam and results in increased acoustic shadowing (i.e. very low echo strength in deeper regions) compared to the thinner palatine bone. The relative degree of acoustic shadowing, as measured by the A-mode signal strength detected at depths beyond the bone interface (indicated by a spike in the A-mode trace), may be used to indicate whether the transducer is aiming at a thin or thick bone structure, for example the palatine or sphenoid bones. By sweeping the transducer interrogation zone across a region of interest or by using an array of ultrasound transducers, as will be discussed in great detail below, the transition between these two bones may be identified.

The angle of the axis of an ultrasound beam emitted from an ultrasound transducer with respect to the tissue surface can impact both ultrasound thickness and Doppler flow measurements. In order to provide accurate tissue thickness measurements during A-mode ultrasound scanning, the transducer face is required to be orthogonal to the tissue surface. Measurement error increases in direct proportion with increasing angle away from the orthogonal, 90° angle. Doppler frequency $f_d$ is related to both the velocity V of a moving particle and to the angle θ between its direction of movement and the axis of ultrasound energy. The relationship is described in the equation:

$$f\_d = (2*f\_t*V*\cos θ)/c \qquad 1.1.1$$

1.1.2. where:
   1.1.2.1. ft is the frequency of ultrasound signal
   1.1.2.2. c is the speed of sound in tissue The factor cos θ approaches zero when the angle θ approaches 90°. When the Doppler transducer is orthogonal to the direction of blood flow, the signal decreases and flow may become undetectable. For this reason, maintaining an orientation of the transducer relative to the tissue surface is important. As the sphenopalatine artery passes through the sphenopalatine foramen, the vessel turns nearly 90° straight down to traverse the wall of the nasal cavity. In this transition the orientation of the vessel and blood flow changes. By detecting the change in signal associated with this transition, the user may be able to locate the sphenopalatine foramen and use this landmark to guide in treatment placement. For example, the Doppler signal measured by a transducer may change from a meaningful signal to a negligible signal as the transducer moves along the vessel towards the foramen, suggesting that the vessel may be turning to become more orthogonal with respect to the transducer beam angle. This may be used as an indication that the foramen is nearby, thus providing an anatomical landmark which may allow for more rapid and/or accurate placement of the probe in the intended ablation region.

The ultrasound scans as discussed above, including Doppler, A-mode, B-mode and M-mode, may be performed using various devices including one or more ultrasound units, also referred to as ultrasound transducers, each comprising an ultrasound emitter and ultrasound receiver which are used to generate a signal which is processed by a processing unit to generate the scan signals of Doppler, A-mode, B-mode and M-mode. In embodiments, a single component acts as both the ultrasound emitter and receiver. As discussed above, these signals may be used to determine the locations of vasculature in the nasal cavity, innervation in the nasal cavity, tissues and bone thicknesses in the nasal cavity, bony landmarks, and boundaries between different densities of tissue.

Figure 8:
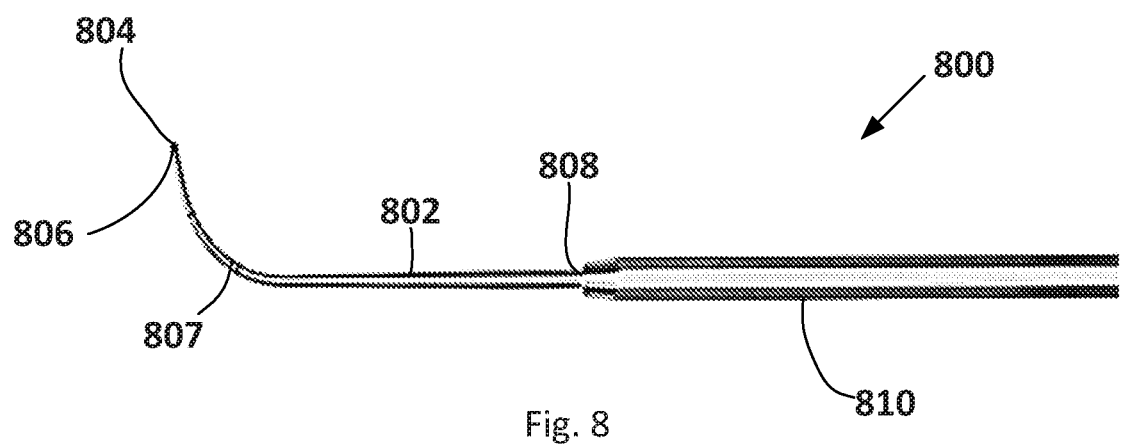
FIG. 8 shows an embodiment of an ultrasound probe.

In embodiments, an ultrasonic probe 800 may comprise a shaft 802 and an ultrasound transducer 804 coupled to a distal end 806 of the shaft, for example as shown in FIG. 8. The shaft 802 may be straight or may have one or more bends 807 between the distal end 806 and a proximal end 808 coupled to a handle 810. The bends in the shaft may be configured to complement bone structures within the nasal cavity in order to facilitate insertion into the nasal cavity and contact between the ultrasound transducer and tissue surfaces. The bends may form an angle between a distal and proximal end of the shaft ranging from 30°-90°. The distal portion end of the shaft may be between 5 mm and 20 mm.

In embodiments, the angle of the ultrasound transducer relative to the longitudinal axis of the distal tip of the shaft may be based on the modality of ultrasound that the probe is intended to utilize. For example, because the angle of incidence between the direction of blood flow and the axis of energy transmission can affect the magnitude of the detected Doppler signal, the angle at which the ultrasound transducer is mounted to the distal end of the probe may be such that the transmission path of the transducer is aligned with the axis of the distal arm. Alternatively, the transducer may be mounted such that the axis of the transducer probe is at some non-parallel angle relative to the axis of the arm. The orientation of the transducer probe axis relative to the distal arm may be fixed. In embodiments, the scanning position of the ultrasound transducer may be moved by changing the angle of the distal end of the shaft relative to the proximal end of the shaft, or by altering the position of the entire apparatus within the nasal cavity during use. In embodiments, the orientation of the transducer probe axis relative to the arm may be variable. In embodiments, the scanning position of the ultrasound unit may be altered independently of changing the angle between the distal arm and the shaft or moving the entire apparatus.

In embodiments, the angle between the distal portion of the arm coupled to the ultrasound transducer and the proximal portion of the arm may be varied. For example, as shown in FIGS. 9A-C, a shaft 902 of a surgical probe 900 may include an articulating joint 904 between the proximal end 906 of the shaft, and the distal end 908 of the shaft including the ultrasound transducer 910. While the distal portion 908 of the ultrasound probe is positioned within a general region of the nasal cavity where ablation is likely to be performed, the articulating joint 904 may be used to traverse the mucosal surfaces of the nasal cavity with the ultrasound transducer 910 at the distal tip. At various points in the nasal cavity, or continuously as the ultrasound transducer is being traversed within the nasal cavity, the processing unit instructs the ultrasound emitter to emit an output signal and further receives a detected signal from the ultrasound receiver. The ultrasound output signal passes through tissue and may be absorbed, transmitted or reflected by the internal tissue structures dependent on the ultrasound properties of the tissues. The ultrasound energy which is reflected is received as the detected signal, and may be used to identify anatomical features, as discussed above.

In embodiments, the size of a blood vessel may be measured by scanning the nasal cavity surface with an ultrasound signal and estimating the distance over which a threshold Doppler signal is detected. In embodiments, the size of a blood vessel may be measured by physically moving an apparatus that contains a fixed position ultrasound transducer, for example as shown in FIG. 8, or moving a portion of an apparatus with the ultrasound transducer relative to the rest of the apparatus, as shown in FIGS. 9A-C. Further, in embodiments, steered ultrasound beams, for example with a phased array, may be used to scan the scan region. In embodiments, pulsed Doppler techniques are used at varying depths to estimate the thickness of a vessel in the direction parallel to the beam transmission axis.

The processing unit may have predetermined Doppler signal thresholds set corresponding to typical blood flow in a targeted vessel (for example, the SPA), in order to determine if a detected blood flow is from the vessel of interest. Wall filters and other processing may be implemented to isolate blood flow from low velocity clutter signals which improve the performance of the processing unit when demarcating vessel boundaries.

In embodiments the ultrasound probe may be traversed along surfaces where the SPA is anticipated to be located. For example, as shown in FIG. 10A the ultrasound probe 1000 may be traversed from a first position 1001 to a second position 1002 which in this example are on either side of the SPA 1003. When this scanning occurs the Doppler signal has a peak amplitude at a position between the first position and the second position, as shown in FIG. 10B. When the processing unit detects a peak as shown in FIG. 10B an alert in the form of an audio or visual or tactile/haptic indication may be executed in order to notify the operator that a blood vessel, for example the SPA, is located. In embodiments the alert is provided as soon as the Doppler signal surpasses a previously defined threshold corresponding to a threshold associated with the expected blood flow of the blood flow being searched for. In embodiments the full scan from the first position to the second position takes place, the peak from the complete scan is identified, and the alert is provided as the ultrasound probe re-traces its path back towards the first position.

In embodiments, scanning methods similar to those shown in FIG. 10A may be performed with transducers configured to operate in A-mode or B-mode and may be used to detect maximum, minimum, or transitions in thickness of soft tissue or bone in order to identify treatment sites for ablation.

Figure 11A:
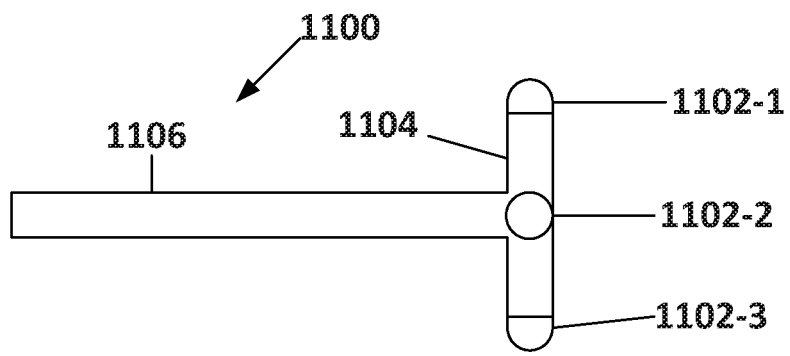
FIG. 11A shows an embodiment of an ultrasound probe with multiple ultrasound units.

In embodiments, an ultrasound probe may include more than one ultrasound emitter and/or more than one ultrasound receiver attached at different portions of the ultrasound probe. In multiple ultrasound transducer embodiments a plurality of ultrasound signals corresponding to different positions of the probe may be processed by a processing unit to determine the position of an anatomical feature, such as the SPA or a foramen, relative to multiple positions on the probe. The ultrasound transducers may be arranged such that the there is a fixed distance between them. The ultrasound transducers may be arranged in a linear fashion, for example as shown in FIG. 11A. As shown, the probe 1100 includes three ultrasound transducers 1102, including a left 1102-1, a center 1102-2 and right 1102-3 in a line on a crossbar 1104 at the distal end of the probe. The crossbar 1104 is perpendicular to the longitudinal axis of the shaft 1106 of the probe. In embodiments, the angular position of the left and right ultrasound transducers is fixed and movement is limited to position shifts that change the proximity of the transducers with relation to the center transducer. In embodiments, the insonification angle of the transducers may be variable with or without accompanying overall position changes. In embodiments, the ultrasound transducers may be arranged in a rectangular array or circular array. In embodiments other spatial configurations, including any number of ultrasound transducers, may be used, for example four transducers in a circular pattern facing in opposite directions at the distal end of a probe shaft and configurations with five transducers in a line along the longitudinal axis of the probe shaft with each facing the same direction. Arrays of ultrasound transducers have the advantage of allowing for larger areas to be scanned at once as well as providing a more accurate determination of the location of anatomical features relative to different portions of the probe.

Figure 11B:
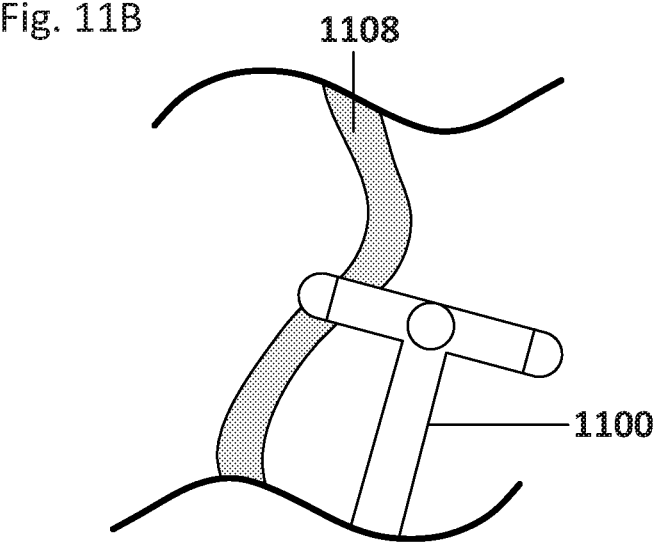
FIGS. 11B-C show using the probe of FIG. 11A to locate the SPA.
Figure 11C:
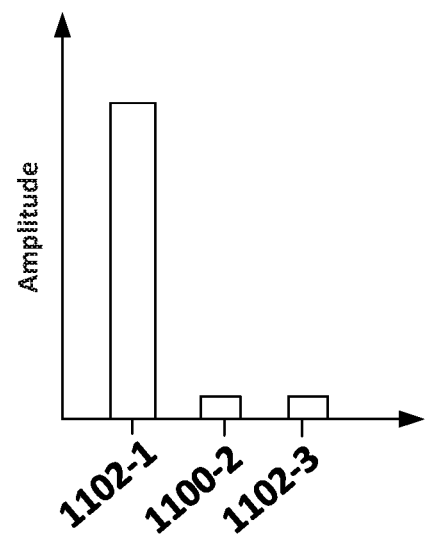
Figure 12A:
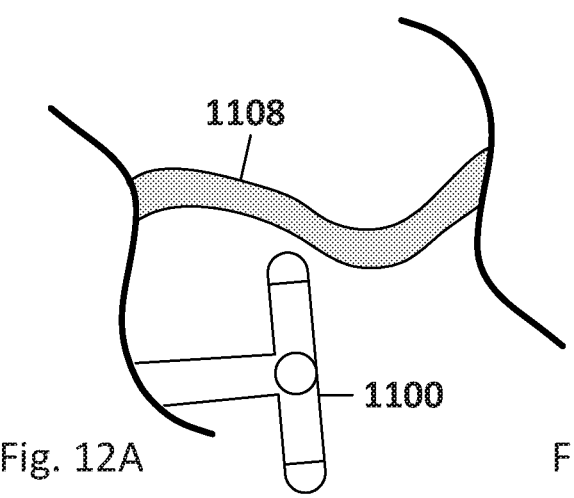
FIG. 12A-F show using the probe of FIG. 11A to locate the SPA.
Figure 12B:
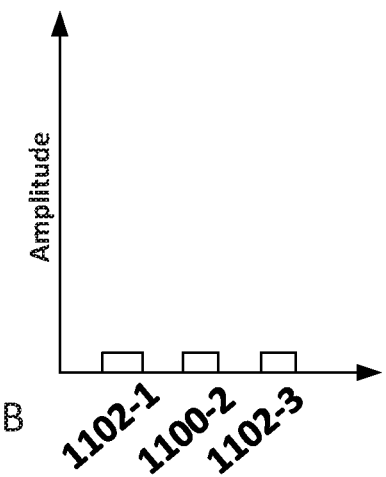
Figure 12C:
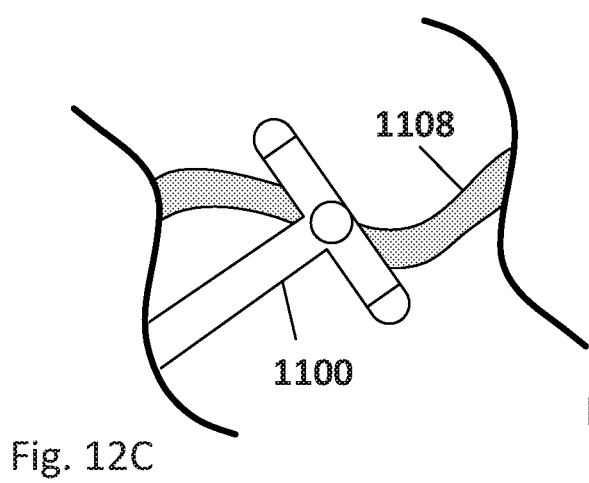
Figure 12D:
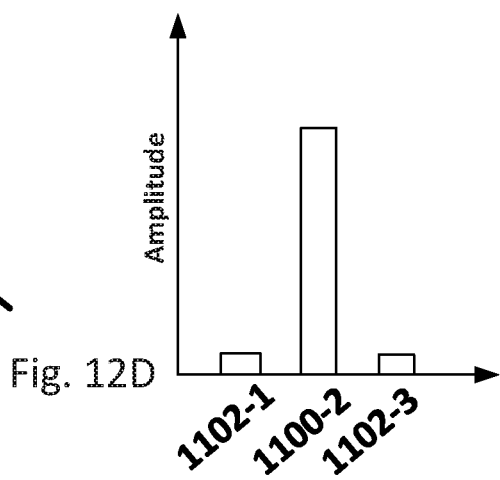
Figure 12E:
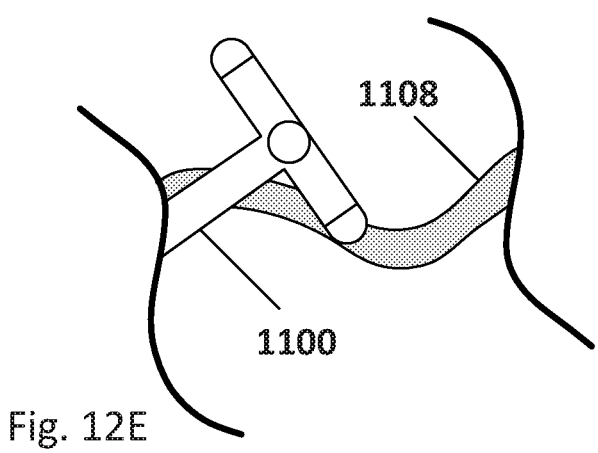
Figure 12F:
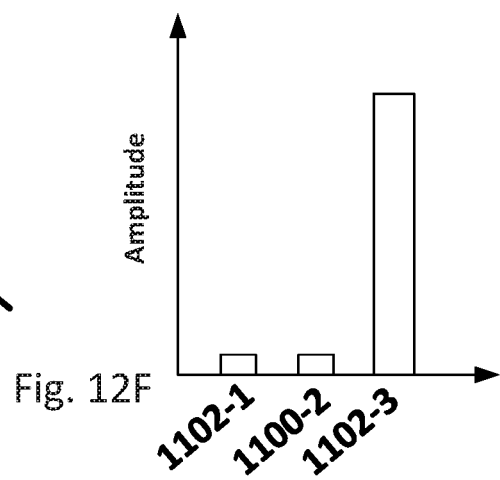

In embodiments including Doppler scans, when a multi ultrasound transducer probe is placed in proximity to a vessel, only the ultrasound transducers emitting signals incident to the blood flow will detect a Doppler shifted signal while the other ultrasound transducers in the array will not. Therefore, the location and/or orientation of a blood vessel may be determined based on the detection or lack of detection of a Doppler shift during a single point of time or during a scan. For example, as shown in FIG. 11B a probe 1100 may be positioned in the nasal cavity in the general area where the SPA 1108 is located. The probe 1100 may be traversed until one or more of the ultrasound transducers 1102 detects a Doppler shift indicating blood flow associated with the SPA 1108. For example as shown in FIG. 11B, only the left ultrasound transducer 1102-1 is incident to the blood flow through the SPA 1108. Therefore, as shown in FIG. 11C only the left ultrasound transducer detects a meaningful Doppler signal while the center and right transducers do not.

The pattern of transducers detecting Doppler signals during a scan may be used to estimate the location of vessels, the orientation of a vessel, or to estimate the vessel size. Detecting the positon of vessels such as the SPA relative to multiple sensors is advantageous in allowing more precise and faster location of anatomical landmarks. Multiple sensors may interrogate a broader range of tissues simultaneously and as such also allow for less traversing of the ultrasound probe to determine the location of an anatomical feature, using Doppler, A-mode or B-mode scans. For example, as shown in FIGS. 12A-12F, the crossbar of the probe 1100 may be traversed within the nasal cavity and the processing unit may analyze Doppler signals from each transducer over a period in order to determine peak signals of each and determine the location of the SPA 1108.

Figure 13A:
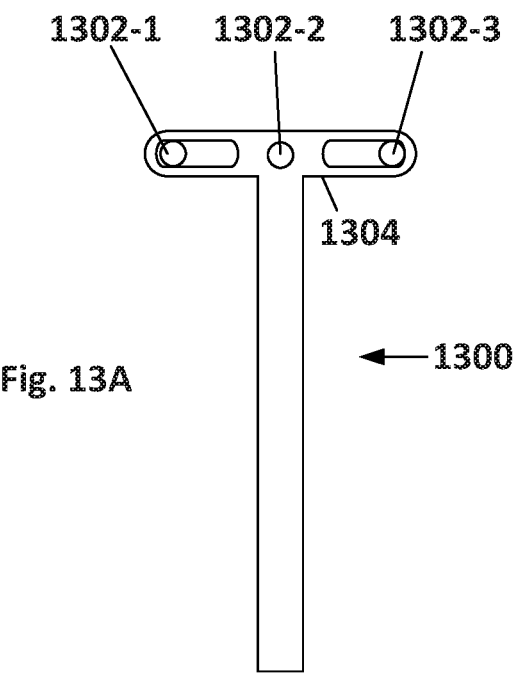
FIGS. 13A and 13B shows an embodiment of an ultrasound probe with slidably ultrasound transducers.
Figure 13B:
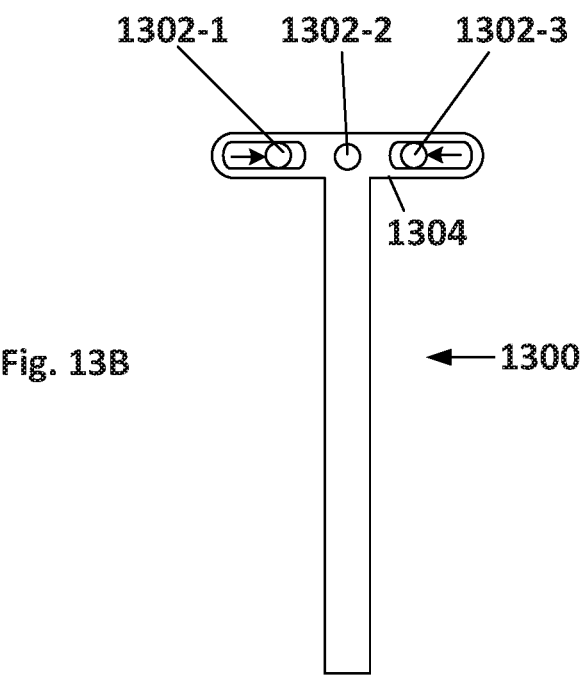

In embodiments, ultrasound units may be positioned on independently steerable arms branching out from a main shaft of a probe. In embodiments ultrasound transducers 1302 in an array may be moveable along a crossbar 1304 of a probe 1300 as shown in FIGS. 13A and 13B. As shown left 1302-1 and right 1302-3 transducers are located in recessed tracks within the crossbar 1304 section of the probe 1300. The positions of the left 1302-1 and right 1302-3 ultrasound transducer units may be altered in tandem or independently and the center transducer 1302-2 may be coupled to the crossbar 1304 at a fixed position. In embodiments, the position of the transducers is altered using buttons, toggles, sliders, and/or dials located at the proximal handle end of the probe.

In embodiments, a surgical probe may include visual indicators which indicate information about the location of the anatomical features detected by the ultrasound transducers. For example the visual indicator may provide feedback for adjusting the orientation of a probe for locating the SPA. The visual indication may be displayed with an LCD (or other type screen), a single LED or an array of two or more LEDs. Information about the location may be related by different intensities, different colors, or patterns of on/off (i.e. blinking pattern), and/or color of multiple LEDS. In embodiments, the LEDs may be multi-color LEDs and the processing unit controls the LEDs to display a different color based on predetermined thresholds of ultrasound corresponding to different detected thicknesses or distance.

Figure 14:
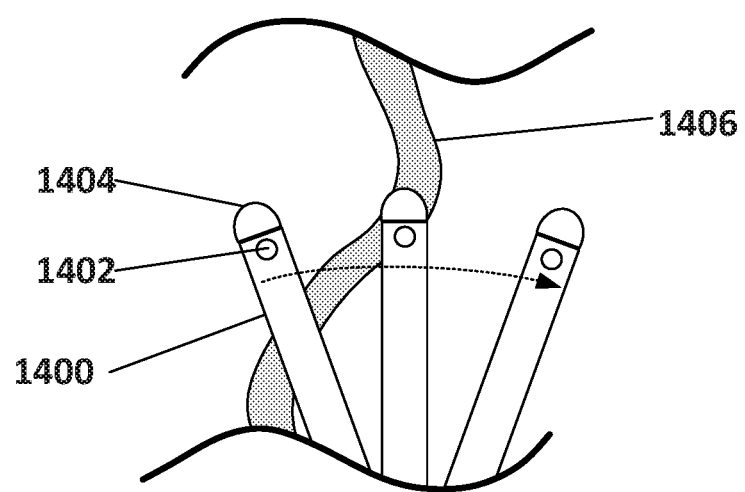
FIG. 14 shows an embodiment of an ultrasound probe with a visual indicator.

In embodiments, for example as shown in FIG. 14, an ultrasound probe 1400 may include an LED 1402 at the distal tip proximate to the ultrasound transducer 1404. As the probe 1400 is traversed in the vicinity of the SPA 1406, for example as disclosed in relation to FIG. 10A, the LED 1402 provides an indication when the ultrasound transducer detects a Doppler shift resulting from the blood flow in the SPA. In embodiments, LEDs may blink at different rates or patterns to indicate the intensity of an ultrasound signal to locate an anatomical feature. In embodiments including LEDS on the probe, an operator may visually observe the LEDs either directly or through a camera imager inside of the nasal cavity to receive the direction information indicated by the LEDs to determine the position of the anatomical features relative to the probe. In embodiments, the LEDs corresponding to the ultrasound units may be external of the nasal cavity while the device is in use.

Figure 15A:
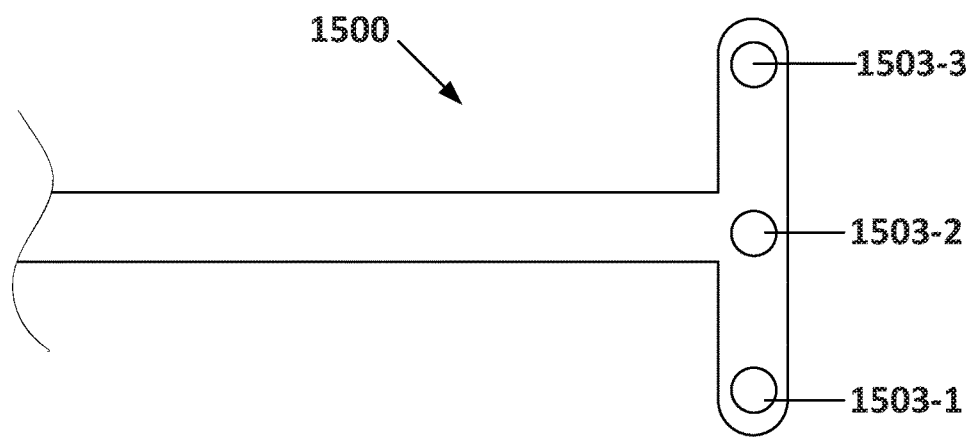
FIGS. 15A and 15B shows an embodiment of an ultrasound probe with multiple visual indicators.
Figure 15B:
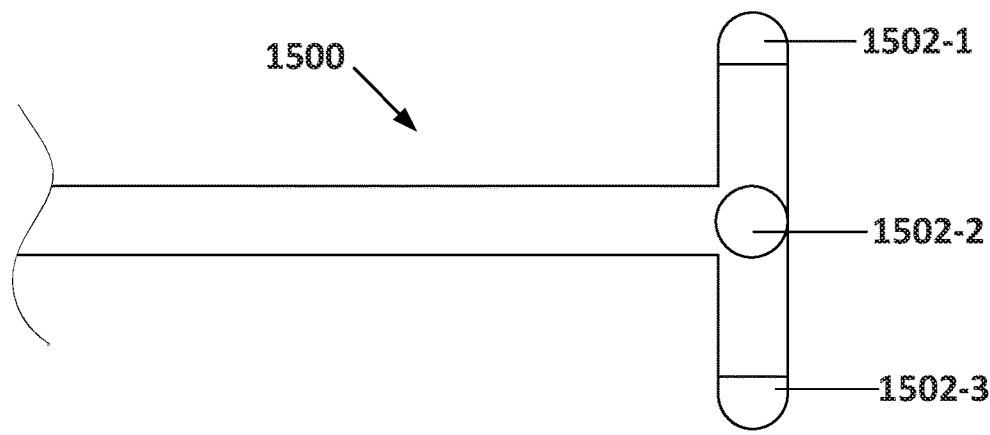

In embodiments, a probe may include multiple visual indicators corresponding to multiple ultrasound transducers. FIGS. 15A and 15B show a probe 1500 similar to the probe of FIG. 11A. The probe includes an LED 1503-1 1503-2 and 1503-3 corresponding to each ultrasound transducer 1502-1 1502-2 and 1503-3. The LEDs are located proximate to the corresponding ultrasound transducer. An operator may traverse the probe within a nasal cavity and the processing unit will adjust the intensity of each LED to correspond to the ultrasound signal amplitude measured by the corresponding ultrasound transducer.

Figure 16A:
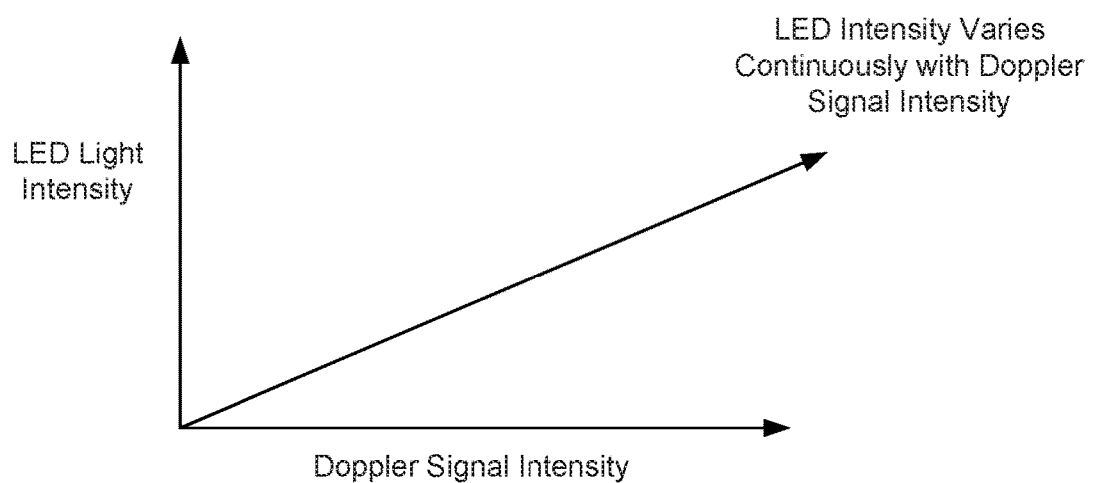
FIGS. 16A and 16B shows an embodiments of providing visual indications of ultrasound signal strength.
Figure 16B:
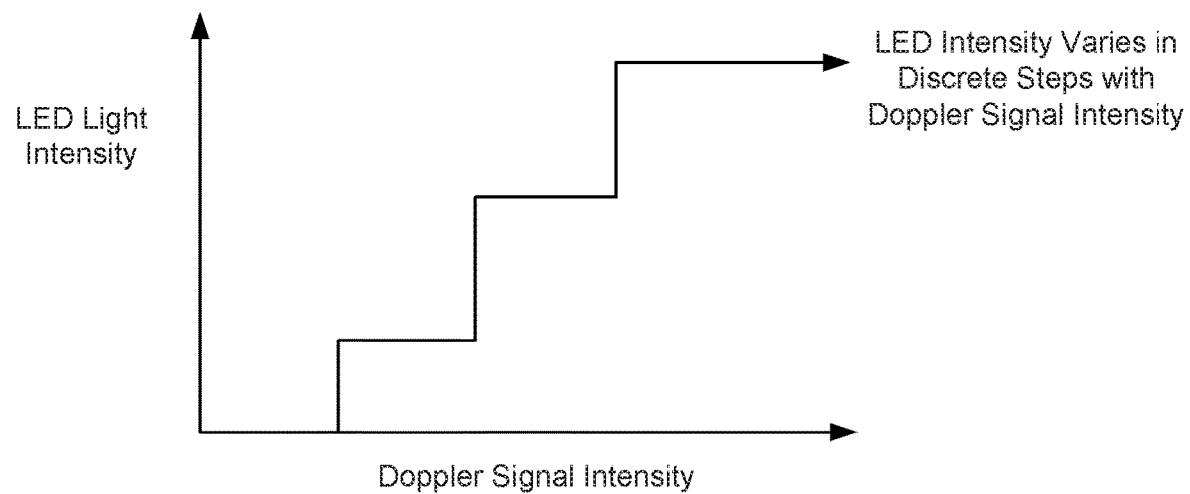

In embodiments the intensity of the LEDs may vary continuously based on ultrasound signals as shown in FIG. 16A, or discretely based on preset thresholds of ultrasound signals as shown in FIG. 16B. In embodiments, the intensity of the LEDs may vary based on time of flight pulse-echo ultrasound measurements of the distance to a highly reflective tissue interface, such as the sphenoid bone. Further, in embodiments, the processing unit may display the amplitudes of the ultrasound units on a display. In embodiments, the processing unit may display images indicating the location of the anatomical features, for example the SPA.

In embodiments, ultrasound transducers and probes, for examples as disclosed above, may be part of a surgical probe including an ablation element, in particular a cryo-ablation element. FIGS. 17A-17D show views of the distal end of an embodiment of a surgical probe, particularly an ablation probe, comprising an expandable membranous structure which may be used when a target treatment site is located. The ablation probe shown is an example and other cryo-ablation probes, as well as other types of ablation probes, may be used with the disclosed ultrasound technology disclosed herein. The ablation probe is configured with expandable membranous structure functioning as a liquid cryogen evaporation chamber. Liquid cryogen enters the interior of expandable membranous structure. Evaporated cryogen gas exits the interior of expandable membranous structure through fenestration(s) 147 in distal end 146 of probe shaft 145 and exits proximally into the room.

Figure 17A:
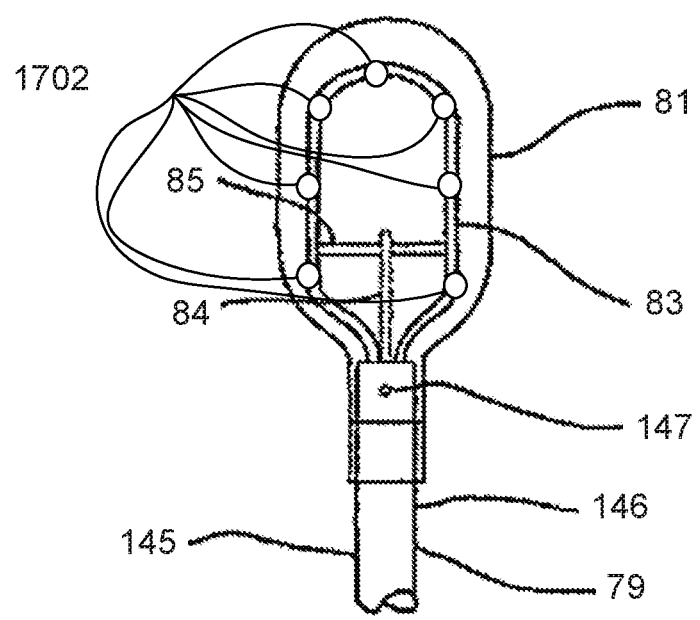
FIGS. 17A-D shows an embodiment of an integrated probe.

As shown in FIG. 17A a structure or member 83 is formed into a looped and elongated structure having arcuate edges for presenting an atraumatic surface. The structure 83 may be formed of a relatively rigid wire or spring like material which maintains its configuration when pressed against a tissue surface. Structure 83 may form a continuous structure which defines an opening there through such as a looped or elongated and looped member which is open through the loop. The structure 83 may be contained entirely within the expandable structure 81 which may be formed to have a predefined shape which is distensible or non-distensible when inflated by the cryogen. Moreover, the expandable structure 81 may be formed to surround the structure 83 entirely without being supported by or attached to the structure 83 itself. Such a structure 83 may provide a configuration which presents a low-profile as the device is advanced into and through the nasal cavity and between the nasal turbinate tissues. Yet because of the relatively flattened shape and rigidity and integrity of the structure 83, the structure 83 may be used to manipulate, move, or otherwise part the tissues of the nasal cavity without having to rely upon the expandable structure 81. Additionally, the low-profile enables the structure 83 to be positioned desirably within the narrowed confines of e.g., the cul-de-sac in proximity to the posterior nasal nerves. When the expandable structure 81 is in its deflated state, it may form a flattened shape and when inflated, the expandable structure 81 may inflate into a configuration which remains unsupported by or attached to the structure 83. Because the structure 83 may be formed of a member which solid along its length, the cryogen may be introduced directly into the expandable structure 81 through a distal opening defined in the probe shaft 145.

In embodiments, structure 83 may be formed of a hollow tubular member which itself is formed into the continuous or looped shape. In such an embodiment, the cryogen may be optionally introduced through the hollow tubular member and dispersed within the interior of the expandable structure 81 through one or more openings which may be defined along the tubular member. In yet another alternative, the structure 83 may be formed into a flattened shape rather than a looped shape. In this configuration, the structure may be either solid or hollow such that that cryogen may be introduced through the structure and into the interior of the expandable structure 81 via one or more openings defined along the structure.

The structure 83 may extend and remain attached to the probe shaft 145, but the remainder of the structure 83 which extends within the expandable structure 81 may remain unattached or unconnected to any portion of the expandable structure 81. Hence, once the expandable structure 81 is inflated by the cryogen, the structure 83 may be adjusted in position or moved via manipulating the probe shaft 145 relative to the interior of the expandable structure 81 to enable the targeted positioning and cooling of the tissue region when in contact against the outer surface of the expandable structure 81. For instance, the structure 83 may press laterally upon a particular region of the underlying tissue to stretch or thin out the contacted tissue region to facilitate the cryogenic treatment. When the structure 83 is adjusted in position relative to the expandable structure 81, the expandable structure 81 may remain in a static position against a contacted tissue region allowing for limited repositioning of the structure 83 within.

In embodiments, the structure 83 may be attached along the interior of the expandable structure 81 partially at particular portions of the structure 83 or along the entirety of the structure 83. For instance, structure 83 may be attached, adhered, or otherwise coupled over its entirety to expandable structure 81 while in other variations, a distal portion of structure 83 may be attached, adhered, or otherwise coupled to a distal portion of the expandable structure 81 while in yet other variations, portions of the structure 83 may be attached, adhered, or otherwise coupled to the expandable structure 81 along its side portions. Any of these variations may be optionally utilized depending upon the desired interaction and treatment between the structure 83, expandable structure 81, and underlying tissue region to be treated.

In embodiments, the lumen 84 for introducing the cryogen into the interior of the expandable structure 81 may be extended past the distal end of the probe shaft such that the cryogen is released, within the interior at a more distal location. As shown, the cryogen lumen 84 may be supported along the structure 83, e.g., via a bar or member 85 which extends across the structure 83. This particular variation may allow for the cryogen to be introduced into the distal portion of the interior of the expandable member 81. Either this variation or the variation where the cryogen is released from an opening of the probe shaft may be utilized as desired.

Figure 17B:
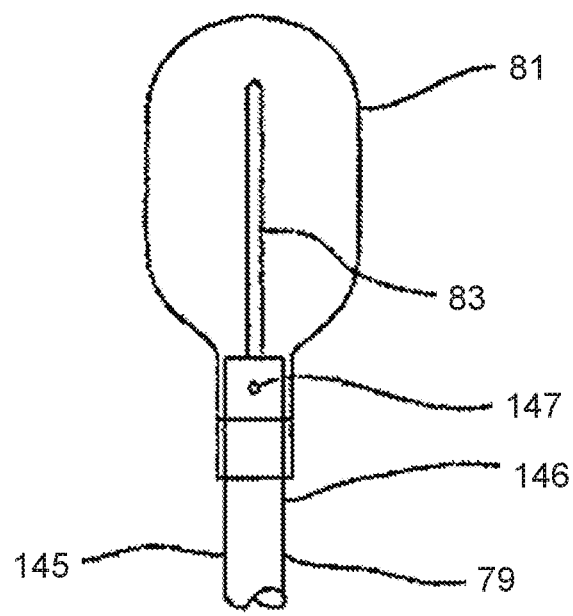
Figure 17C:
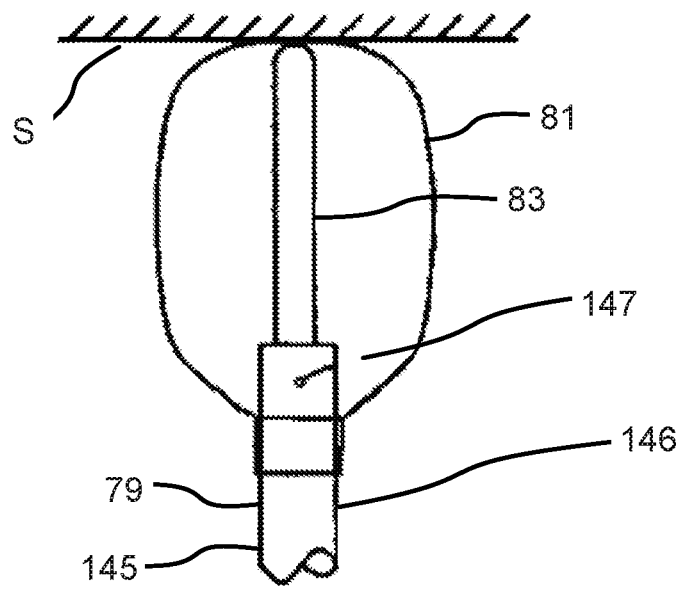
Figure 17D:
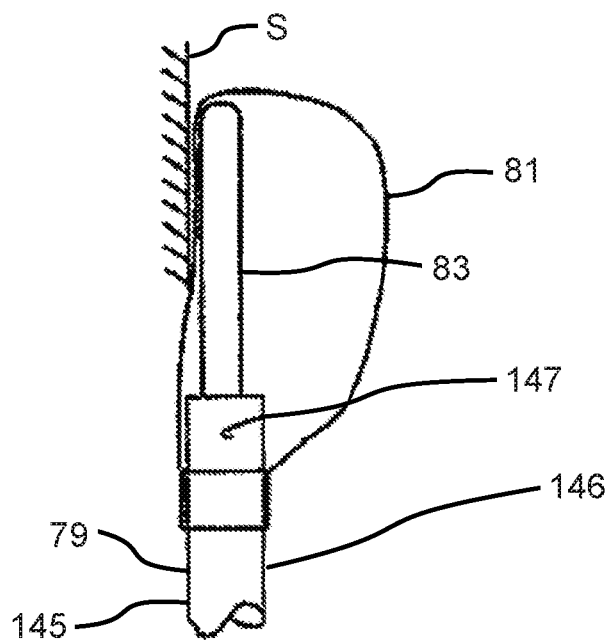

FIG. 17B shows a side view of the embodiment of FIG. 17A illustrating how the structure 83 can be formed from a relatively flattened configuration relative to the inflated expandable structure 81. Because of the structural integrity of structure 83 and its relatively flattened profile, the structure 83 may provide for targeted treatment of the tissue when contacted by the device. FIG. 17C shows the side view of the inflated expandable structure 81 when pressed in a longitudinal direction by its distal tip against the underlying tissue surface S. The relative strength of the structure 83 provides for the ability to press the device against the tissue surface such that the remainder of the expandable structure 81 may maintain its inflated configuration to potentially insulate the other surrounding tissue regions. FIG. 17D likewise shows the device when the structure 83 is pressed laterally along its side against the tissue surface S such that the structure 83 lies flat. The contacted tissue region may be treated while the remainder of the surrounding tissue is potentially insulated by the expanded structure 81. Further exemplary ablation devices for use with the present invention are described in U.S. Ser. No. 14/503,060 filed Sep. 30, 2014 and U.S. 62/408,920 filed Oct. 17, 2016, the contents of which are incorporated herein by reference in their entirety for all purposes.

Figure 18:
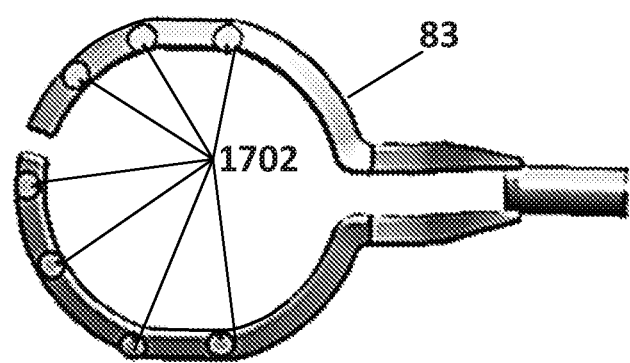
FIG. 18 shows an embodiment of an integrated probe.

In embodiments ultrasound transducers may be attached to a support member within a balloon as shown in FIG. 17A. In embodiments this balloon may be selectively filled and drained with an acoustic coupling agent such as a gel or a fluid. In embodiments, the balloon is filled with fluid to allow for better acoustic coupling during ultrasonic sensing and positioning, then drained of fluid once the device is in place and ablation is desired to be performed, for example by releasing a cryogen into the area encompassed by the balloon. In embodiments, ultrasound transducers 1702 are mounted on a loop-like support structure 83 that is shown in FIG. 17A and in FIG. 18A-C and may be used to scan tissue within the nasal cavity, as discussed herein.

Figure 19:
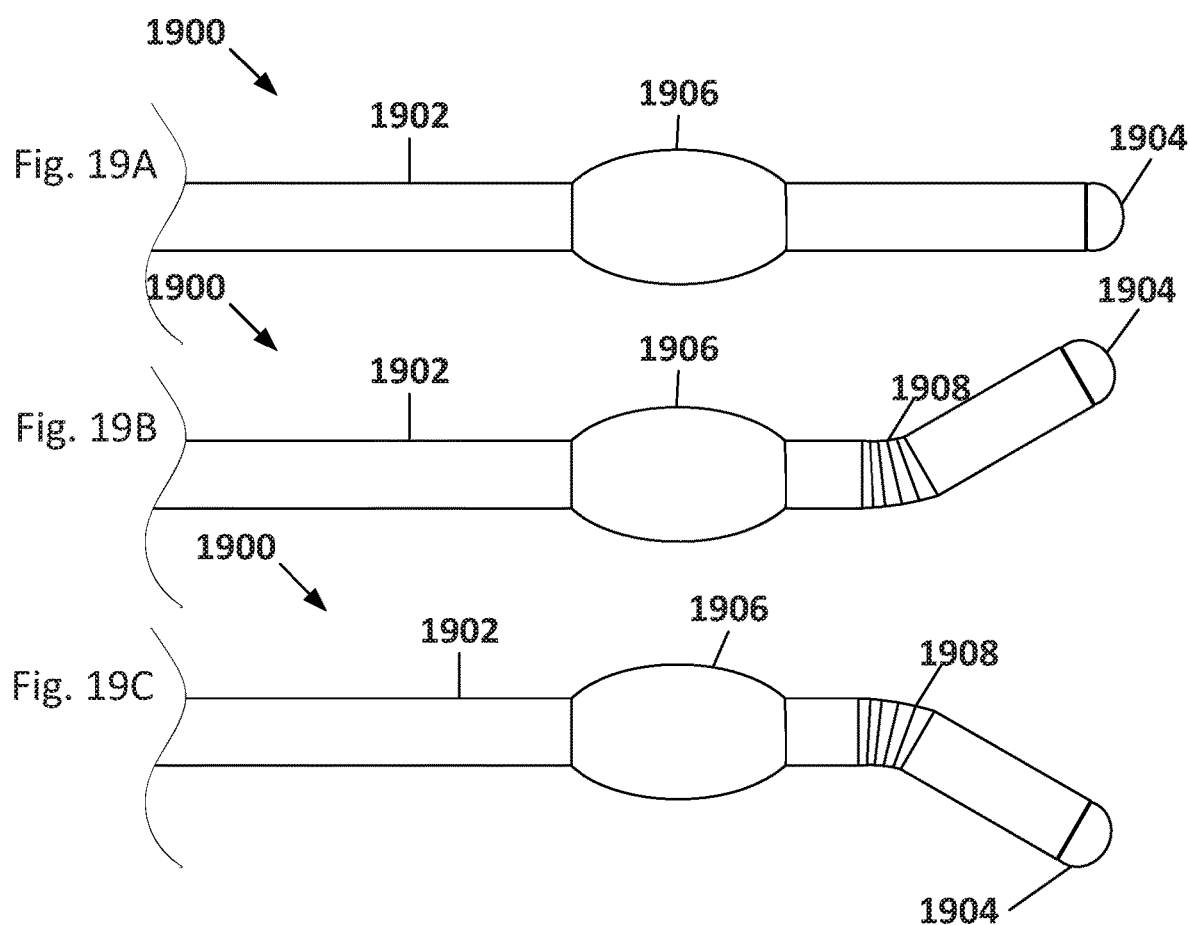
FIGS. 19A-C show embodiments of integrated probes.

In embodiments, an ultrasound probe and an ablation probe may be integrated into a single probe with a single shaft. For example, as shown in FIG. 19A a shaft 1902 of a probe 1900 may include an ultrasound transducer 1904 at the distal end and an ablation element portion 1906, for example a cryo-balloon along the shaft of the probe. In embodiments, for example as shown FIGS. 19B and 19C, the shafts may include articulation joints 1908, which may be used to perform scans with the ultrasound probe while the cryo-ablation elements remains stationary of is required to move less relative to the ultrasound transducer.

Figure 20:
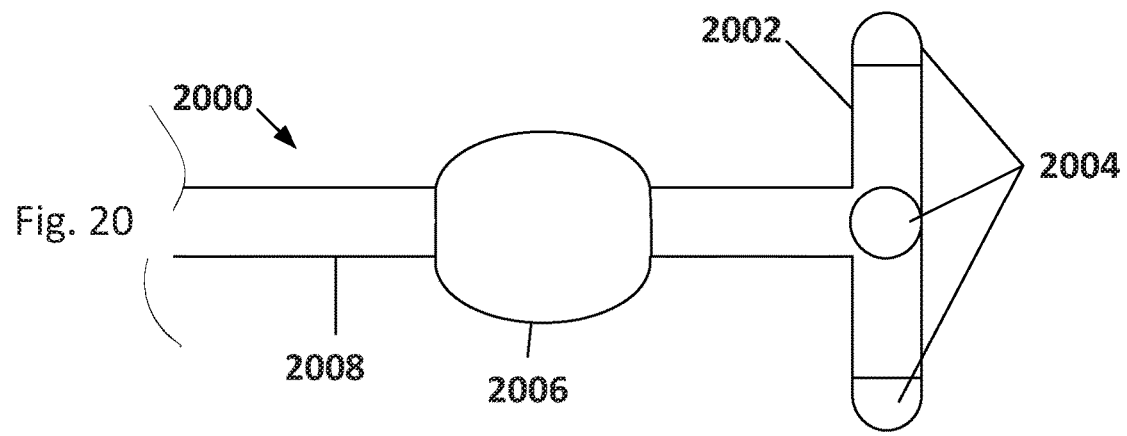
FIGS. 20-22 show embodiments of integrated probes.
Figure 21:
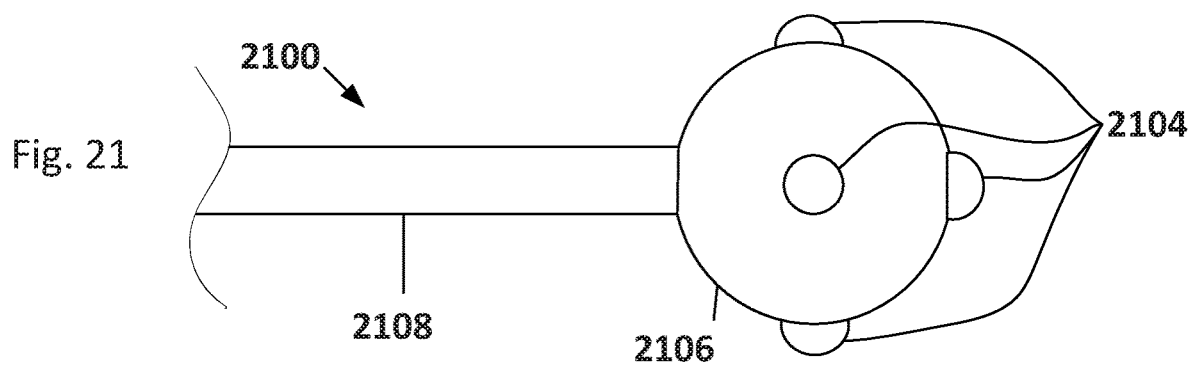
Figure 22:
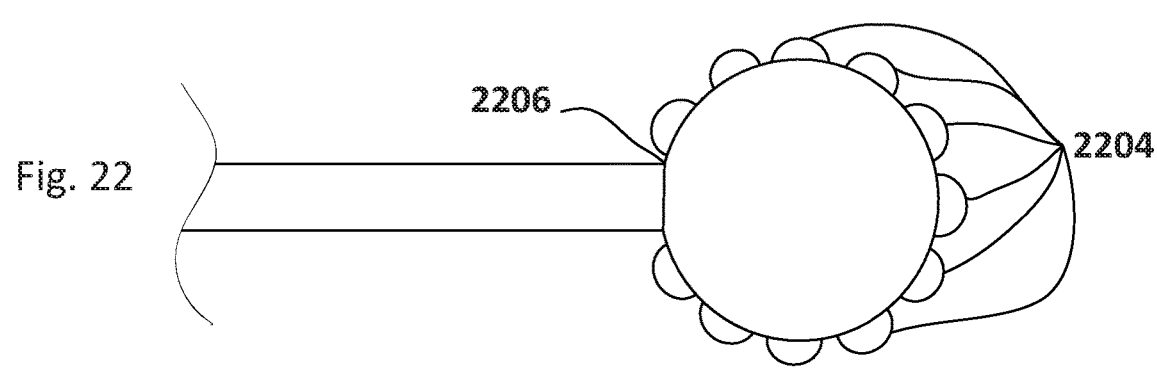

In embodiments, an integrated probe may include a plurality of ultrasound transducers, which are used to locate an anatomical features, such as the SPA or a bony landmark, as disclosed above. The ultrasound transducers may be positioned at any position along the longitudinal shaft of the probe, the cryo-ablation element, or an auxiliary shaft including a crossbar. For example, as shown in FIG. 20, an integrated probe 2000 includes a crossbar 2002 with three sets of ultrasound transducers 2004 at the distal end, and an ablation member 2006 along the shaft 2008. Further, in embodiments ultrasound transducers may be attached to the balloon of the cryo-ablation element. For example, as shown in FIG. 21, a balloon 2106 at the distal end of a shaft 2108 of a probe 2100 may include an ultrasound transducer 2104 at the distal end and ultrasound transducers 2104 along a perimeter around the longitudinal axis of the probe shaft. As a further example, as shown in FIG. 22, a balloon 2206 may include ultrasound 2204 transducers along a planar perimeter around an axis which is perpendicular to the longitudinal axis of the probe shaft. FIGS. 21 and 22 show ultrasound transducers mounted to an exterior surface of a balloon, however in embodiments one or more or all of the ultrasound transducers may be mounted to the interior surface of a balloon, or are otherwise encompassed within the balloon's interior. An advantage of positioning ultrasound transducers in the interior of a balloon is the ability to use additional acoustic coupling mechanisms, such as those described elsewhere in this disclosure.

As disclosed above, multiple ultrasound units may be used by a processing unit to more precisely and/or more quickly locate the SPA or other vessels or anatomical features. For example, the processing unit may acquire a signal from each independent ultrasound unit and analyze the signals to generate directional information regarding the position of the SPA relative to the cryo-ablation element. In embodiments, the signals from individual ultrasound transducers may be combined or averaged prior to processing. For example, during A-mode scanning or B-mode imaging, a multi-element transmit and receive array may provide benefits including the improvement of lateral image resolution.

When a target treatment site is determined based on a correlation with the location of a detected anatomical feature with the one or more ultrasound transducers of an integrated probe, the probe may be positioned at the target treatment site and ablation of the PNN to treat rhinitis may be performed. In embodiments, the detection of the anatomical features, for example the SPA, may continually be performed before and/or during the ablation to provide the advantage of real time target treatment site detection relative to the probe while ablation is being performed.

Figure 23A:
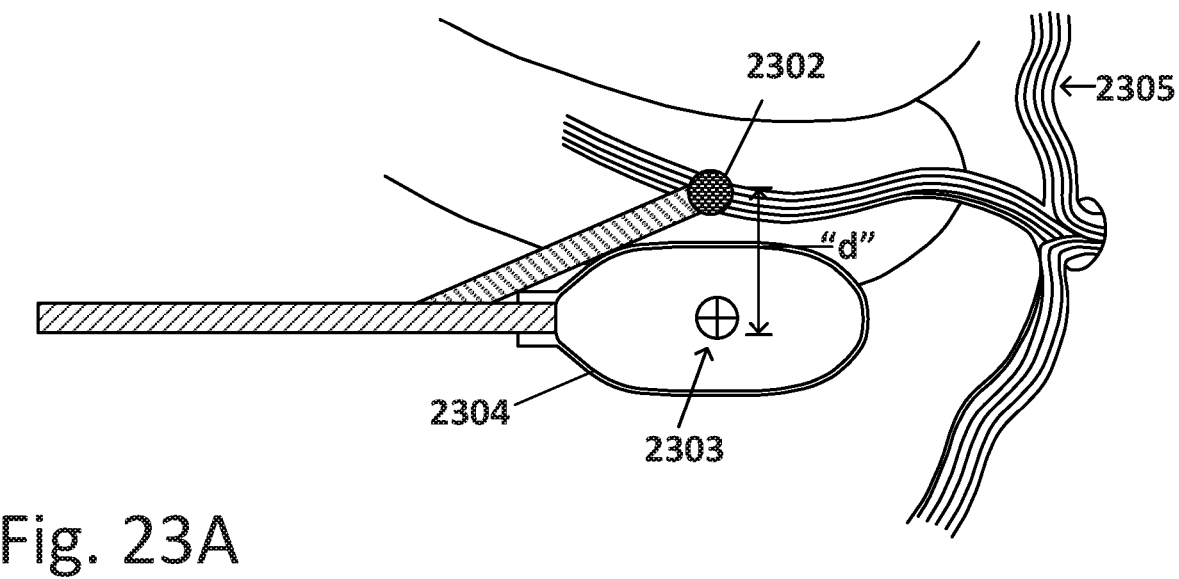
FIGS. 23A-D show embodiments of integrated probes with a fixed distance between an ultrasound transducer and cryo-ablation element.
Figure 23B:
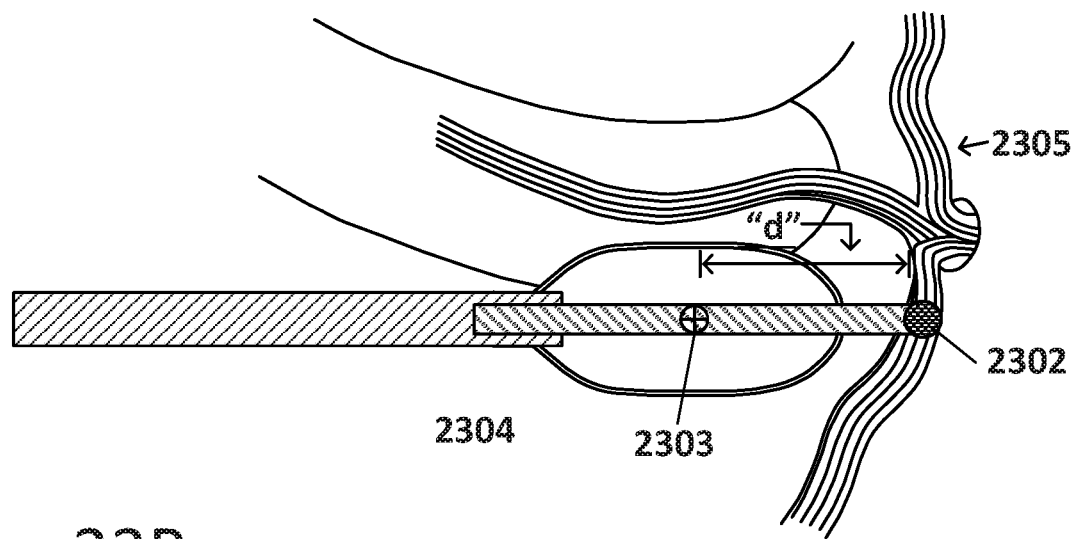
Figure 23C:
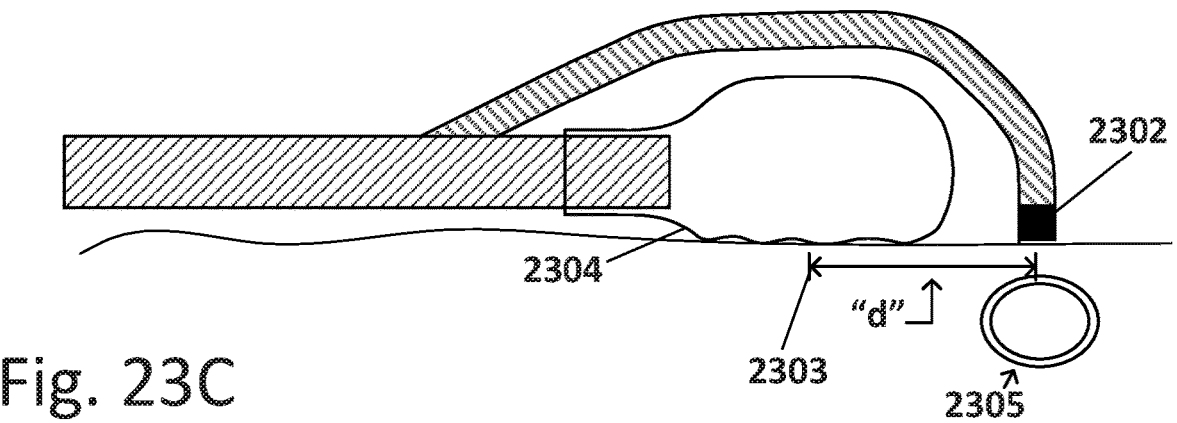
Figure 23D:
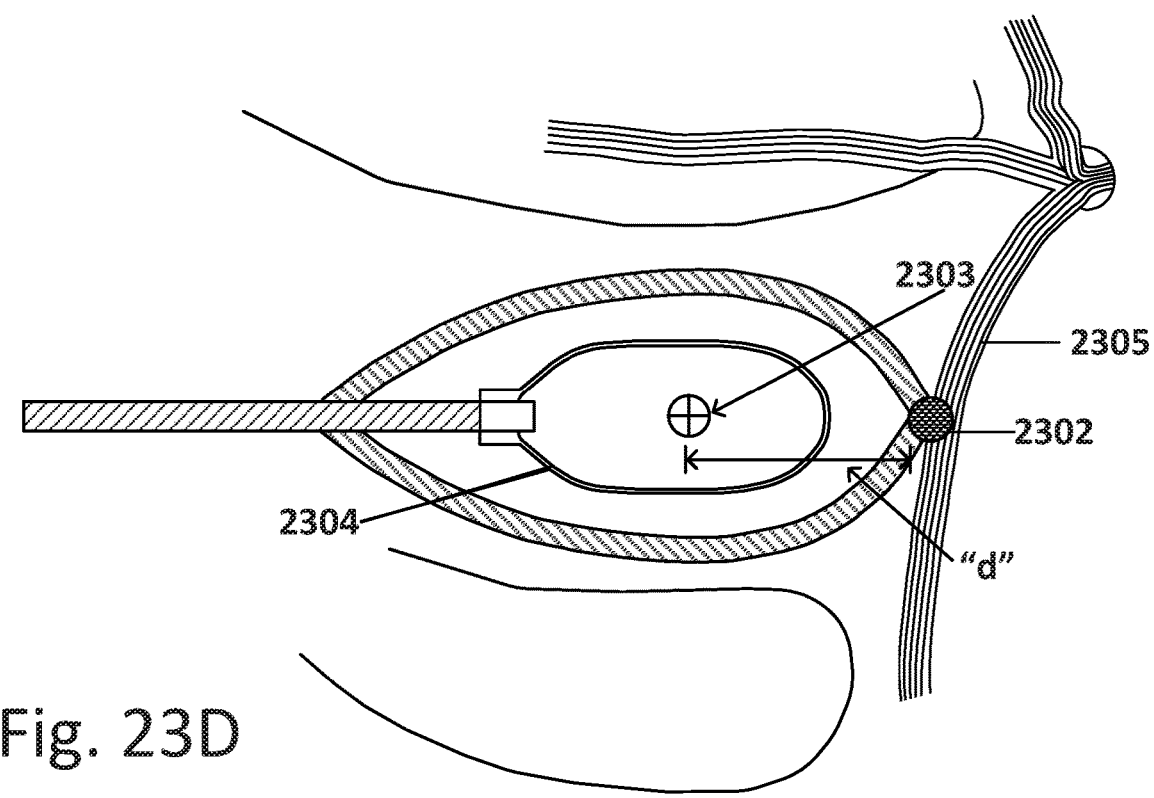

In embodiments, for example as shown in FIG. 23A an ultrasound transducer 2302 may be offset from the center 2303 of the cryo-ablation element 2304 and epicenter of ablation so that ablation may be performed when the ultrasound transducer is positioned above a blood vessel 2305, for example the SPA, and therefore prevent direct treatment of the SPA. For example, the ultrasound transducer may be offset by a distance "d" from the center of the ablation probe and treatment epicenter, wherein the distance corresponds to a distance between a blood vessel to be avoided and a nerve to be treated. The ultrasound transducer 2302 may be offset in a lateral orientation, as shown in FIG. 23A, or a distal orientation as shown in the FIGS. 23B-23D. During an ablation procedure, the surgical probe may be advanced into the nasal cavity and the offset ultrasound transducer may scan tissue, as disclosed above, in order to locate a blood vessel. With the transducer over the blood vessel, for example the SPA as shown in FIGS. 23A-D, the cryo-ablation element will not be over the SPA. With the ultrasound transducer held stationary and continuing to detect blood flow of the SPA, cryo-ablation is performed with the assurance that the SPA is not at the epicenter of the ablation zone and will not receive direct treatment.

In embodiments utilizing an integrated ultrasound and ablation surgical probe, the relative position of the ultrasound transducer with respect to the ablation probe may be fixed or may be variable. In embodiments with a variable distance between the ultrasound transducer and the cryo-ablation element, the distance at any time may be measured for example with a sensor, and used by a control system to alter ablation parameters. In embodiments, the probe may provide an indication if the detected variable distance is not large enough to avoid tissue damage in the region of the SPA.

Figure 24A:
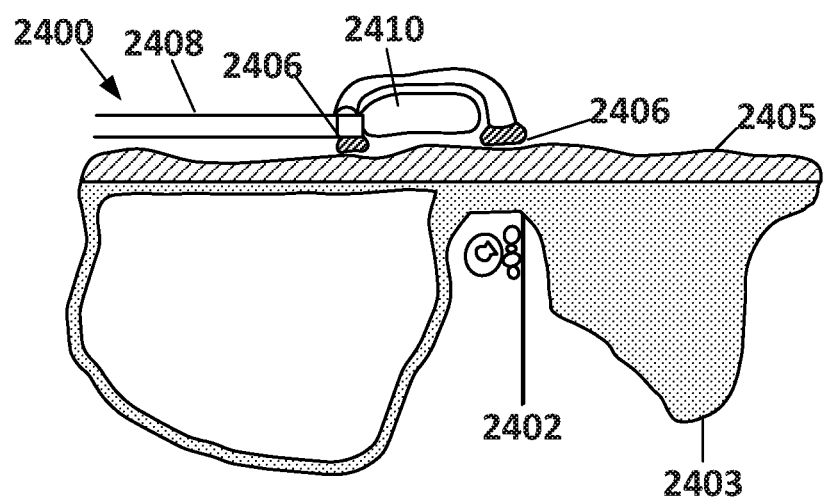
FIGS. 24A-B show embodiments of integrated probes used to detect bone thickness.
Figure 24B:
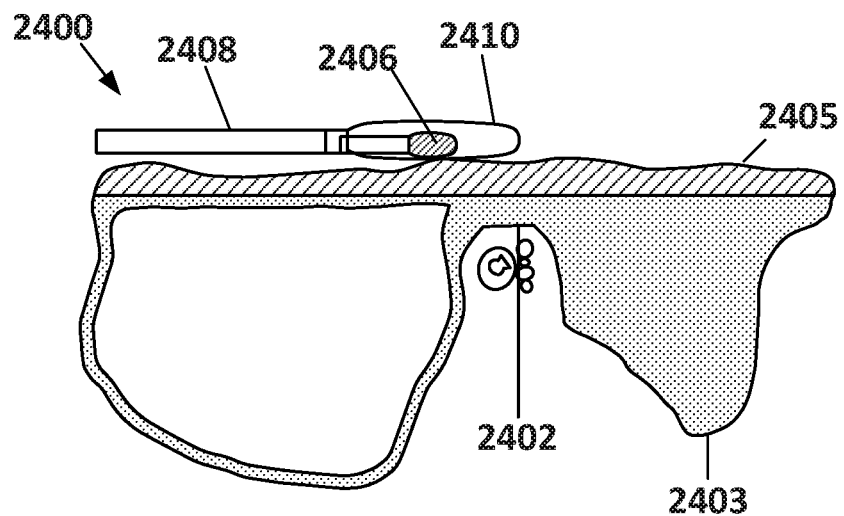

FIGS. 24A and 24B show embodiments of combined ablation and ultrasound sensing probes 2400 configured to interrogate the posterior fontanelle, palatine bone 2402 and sphenoid bone 2403 and surrounding tissues. As disclose above, A-mode ultrasound scans may reflect signals that allow for differentiation between different thicknesses of mucosal tissue, bones, and bone and cartilage boundaries. For example, differentiation between thin cartilage of the fontanelle and thin palatine and/or thick sphenoid bone may be detected. One way in which the signals may differ may be in the amplitude of reflected signal. In embodiments, a plurality of ultrasound transducers 2406 may be coupled to the probe shaft 2408 both more distal of the cryo-ablation element 2410 and more proximal of the cryo-ablation element 2410, for example as shown in FIG. 24A. The two ultrasound transducers may be used to detect anatomical features on either side of the cryo-ablation element. For example, the ultrasound transducers may be used to detect different thicknesses or composition of tissue 2405 corresponding to a target treatment site of a nerve. To detect this difference the probe 2400 is advanced into the nasal cavity and scanned along tissue within the nasal cavity until the distal transducer detects a signal characteristic of one tissue configuration and the proximal transducer detects a signal characteristic of a different tissue configuration. For example, in locating the transition between the thin palatine and thick sphenoid bones, the device is advanced to the point at which the distal transducer(s) detects a reflected signal characteristic of thick bone while the proximal transducer(s) detects a reflected signal characteristic of thin bone or cartilage. Once this position is determined, the operator will have increased confidence regarding how deep within the nasal cavity the ablation probe is located, and from that point can further maneuver the probe, as needed, into the desired region for treatment (for example, in the region of the PNN) and initiate ablation. In embodiments, probe 2400 may be used to detect mucosal thicknesses to determine dosing timing. For example, tissue around the treatment area may be 1-5 mm thick. If the tissue is less than 3 mm thick the flowrate or discharge time of the cryogenic liquid that evaporates in the cryo-ablation element may be reduced to ensure ablation does not penetrate too deep and damage tissue that it not in the target treatment area. In embodiments, bone/soft tissue changes are used as indicators for the location of a treatment site. The transition of 0.5-1 mm thick cartilage to 1-3 mm thick bone may indicate that the probe has reached the perpendicular plate of the palatine bone where the nerves innervate the nasal cavity and this transition may be used to determine the target treatment site. In embodiments, a bone to bone transition between the palatine and the sphenoid bone may be detected by a transition from 1-3 mm of bone thickness to >4 mm of bone thickness. In embodiments, the location of the palatine canal may be determined in order to avoid treatment to nerves within the palatine canal. In embodiments, for example as shown in FIG. 24B, a single ultrasound transistor 2406 of a probe 2400 may be used to detect bone and tissue thicknesses and transitions as discussed in relation to FIG. 24A.

Figure 25A:
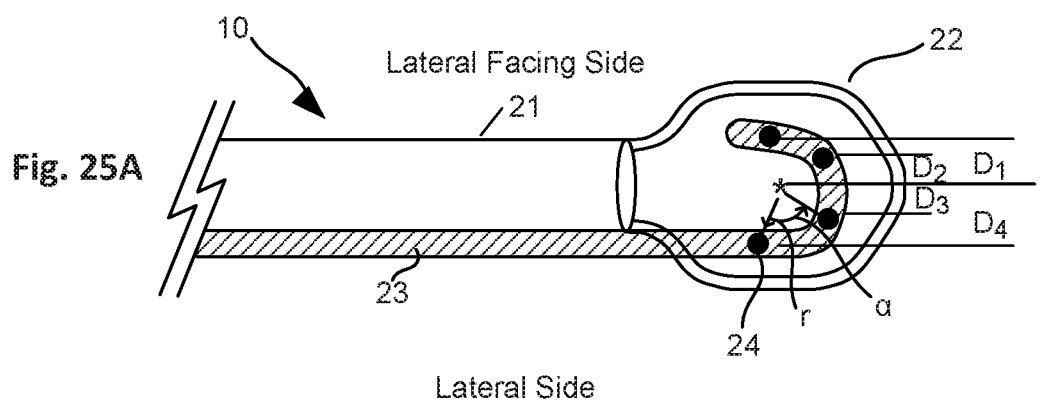
FIGS. 25A-C show embodiments of integrated probes.
Figure 25B:
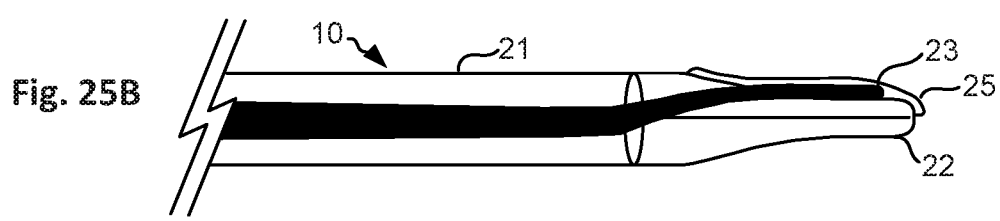
Figure 25C:
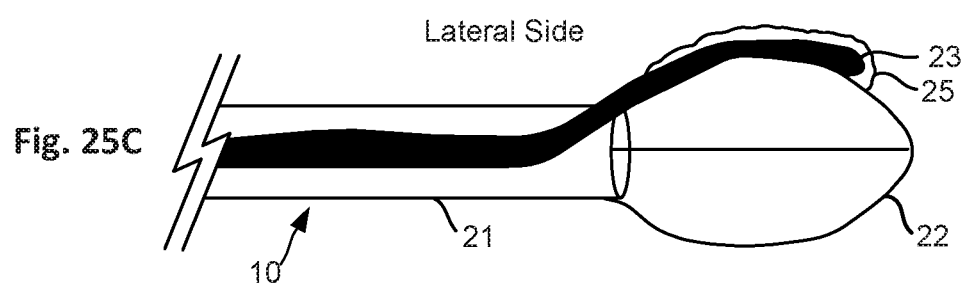

In embodiments, for example as shown in FIG. 25A-C, the ultrasound transducers 24 are configured in an array on the lateral side of the ablation probe positioned a distance r from the epicenter of ablation zone and an angle α away from each other to define an area within the ablation zone that if arteries are identified within this region the device provides a notification not to ablate or will prevent ablation from being initiated. The radius can be defined between 1-8 mm, preferably 6 mm. The angle between the transducers can be 5-180 deg. preferably 45-90 deg. The number of transducers can be 2-10. FIG. 25A illustrates the lateral face of the embodiment. Probe 10 comprises of an integrated sensing element 23 with ultrasound transducers 24 embedded and an ablation element 22 affixed to a cannula 21. The sensing element 23 is affixed to bottom or top of the cannula 21 in line with the vertical axis of the lateral plane to keep the profile in the horizontal axis as low as possible. Electrical or flex circuitry runs the length of the cannula from the ultrasound sensors to a controller inside a hand piece or box. FIG. 25B shows a top view of probe 10 in the collapsed configuration. Before inserting the probe into the nasal cavity, a coat of a gel like substance 23 lubricates at least the lateral side of the probe around the transducers to create an acoustic friendly environment and make translation on the mucosa easier. This configuration is designed to allow the user to advance the probe in to the nasal cavity and position the ablation element 22 in the target area. Once the probe 10 is in the region of the target area, for example the posterior ⅓ of the middle meatus, the ablation element 22 is expanded to press the transducers 24 onto the lateral wall of the nasal cavity. FIG. 25C shows an expanded state of probe 10. Once the transducers are in contact with the wall, an indication is provided the ablation probe is appropriately placed and free of main branches of the SPA by an audible, visual or tactile signal. If a visible indicator is used, the indicator will be affixed along cannula 21 so it can be visualized within the nasal cavity using the rigid endoscope that is being used to visualize the target area. If placement is correct and safe, the embodiment will inform the user and the user will activate ablation. If there is an artery detected, the probe will inform the user and ablation may not be allowed to activate. In this case, the user will translate anterior or posterior until the ablation element is free of vasculature and the user will be informed and ablation will be allowed.

Figure 26A:
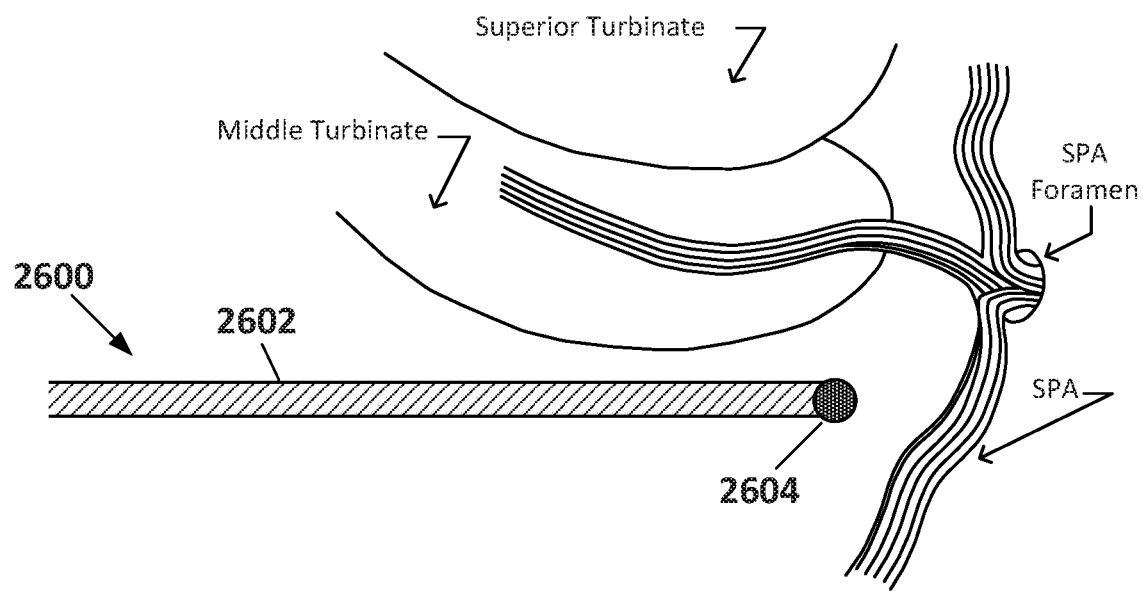
FIGS. 26A-D show an embodiments of an integrated probe with slidably coupled cryo-ablation element.
Figure 26B:
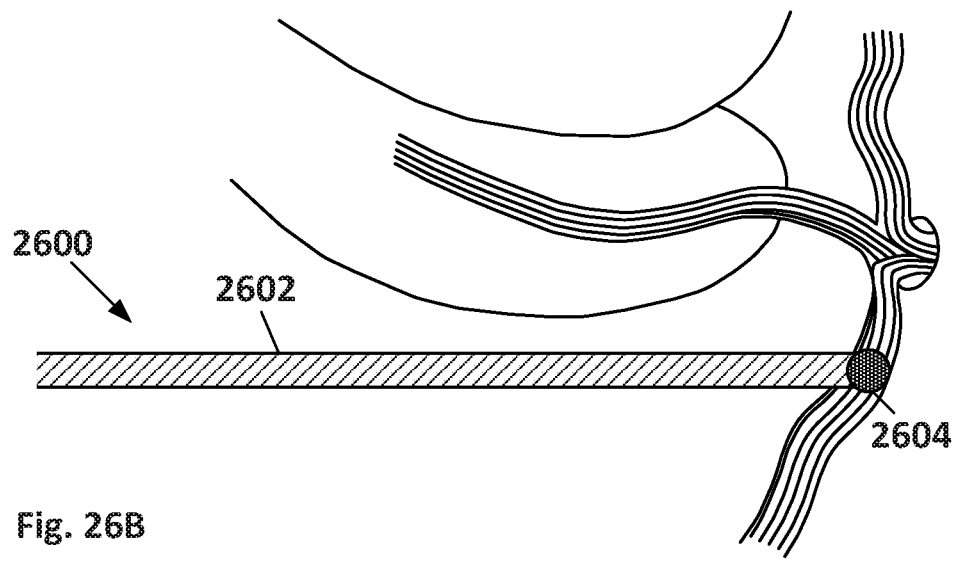
Figure 26C:
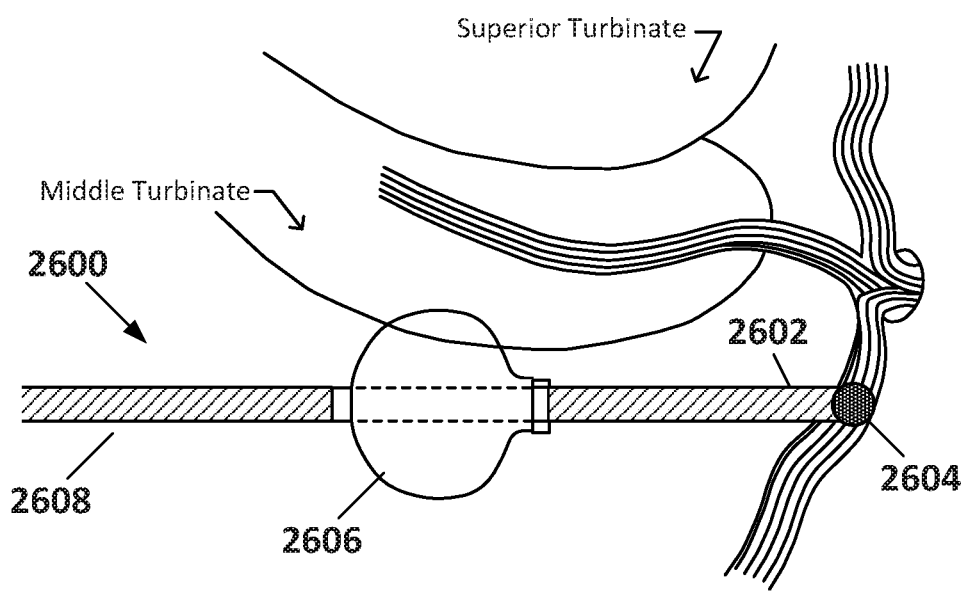
Figure 26D:
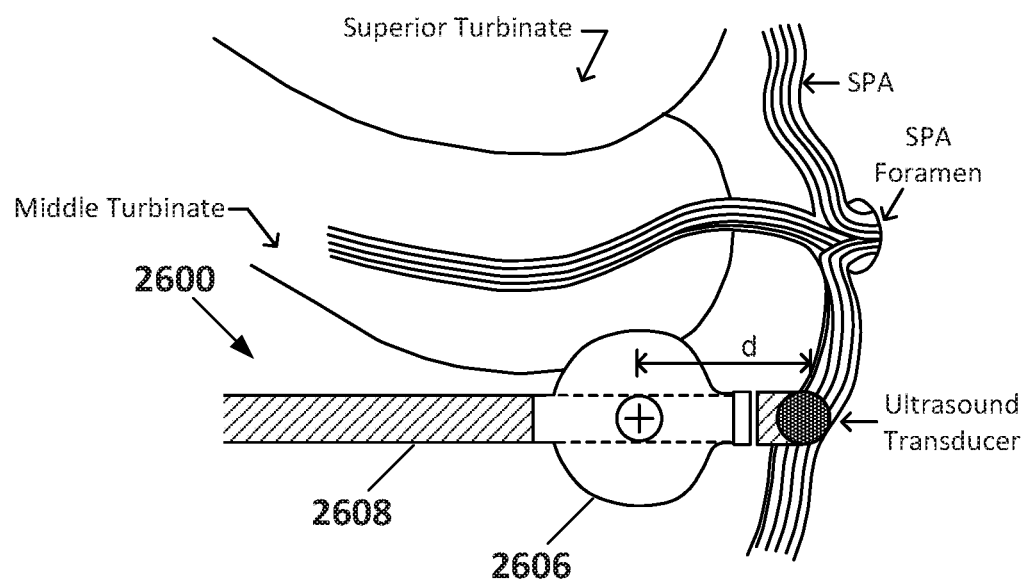

In embodiments, a cryo-ablation element may be slideably coupled to the probe shaft of an ultrasound probe, for examples as shown in FIGS. 26A-D. As shown in FIG. 26A, ultrasound probe 2600 comprises a shaft 2602 with an ultrasound transducer 2604 disposed at the distal end. The ultrasound probe 2600 may be inserted into the nasal cavity with the cryo-ablation element 2606 remaining outside of the nasal cavity. With the ultrasound probe 2600 within the nasal cavity, the ultrasound transducer 2604 may be swept along tissue within the nasal cavity in order to detect an anatomical features, for example a blood vessel or anatomical features (e.g. tissue thickness, bone thickness, transition/boundary) as discussed above. A target treatment area may be determined based on the determined location of the anatomical feature. For example as shown in FIG. 26B, the anatomical feature may be the SPA and the target treatment site may be determined to be a predefined distance from the SPA corresponding to the distance between the SPA and the PNN. With the ultrasound transducer 2604 held against the SPA, as cryo-ablation element 2608 is advanced along the shaft 2602 of the ultrasound probe, for example as shown in FIG. 26C. In embodiments, the cryo-ablation element may be advanced through a lumen in the ultrasound probe or may use the shaft of the ultrasound probe as a rail. For example, a cryo-ablation element 2606 is coupled to shaft 2608, both of which have a lumen that surrounds and slides over shaft 2602 As shown in FIG. 26C, the cryo-ablation element may comprise an inflatable structure with a lumen that surrounds and slides along the shaft of the ultrasound probe. As shown in FIG. 26D, the cryo-ablation element 2606 may be advanced to the predetermined distance "d" from the ultrasound transducer and ablation may be performed at the target treatment site. In embodiments the ultrasound probe may be configured like a flexible or rigid guide wire over which the ablation probe may be introduced to the ablation site. Using the ultrasound probe as a guide for the slidable cryo-ablation element is advantageous since it allows for the target treatment site to be located with a small device, and further allows the cryo-ablation probe to reach the target treatment site more precisely compared to an unguided device.

In embodiments, the sensing or combined ablation and sensing probe may contain stabilization elements. Relative tissue/transducer motion that is parallel to the angle of ultrasound transmission but unrelated to blood flow may add unwanted noise to or confound Doppler measurements. For example, slight shifts in probe position, for instance those arising from an unsteady hand of an operator holding the probe, occurring while measurements are being made may create a Doppler-type effect. This could reduce performance for locating the SPA and as such extend procedure time or lead to errors in determining the proper location of treatment. In embodiments, an inflatable balloon may be attached to the shaft of the probe and used to stabilize the ultrasound transducer while ultrasound scans are performed. When a Doppler scan is to be performed the balloon inflates and applies transient pressure against nearby structures as a way to stabilize the position of the probe relative to surrounding tissues, thus reducing motion unrelated to blood flow and increasing the accuracy of the Doppler signal. The balloon may be deflated when it is desired to reposition the probe. The balloon may be re-inflated when additional Doppler measurements are taken. For some Doppler measurements, for example when the ultrasound probe is traversing the nasal cavity quickly in a "scanning mode" where accuracy is less important than general information, the stabilization balloon may not be inflated. In embodiments, a single stabilization balloon is utilized. In embodiments, multiple balloons may be used, for example a stabilization balloon located on either side of the ultrasound transducer. In embodiments with a plurality of transducers, a plurality of balloons may be proximate to some or all of these transducers. In embodiments, the balloons may encompass the ultrasound transducers. In embodiments, the transducers may be attached to the exterior of the balloons. In addition to balloons, stabilization mechanisms may also include suction, coiling, and tines extending from the probe employed to stabilize probe position.

In embodiments, the quality of acoustic coupling between the ultrasound transducer and tissue is important for achieving accurate measurements for all modes of ultrasound. Without proper acoustic coupling, large reflections at the transducer/air interface essentially prevent ultrasound waves from reaching tissues. One mechanism for ensuring quality acoustic coupling is to place the ultrasound transducer directly in contact with tissue so that there is no air gap. To aid in ensuring sufficient contact, suction may be employed. A lumen may be incorporated through the shaft of an ultrasound probe containing one or more ultrasound transducers. Air may be pushed or pulled through this lumen. One or more openings may be placed at the distal end of the probe in proximity to the ultrasound transducer. When the ultrasound transducer is brought in proximity with tissue, suction may be applied to the openings near the transducer and that suction may draw the transducer more closely to the tissue until the openings make contact with the tissue and lock the device in place. Suction may be maintained during ultrasound measurements to ensure sufficient contact for quality energy coupling and signal transmission across the tissue-transducer interface. Ablation is also dependent upon contact between the ablation member and the tissue surface. The system and methods described above may be used where the openings are in proximity to the ablation member and where suction is applied to make sufficient contact during treatment.

In embodiments, ultrasound signals from during a cryo-ablation treatment may be analyzed by the processing unit to determine if the mucosa or a blood vessel, for example the SPA, is being damaged during treatment. For example, blood flow through the SPA during ablation may be monitored, and the detected blood flow may be used to determine the duration of the ablation. If the blood flood is detected to be reduced below a preset threshold the ablation may be terminated. In embodiments, the target ablation sites may be immediately adjacent to the determined location of the SPA, for example 1-5 mm, in order to avoid freezing directly over the SPA.

Embodiments further include systems and methods for assessing the effect of a treatment performed in the nasal cavity. For example, the effect of a chemical or pharmacologic intervention, such as the application of a steroid, antibiotic, or other substance can be assessed using ultrasound scans as disclosed herein. Embodiments are also used to assess the impact of mechanical interventions, including artery ligation, neuromodification procedures such as neurectomy, neuroablation, and/or selective postganglionic pterygopalatine parasympathectomy (SP3), and other tissue remodeling procedures such as turbinate reduction. In embodiments assessments are made as stand-alone single session evaluations. In embodiments the assessments are the result of comparison of evaluations obtained before and after an intervention has taken place. In embodiments, comparisons are made using evaluations captured after a period of time has elapsed following an intervention, allowing time for full therapeutic effect to be achieved and for the resolution of any acute post-procedure effects such as swelling or inflammation. In embodiments this period of elapsed time is 7-30 days following an intervention. In embodiments, comparisons are made using evaluations captured immediately or nearly immediately following an intervention, for example 5-30 minutes following an intervention.

Embodiments include the use of an ultrasound transducer connected to the shaft of a catheter or probe and inserted into the nasal cavity. The transducer may be a single element transducer or an array of multiple or many elements (for example, up to 72 elements). The transducer may be configured to operate in A-mode, M-Mode, Doppler mode(s), and/or B-mode (for embodiments involving transducer arrays only). Processing techniques, such as elastography imaging or assessments involving spectral analysis, may be implemented in some embodiments.

In embodiments an assessed parameter includes the thickness of mucosal tissue in the nasal cavity. Comparisons may be made between mucosal thickness evaluated before and after an intervention in order to assess the effect of the intervention.

Ultrasound waves emitted from a transducer will be scattered, absorbed, and reflected by tissues. The degree of reflection will be largely governed by changes in the acoustic impedance of tissue that a traveling wave encounters. Bone (and cartilage) and mucosal tissue have large differences in acoustic impedance, and large amplitude ultrasound wave reflections will occur at the interface between bone (or cartilage) and mucosal tissue. As such, the transition between mucosal tissue and bone is detectable in ultrasound data. For example, the interface is represented by a large amplitude spike an in A-mode ultrasound trace or as a bright linear region in an M-mode or B-mode ultrasound image. Embodiments will use a transducer operating at a frequency of 8-20 MHz and preferably 12-15 MHz.

The mucosal tissue is soft and may be deformed with pressure applied via an apparatus. As such the thickness of mucosal tissue may be altered through the contact of an ultrasound transducer to the nasal cavity wall. Embodiments will include mechanisms or methodological steps to ensure that each thickness evaluation utilized for comparative purposes is taken with an identical or nearly identical degree of pressure applied to the mucosal surface.

In embodiments the ultrasound transducer is mechanically coupled to a force sensor such as a pressure sensor, force plate, or strain gauge to assist with controlling pressure applied to the mucosal tissue while making tissue thickness measurements. In embodiments one or more pressure sensors are mounted on the tissue contacting face of the transducer. In embodiments one or more pressure sensors are mounted on a probe or catheter shaft adjacent to the transducer. In embodiments the sensors are adapted to send readings along sensor wires located in a lumen of the probe or catheter shaft to a handpiece of the apparatus. Software algorithms interpret signals from the sensor, for example electrical signals from a strain gauge or force plate, and convert the information to a pressure or force.

In embodiments, the actual force or pressure readings are provided to a user. In variation embodiments, the force or pressure readings are not provided to a user, but instead the apparatus provides the user with an indicator that the contact force is within an acceptable range for a valid measurement. For example, the apparatus may provide a visual, audio, or tactile indicator if contact force is too minimal, acceptable, too aggressive, or some combination of these ranges.

In embodiments, contact force or pressure information is not provided to the user in any way. Alternatively, algorithms making mucosal thickness measurements automatically adjust the calculation based upon the contact force. The elastic modulus (Young's modulus) of mucosal tissue is generally known, as is the Poisson ratio and other material properties required to translate a contact force to an estimated longitudinal strain. As such, an embodiment may use ultrasound time of flight algorithms to estimate the thickness of mucosal tissue, then improve this estimate by adjusting the originally calculated thickness by a factor which accounts for deformation due to the contact pressure or force.

In embodiments, contact force is not measured with a sensor, but is controlled via a mechanical means. In embodiments, a spring mechanism is located at or near the tissue-contacting face of the transducer. The spring constant of the spring is selected such that a certain small range of suitable forces will be required to be applied to the mucosal tissue in order for the transducer to make adequate tissue contact.

In embodiments, contact force is controlled by a compliant coupling balloon, for example a balloon comprised of silicone rubber. The balloon may initially be configured in a deflated state for insertion of a catheter or probe into the nasal cavity. When in the desired position to take a measurement, the user may expand the balloon, for example by filling the balloon with a fluid or gel-like substance infused through a lumen in the shaft of the catheter or probe. In one embodiment, a syringe containing a fluid may connect to a luer-type interface on the handpiece of the apparatus, wherein depressing the plunger on the syringe forces the fluid along the lumen of the apparatus and into the balloon, causing it to expand. When the balloon is expanded, it makes contact with mucosal tissue. Due to the compliant nature of the balloon, the shape of the balloon will mold to the shape of the mucosal tissue without applying a force that is sufficient to compress of deform the tissue. In embodiments, the transducer remains a small distance, for example 1-5 mm, away from the mucosal wall to ensure no contact force is applied. The fluid or gel used to expand the balloon provides sufficient acoustic coupling such that the ultrasound waves may appropriately interrogate the mucosal tissue.

In embodiments, the apparatus includes a mechanism to collapse the balloon by removing the fluid or gel, thus allowing for the distal portion of the apparatus to return to its original slimmer profile which will facilitate removal from the nasal cavity. Fluid or gel can be removed by applying a vacuum or suction to the port on the apparatus handpiece that had previously been used to convey the fluid or gel into the balloon. With the application of negative pressure, the fluid or gel will be drawn back through the delivery lumen towards the handpiece and allow for the balloon to collapse. In embodiments, multiple lumens are used for delivery and/or removal of fluid or gel to/from the balloon.

In embodiments where the transducer is positioned a small distance from the leading edge of the mucosa, for example in embodiments that utilize a coupling balloon, algorithms to determine mucosal thickness may be refined to address additional echoes originating from the interface between the fluid/gel/balloon-mucosa boundary. The difference in acoustic impedance at this boundary is expected to be much lower than the difference at the mucosa-bone/cartilage boundary, and as such the reflection will be of relatively smaller amplitude and easily discernible from the larger reflection produced at the interface with bone or cartilage. In these embodiments, the mucosal thickness may be estimated using the time difference between the detection of these two spikes in a received ultrasound signal.

The thickness measurement of mucosal tissue are dependent on the angle of incidence of the ultrasound beam. For a given region of mucosa, an orthogonally-aligned transducer produces a thickness estimate that is smaller relative to an estimate in the same region when the transducer is obliquely-aligned (and thus has a longer path through the tissue). Though this discrepancy may be controlled for if the incidence angle is known, doing so is expected to be a challenging and low-accuracy task. It is thus desirable to account for the angle of incidence variations in a pro-active manner.

In embodiments, a transducer is mounted on a movable axis, for example on a pivot joint or ball-joint, such that it becomes "self-aligning", for example as shown in FIGS. 28A-D and 29. That is, whenever a transducer is pressed against a surface, the position of the transducer moves along the axis such that it naturally aligns in an orthogonal fashion. In some embodiments, contact sensors, for example electrical impedance sensors or force sensors, may be used at one or more locations on or near the transducer face to ensure orthogonal contact.

In embodiments, transducers are configured to scan through a range of incidence angles. For example, in a phased array, the transmission delay between individual elements is adjusted to steer the resulting ultrasound beam through a number of angles, collecting data at each. Alternatively, in a single element transducer or a transducer comprised of a linear array, the transducer may be mechanically swept through a range of angles, for example from −45 degrees to +45 degrees, collecting data at multiple angles in the range. A number of calculations of mucosal thickness may be made, and the minimum thickness may be selected as the gold-standard measurement that is representative of an orthogonal incidence angle. In embodiments, the maximum thickness may be analyzed, or some combination of the various thickness measurements made at the angles interrogated.

Embodiments may include detection and analysis of echogenicity. One impact of nasal cavity interventions may be a change in the level of edema or fluid in the mucosal tissue. A change in the level of edema, fluid, and/or swelling may be indicative of symptomatic relief and as such indicative of the therapeutic efficacy of an intervention. Changes in these properties of mucosal tissue may be assessed with ultrasound and thereby be useful to physicians and patients. Mucosal assessments may be made with ultrasound by examining the echogenicity of the mucosal tissue. In the present context, echogenicity is a characteristic of tissue that describes how it responds to ultrasound interrogation—i.e. how it absorbs, scatters, and reflects incident ultrasound energy. For example, the brightness (in B-mode) or reflected signal strength (in A-mode) would be indicative of echogenicity. Other tissue characteristics captured by an ultrasound beam—for example speckle texture, spectral energy content, and attenuation constant (inherently linked to the absorption coefficient)—may also be useful for interrogating tissues. It is known by those skilled in the art that changes in tissue edema/water content alter the ultrasonic properties of tissue, for example the speed of sound and the absorption coefficient. In embodiments, one or more ultrasound signals is transmitted into mucosal tissue and the corresponding echoes are received. Received radiofrequency data may be processed in order to extract brightness data, for example algorithms related to quadrature demodulation, envelope detection, rectification, and/or involving the Hilbert transform may be used to better extract brightness data. In embodiments, resulting brightness data is assessed over a window where the mucosa is detected to be (for example, in a region bounded by large reflection spikes that signify balloon/mucosa and mucosa/bone interfaces, respectively). In embodiments collecting two-dimensional B-mode data, brightness data may be assessed across a tissue window that spans both depth and a width determined by the size of the transducer array. In embodiments, comparisons are made between measurements captured before and after a nasal cavity intervention in order to assess a change.

In embodiments, spectral analysis may examine the frequency content of returning echoes to assess changes. For example, a reduction in fluid content in mucosa may change the absorption properties of the tissue in a way that results in a frequency content shift of acoustic backscatter measured by the transducer. In embodiments, received radiofrequency data may be converted into the frequency domain using techniques such as the Fast Fourier Transform (FFT) and analyzed to determine the power density of the frequency content. For example, in the presence of moderate or severe mucosal edema, the attenuation coefficient may be reduced. The attenuation coefficient for ultrasound is frequency dependent, and as such a spectral shift of the power density may occur.

In embodiments, an ultrasound array may be configured to estimate the mechanical properties of tissue using elastography or elasticity imaging, for example vibrational elastography, acoustic radiation force impulse imaging, or shear wave elasticity imaging. As interventions in the nasal cavity may impact the degree or edema or other tissue characteristics that impact the tissue's shear or elastic modulus, mechanical property investigation may yield a practical and valuable way to assess the efficacy of an intervention.

In embodiments, an ultrasound transducer composed of an array of individual elements is mounted on the shaft of a probe or catheter and inserted into the nasal cavity. When in place, an initial ultrasound scan of the area is acquired. Following this, the array is operated in an excitation mode, sending a high intensity focused pulse of ultrasound into mucosa. This pulse displaces tissue in the focal zone using a radiation force and creates a shear wave that will travel away from the excitation site at a speed directly proportional to the shear modulus of the tissue. Following the excitation pulse, the transducer is configured to deliver a series of subsequent tracking pulses in locations adjacent to the location of the excitation pulse. These tracking pulses are similar or identical to standard B-mode ultrasound pulses. Using algorithms that involve speckle-tracking, for example cross-correlation algorithms or phase-shift estimators, these tracking pulses can be utilized to monitor the propagation of the induced shear wave in tissue. By calculating the speed of the shear wave propagation, the shear modulus, and thus ultimately the elastic modulus, of the mucosa may be determined. By comparing measurements of elastic modulus before and after an intervention has taken place, insights into the impact of the intervention may be obtained.

In embodiments that utilize a cryo-ablation probe, ultrasound measurements may be taken during treatment to detect changes in tissue characteristics associated with tissue freezing. These measurements may be used to detect the state of the target tissue. The state of the tissue may be used during treatment to adjust treatment dose parameters including treatment time or the number of freeze-thaw cycles. For example, ice crystals formed during cryo-ablation may increase scattering and/or reflection of ultrasound waves in the treatment region. Using B-mode ultrasound visualization, the proximal edge of a cryo-ablation treated area may appear hyperechoic (bright) with large hypoechoic (dark)

regions more distal from the transducer due to strong reflections at the ice ball interface and associated acoustic shadowing. A change in echogenicity (strength of received echoes) across a region of certain size may signify that treatment is sufficient and that the procedure may end. As an example, an acoustic shadow at least 5 mm wide may be seen as indicative of sufficient freezing. In other examples, different size regions, for example 2 mm or 10 mm wide, may be viewed as more appropriate to signify that sufficient freezing has occurred. In embodiments, these changes are measured using the strength of the signals measured during an A-mode ultrasound scan. One benefit to stopping a treatment at or shortly after sufficient freezing has occurred is that it reduces the risk of unwanted collateral tissue damage in regions outside of the intended treatment area.

In embodiments, transducers are built into the probe shaft to assess the lateral growth of the ice ball created during cryo-ablation. During a cryo-ablation treatment, the cryo-ablation element freezes a region of the mucosal tissue to form an ice-ball that may be ellipsoidal in profile shape, and the depth of the treated region may be related to the width of the frozen region. In embodiments, monitoring lateral growth of the frozen region over time is used to determine the depth of the frozen region, which in turn is used to determine the length of treatment. In embodiments, multiple transducers are mounted on the probe shaft so as to interrogate tissues at fixed lateral distances from the ablation member, for example at 5 mm, 10 mm, and 15 mm from the member. In embodiments, a single transducer may slide along a recessed path in the shaft (similar to as shown in FIG. 23) so as to interrogate tissues at various distances from the ablation member. In embodiments, a single transducer may be used at a fixed distance.

Figure 27A:
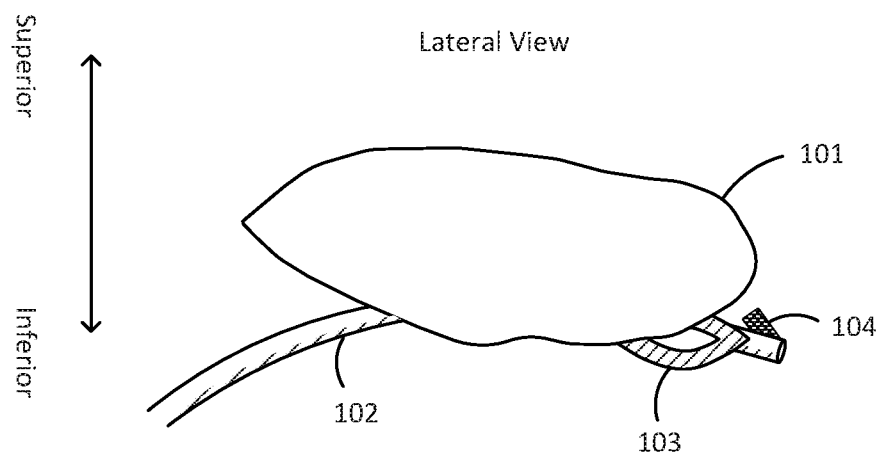
FIGS. 27A-C show an embodiments of an integrated probe for monitoring ice-ball formation.
Figure 27B:
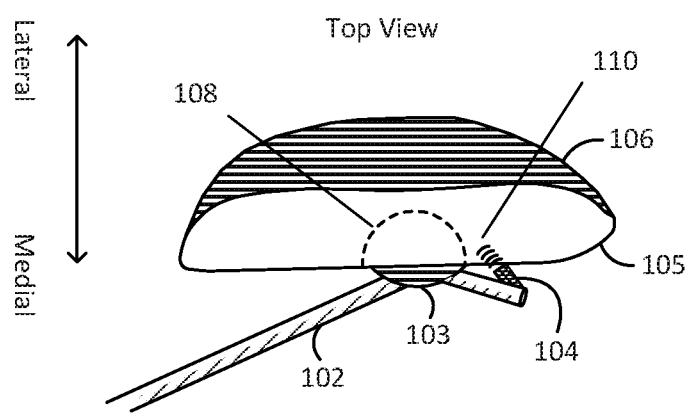
Figure 27C:
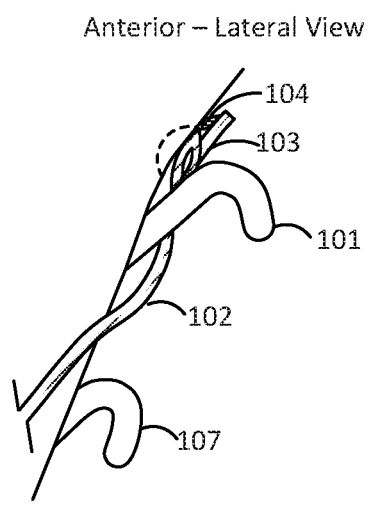

In embodiments the depth of the frozen region of tissue is measured directly. Since acoustic shadowing in the treated region may prevent straight-on measurements of ice-ball penetration, an oblique interrogation approach is used. An example embodiment utilizing oblique measurement of treatment depth is depicted in FIGS. 27A-C. As shown, a combined ablation and sensing probe 102 contains an ablation element 103 and an ultrasound transducer 104 located a distance $r_1$ distal to the ablation element. The transducer is angled an angle $\theta$ with respect to the longitudinal axis of the probe shaft and is aimed in the direction the ice ball is expected to form during cryo-ablation. During ablation, it is intended to create a frozen region 108 that will reach a distance r from the contact surface of the ablation element 103. Prior to treatment and in the early phases of treatment, the ultrasound transducer 104 scans tissue with the probe 102 positioned between the middle turbinate 101 and inferior turbinate 107, for example using A-mode imaging techniques, and receives a normal pattern of echo signals associated with soft tissue scanning. As the ice ball in the frozen region 108 in the tissue 105 grows, it enters the path of the ultrasound beam 110 and changes the received echo pattern. For example, the new echo pattern may be characterized by a hyperechoic area at the boundary of the ice ball followed by hypoechoic regions associated with acoustic shadowing. An advantage of the distal location of the ultrasound sensor on the probe is that it allows for an interrogation path that originates posterior to the middle turbinate 101, which may limit or eliminate echo interference associated with the bony prominence 106. In embodiments, the ultrasound sensor may be located more proximal on the probe shaft than the ablation element.

In some embodiments the angle $\theta$ of the axis of the beam of the ultrasound transducer relative to the axis of the distal end of the probe shaft may be adjustable by the user. When a desired depth of the ablation region (r) is known, the geometric tangent can be utilized to calculate the angle $\theta$ for the transducer given that $r_1$ is fixed. The transducer angle can be adjusted using dials, knobs, buttons, with a low-power motor/robotic control, or using other methods. In embodiments, the angle $\theta$ is fixed, but the distance $r_1$ is adjustable. In embodiments, both $\theta$ and $r_1$ are fixed.

Ultrasound may further be used to actively monitor tissue thickness changes during treatment. The ice crystal formation during cryo-ablation causes tissues to expand when treated. Though the amount of expansion is small, it is within the measurable resolution of ultrasound imaging techniques. After tissue has expanded a certain amount, for example a certain percentage of its baseline thickness (for example, 20%) or to a certain pre-calculated degree (for example, 1 mm), the detected expansion is used as an indication that the treatment is sufficient and that the procedure may end. In embodiments, A-mode or M-mode ultrasound techniques may be used to assess this expansion in real time, for example by determining changes in the thickness of mucosal tissue using techniques described previously in this disclosure. Though acoustic shadowing may confound assessment of tissue thickness directly in the treated region, expansion in immediately adjacent regions may be informative for guiding treatment.

Ultrasound measurements may be taken post treatment to detect changes in tissue properties associated with tissue thawing. These measurements may be used to determine when the device can be safely removed. For example, changes that were measured during treatment, such as alterations in echogenicity, thickness, or other characteristics, may begin to reverse themselves during thawing and approach baseline values. In a treatment paradigm that includes multiple cycles, these measurements may also be used to determine when the next freezing cycle should begin.

Ultrasound measurements may be taken post treatment to detect changes in tissue characteristics associated with cryo-ablation injury. For example, tissue injury may be associated with changes in density or changes in elasticity that are measurable using ultrasound. These measurements may be used to verify that target tissue has been treated.

Before, during, or post-treatment, M-mode ultrasound measurements may be acquired to assess tissues and/or changes in tissues resulting from ablation treatment. M-mode (motion mode) imaging acquires successive scans along the same region of interrogation (i.e. successive A-mode imaging lines) and as such can record how structures move toward or away from the transducer over time. At baseline, tissues may be detected to move differently than when frozen, and treated and subsequently thawed tissues may be detected to move differently than either frozen tissues or untreated tissues. As such, M-mode techniques may be used for assessing treatments in both the short- and longer-terms following treatment.

In embodiments, M-mode imaging is used to track naturally occurring tissue movements, for example physiological motion associated with the pulsation of arterial blood vessels. In embodiments, M-mode may be used to track tissue motion that occurs in response to an external stimulation, for example a pulse of acoustic radiation force emitted from the transducer or the application of a vibrating piston oscillator.

In embodiments, advanced processing techniques such as speckle tracking algorithms may be applied to M-Mode data to extract quantitative information from the scan, for example information about the exact degree of longitudinal tissue movement.

Figure 28A:
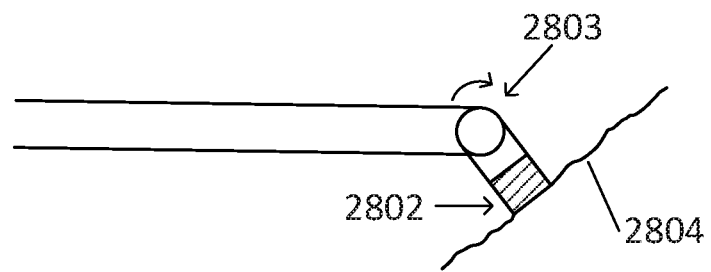
FIGS. 28A and 28B show an ultrasound transducer mounted on single axis joint to facilitate for orthogonal alignment with tissue surface.
Figure 28B:
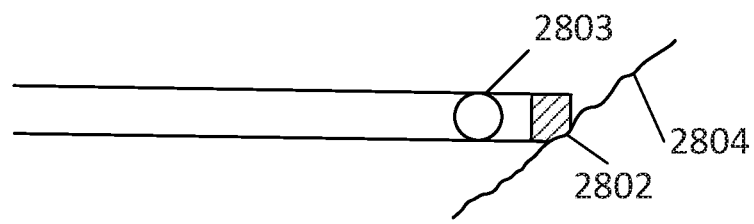
Figure 28C:
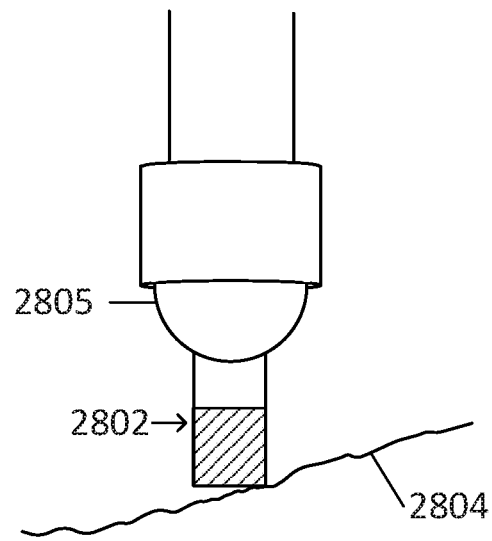
FIGS. 28C and 28D show an ultrasound transducer mounted on ball joint to facilitate for orthogonal alignment with tissue surface.
Figure 28D:
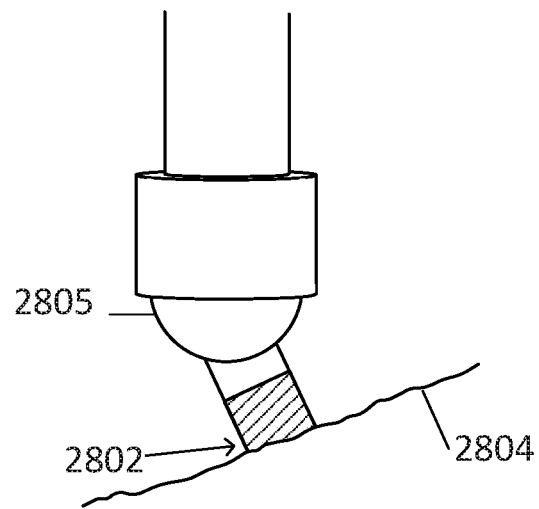
Figure 29:
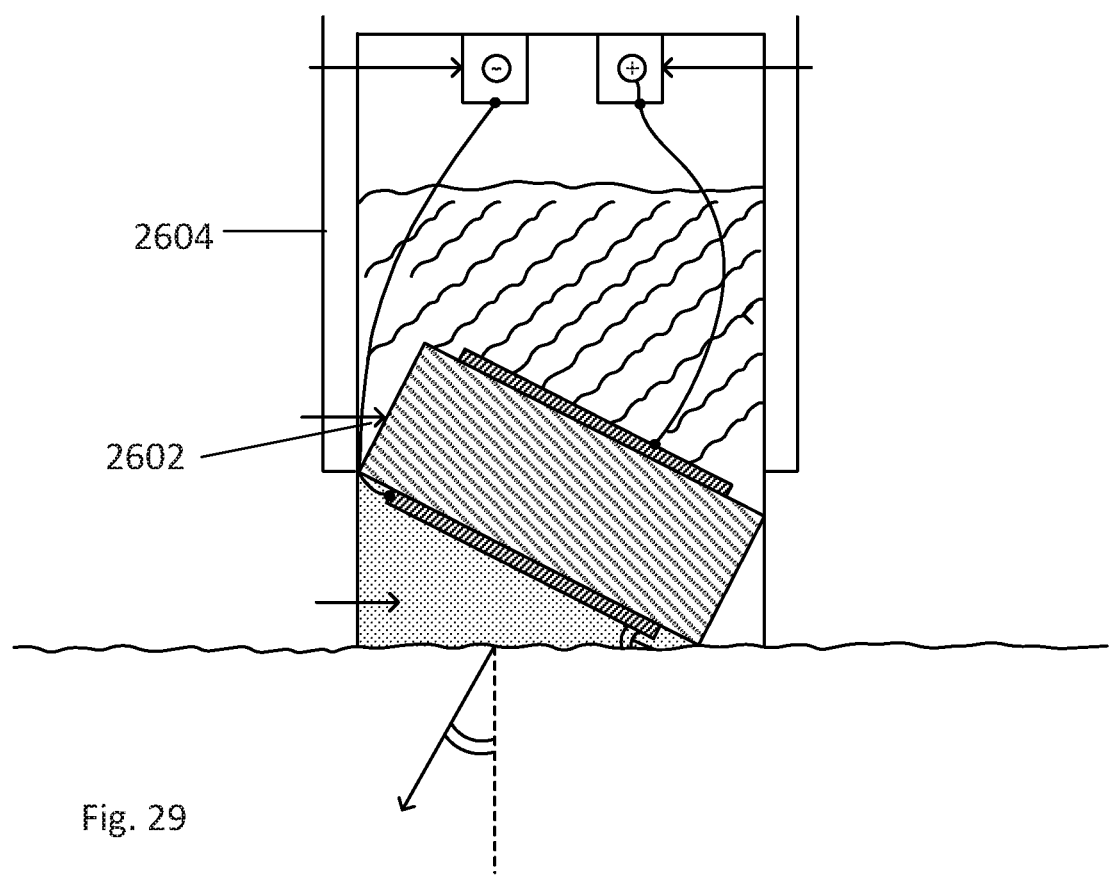
FIG. 29 shows a self-aligning ultrasound transducer.

In embodiments, ultrasound transducers housing may be attached to a probe through a joint capable of flexing or rotating in one or more directions. When the transducer housing is brought into contact at an angle other than 90°, the uneven pressure or force along the interface causes the housing to passively orient itself such that the housing and tissue surfaces are closer to parallel. FIGS. 28A and 28B show an ultrasound transducer 2802 mounted on single axis joint 2803 to facilitate for orthogonal alignment with tissue surface 2804. FIGS. 28C and 28D show an ultrasound transducer 2802 mounted on ball joint 2805 to facilitate for orthogonal alignment with tissue surface 2804. To better achieve a desired angle, the ultrasound transducer may be housed such that the axis of the transducer and of the housing are at a fixed angle between 0 and 90° with each other. When the surface of the housing is parallel to the tissue surface, the axis of the transducer is at roughly the same angle to the tissue as with the housing surface. This concept is illustrated in FIG. 29. FIG. 29 shows an ultrasound transducer 2902 mounted in housing 2904 at a desired angle with the surface of the housing in contact with tissue. When the housing surface is parallel to and in contact with the tissue surface, the ultrasound beam will be at a desired angle to the tissue surface. The housing is constructed such that the material between the transducer and tissue has an acoustic impedance appropriate to maximize ultrasonic energy transmission. In this way the transmitted ultrasound signal can be oriented to provide an increased accuracy related to Doppler measurements being made for vessels that run parallel or closely parallel to the tissue surface.

Figure 30:
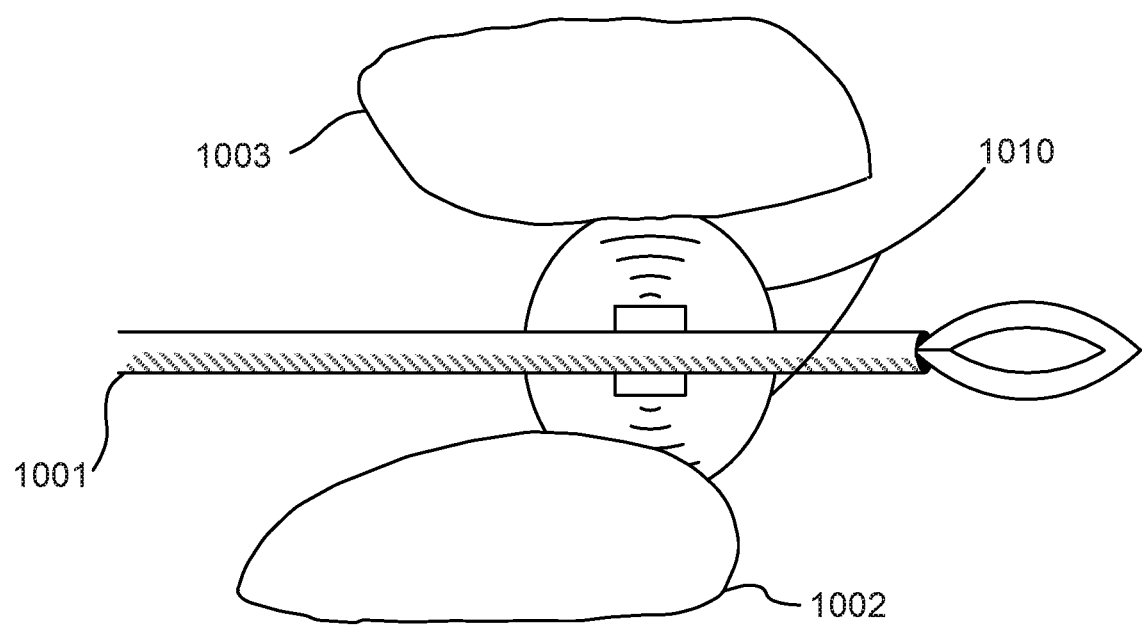
FIG. 30 shows an embodiment of a combined ablation and sensing probe with an acoustic coupling balloon.
Figure 31A:
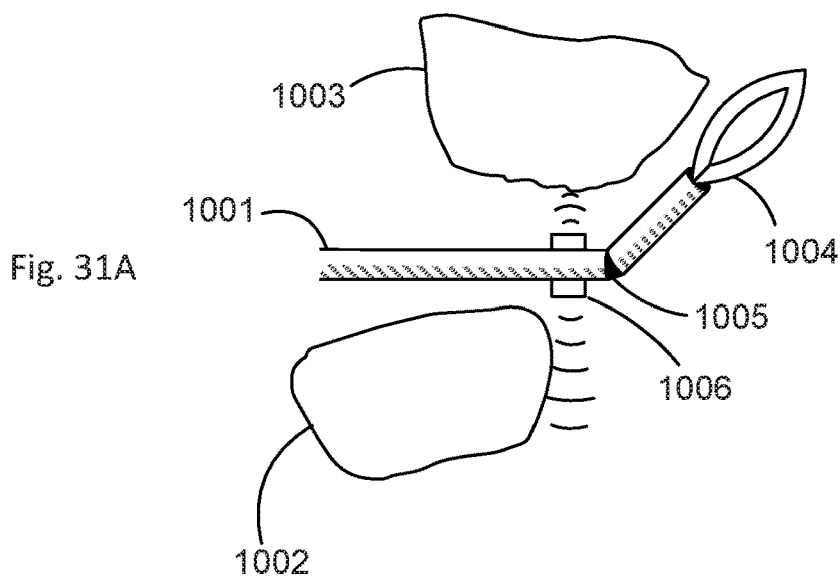
FIGS. 31A-C show embodiments that utilize the turbinates to guide placement of an ablation probe in a tissue region.
Figure 31B:
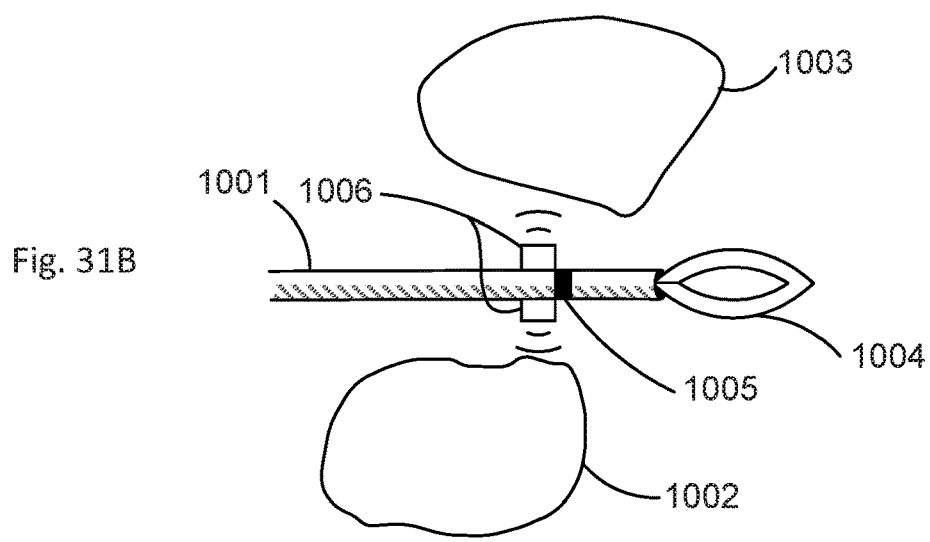
Figure 31C:
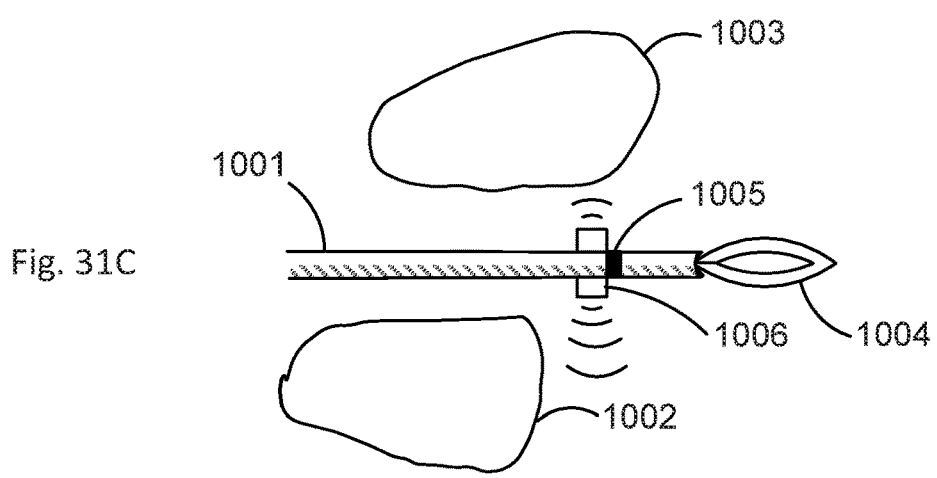

In embodiments, sensors on the shaft of a probe are used to aid with probe positioning by detecting and using the turbinates within the nasal cavity as guiding landmarks. In embodiments, the desired location for cryo-ablation treatment is the posterior ⅓ of the middle meatus, which may be identified generally by the relative position of the turbinates. More specifically, the inferior and middle turbinate may serve as landmarks used to locate the desired region for treatment or narrow the search region for the desired region of treatment. The inferior and middle turbinate can be located within the nasal cavity using endoscopic guidance or other methods, so a location technique that uses these features as navigation aids is simple, convenient, and allow for shorter procedure time. In an embodiment, a probe contains sensors which measure the relative position of a probe to the middle and inferior turbinate. The probe may be an ultrasound probe or a combined ablation/ultrasound probe, as disclosed above. The sensors may be acoustic, optical, electromagnetic, or mechanical in nature. For example, optical (ex. laser) or more general electromagnetic (ex. radar, infrared) sensors may be mounted to a probe shaft and measure distance from the shaft to a reflective surface such as the turbinates using time of flight measurements. In embodiments, ultrasound sensors may be used in conjunction with coupling mechanisms that allow the signal to acoustically couple to the turbinate wall. For example, the ultrasound sensor may be encased in an inflatable coupling balloon that is filled with gel, water, or another coupling substance that expands outward from the shaft and makes contact with turbinate walls. An example of an embodiment using a coupling balloon is shown in FIG. 30, with the coupling balloon 1010 serving as the mechanism for acoustically coupling ultrasound energy back and forth from the sensor and turbinates. Anatomy in the figure may not be to scale and is provided as a visualization aid only. FIG. 30 illustrates a combined ablation and sensing probe that utilizes acoustic coupling balloons. FIGS. 31A-C show embodiments that utilize the turbinates to guide placement of an ablation probe in a tissue region. The figures show the use of a non-ultrasound sensor, however in embodiments ultrasound sensors may be in place of or in addition to the sensors shown. Anatomical features depicted in the figure are not drawn to scale and may not be precisely co-located, and are included only as a contextual visual aid. As shown in FIG. 31A, a combined sensing and ablation probe 1001 is located in the nasal cavity in the general region between the inferior turbinate 1002 and middle turbinate 1003. In embodiments, the probe contains a joint 1005, for example a single-axis joint or a ball joint, that allows the distal end of the probe containing the ablation member 1004 to articulate with respect to the proximal end of the shaft. The probe contains sensors 1006 on the superior and inferior aspects of the probe for interrogating the middle and inferior turbinates, respectively. In embodiments, the sensors only seek to establish that the turbinates are present within the path of the sensor signals, or alternatively are present within a certain distance d of the sensor. As an illustrative example, the sensing protocol may be binary in nature and seek to determine only if a turbinate is located within 2 mm of the shaft, illuminating an LED if this condition is true. In embodiments, the sensors use time of flight or other techniques to measure the distance to each turbinate. Some embodiments may utilize additional sensors in additional locations, for example a sensor on the lateral aspect of the probe shaft for interrogating the lateral nasal cavity wall. As shown in FIG. 31A, the probe is situated in the nasal cavity such that the sensors on the probe shaft are located within the portion of the middle meatus bounded superiorly and inferiorly by the turbinates. As such signals produced by the sensors interact with the turbinates and inform the operator that it may be desirable to advance the probe more posteriorly prior to initiating treatment. As shown in FIG. 31B, the probe is advanced such that the sensor on the inferior side of the shaft is beyond the proximal boundary of the inferior turbinate, and as such the sensor signal is changed in such a way that the operator may determine that this anatomical landmark has been completely traversed. For example, the sensor may determine the distance to the closest reflective tissue is beyond a distance d that indicates the presence of the inferior turbinate. Given this location information, the probe may be determined to be in the proper position for ablation, or it may be determined how to further adjust the probe position based upon this anatomical landmark to prepare the probe to be in the proper position for ablation.

In embodiments, once the probe has advanced so as to be beyond the posterior boundary of one or both turbinates, the distal end of the probe may be articulated about the joint 1005 in order to better position the ablation member in the desired region of interest. In embodiments, the probe angle can be selectively changed, for example in one degree increments over a range of 0 to 30 degrees, by adjusting a dial located on the end of the device proximate to the handle. In embodiments, the probe angle may shift between two or more pre-determined available angles via the use of a dial or switch. An illustration of an embodiment with a variable probe angle is shown in FIG. 31C.

In embodiments, guiderail type sensors may contact the surface of the inferior and middle turbinates directly to aid with positioning of the ablation element in the region of interest. The guiderails are comprised of a spring-based or otherwise expandable/compressible rod topped by a sphere or another suitable structure that can glide smoothly along tissues while maintaining contact. As shown in FIG. 32A, when deployed guiderails 1008 emanate from the superior and inferior aspects of a probe and maintain contact with the turbinates as the probe traverses the nasal cavity in the region of the middle meatus. As an aspect of the probe becomes closer to the corresponding turbinate, force is exerted on the corresponding sphere and the corresponding guiderail is compressed, as shown in FIG. 32B. In embodiment, instead of being compressed the guiderail may be bent or shifted to a more acute angle. As an aspect of the probe moves away from the turbinate, or the probe traverses past the posterior boundary of a turbinate, the corresponding guiderail expands in length or is straightened and/or angled more normal to the probe surface. Sensors in the device measure guiderail position and can determine the presence of the turbinates, and in embodiments the distance to the turbinates. This information is used to guide the probe to the desired region for ablation. In embodiments, the guiderails may be collapsible into the body of the probe shaft so as not to increase the width of the shaft when not in use. This may allow the probe to maintain optimal maneuverability. FIG. 32C shows an embodiment including collapsible guiderails where a guiderail 1008 containing a spring-based body 1009 may collapse into a recessed region of the probe shaft 1007.

Sensors may be placed on or around ultrasound transducers to provide feedback to the user concerning the presence or quality of tissue contact. Sensors may include force sensors for detecting contact force between the probe and tissue surface. Sensors may include electrical impedance sensor/electrodes which can determine contact through electrical conductivity. If a sensor measures a very high impedance (similar to an "open circuit" condition), it will indicate the contact isn't be made effectively with tissue. If impedance is higher than expected, for example 2000 Ohms or higher, that may suggest that only partial contact is being made. In embodiments, different impedance values, for example 500 Ohms or 5000 Ohms, may be indicative of partial contact. If impedance is within the expected range for contact with mucosal tissues, for example 500 Ohms or less, it may be inferred that the sensor is making quality contact with the tissue. Sensors may also include non-contact sensors, such as light sensors or magnetic sensors that do not have to contact the tissue directly to function. In embodiments, light-based distance sensors are positioned both proximal and distal to an ultrasound transducer mounted on a probe. Each light sensor calculates the distance from the sensor to the mucosal tissue wall. To facilitate guiding the transducer face into quality contact with the mucosal wall, the distances measured as well as the difference in distances measured by the two sensors may be used to inform the operator how to best manipulate the position of the probe in order to establish quality transducer contact. In embodiments, one sensor or more sensors may be utilized.

In embodiments, the same transducer or transducers may be used alternately in different ultrasound modes. For example, a transducer may be configured to run in either Doppler or A-mode, and may be switched between modes based on the target tissue measurement. For example an ultrasound transducer may first be used to locate a blood vessel with a Doppler scan, as described above, and then may be used to detect a bony landmark with an A-mode scan. Further for example, the Doppler scan may be used to locate the SPA prior to treatment to determine a target treatment site, and then during treatment the same ultrasound transducer may be used with an A-mode scan to monitor tissue thickness or reflection changes associated with freezing, as described above. Further, after switching to an A-mode scan, the ultrasound transducer may then be switched back to a Doppler scan to monitor flow through the SPA. In another example, an ultrasound transducer may be used in A-mode prior to treatment to locate the sphenopalatine foramen or the transition between palatine and sphenoid bones which are landmarks by which the SPA can be located. Then, while cryo-ablation treatment is being performed a Doppler mode scan is used to monitor flow through the SPA. As noted above, in embodiments the angle of the ultrasound transducer relative to the probe shaft may be adjustable, and may be adjusted while in use. As noted above, the ideal angle of a transducer with respect to tissue may differ between A-mode and Doppler scan and in embodiments that switch ultrasound scan modes, the angle of transducer with respect to tissue may be adjusted back and forth between the ideals for each depending upon which mode is in use.

Embodiments in this disclosure may have been described as using ultrasound sensors, light-based sensors, or mechanical sensors. However, other types of imaging or sensing modalities may be implemented. For example, IR sensors, thermal sensors, thermal strain imaging, and photoacoustic imaging are all mechanisms that allow for evaluation of various characteristics of the nasal cavity anatomy, and as such aid in probe guidance as well in treatment planning and/or monitoring. In embodiments, a probe may include an array of microphones configured to detect audible blood flow. In embodiments, a probe may include an array of pressure sensors configured to assess probe and tissue contact as well as detect pulsations from arterial blood flow.

In embodiments, when the location of an anatomical features, for example the SPA, is located, one of the ultrasound probe, integrated probe, or a separate implement may be used to deposit surgical ink indicating the location of the SPA or a target ablation location based on the location of the SPA. With this approach, it may be visually confirmed that the ablation member is correctly positioned prior to commencing the ablation procedure. In embodiments SPA locations are marked visually with respect to visible landmarks. In embodiments the SPA locations are marked using 3D magnetic tracking systems which include surgical tracking systems which generate magnetic fields which encompass the surgical field and utilize measured interactions between those fields and active or passive magnetic markers on surgical tools to track the tool's location and orientation in the surgical field and to register those locations with respect to the patient anatomy.

Figure 35:
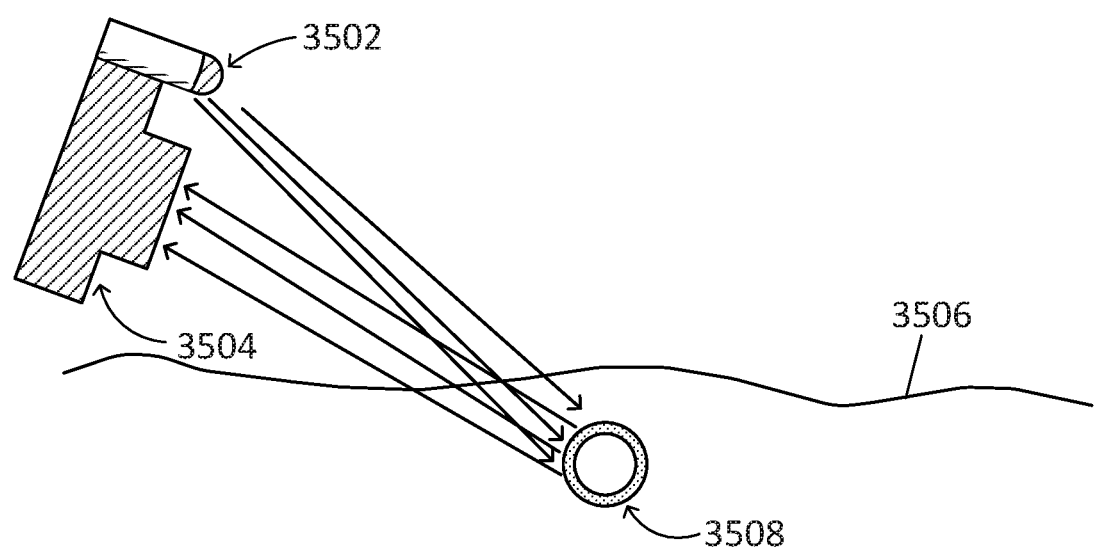
FIG. 35 shows an embodiment that illuminates tissue using IR light.
Figure 36:
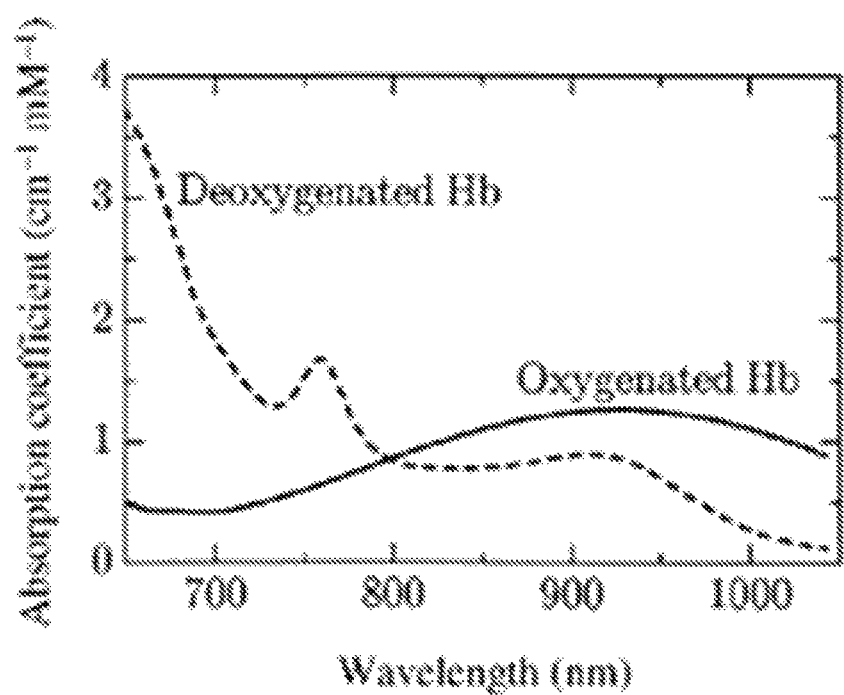
FIG. 36 shows absorption coefficients for different wavelengths.

In embodiments, the location of the SPA may be located by the processing unit using the optical (particularly absorptive, transmissive and reflective) properties of tissue with regard to infrared light or visible light. Different tissues absorb, reflect, and transmit different frequencies of light to varying degrees. For example, oxygenated and deoxygenated blood differentially absorb and transmit IR (wavelengths ranging from 700-1M nm) and near IR, or nIR (wavelengths ranging from 650-1350 nm) light, as shown in FIG. 35. Using these properties, the processing unit can differentiate arteries carry oxygenated blood from other vessels and tissues in the body based on IR absorption and reflection. In embodiments, a probe may include a light source and detector and an operator may place the probe within a nasal cavity and direct IR light or visible light into the tissue and the processing unit measures the reflected light spectra. The light source and reflector may be placed at angles to each other and a fraction of transmitted energy may be measured by the processing unit. By introducing visible light into the tissue at an angle relative to the observer (endoscope or camera) the tissues having a higher visible light transmission coefficient may appear more translucent while tissue having a higher absorptive or reflective coefficient may appear darker. In this way the large vessels may be visually differentiated from surrounding tissues and located by the operator or processing unit.

Figure 33A:
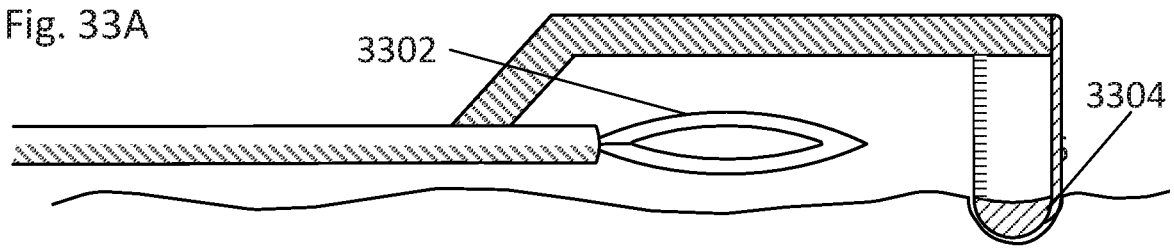
FIG. 33A shows an embodiment with an ablation member and a light sensing unit.
Figure 33B:
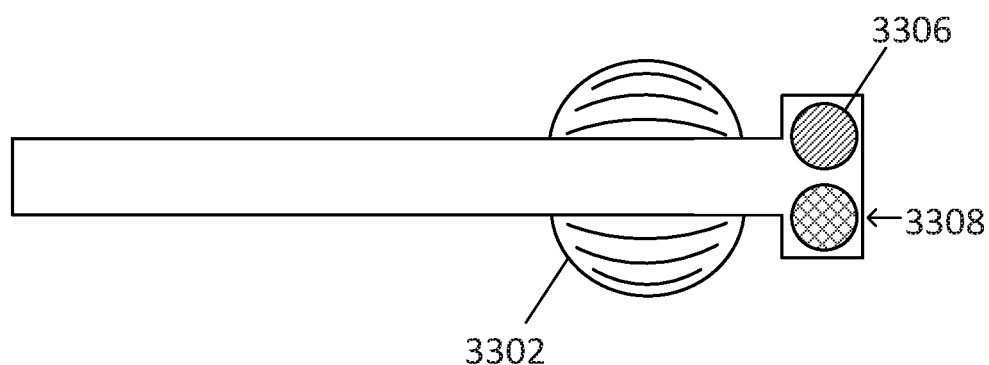
FIG. 33B shows an embodiment with an ablation member and a light sensing unit.
Figure 33C:
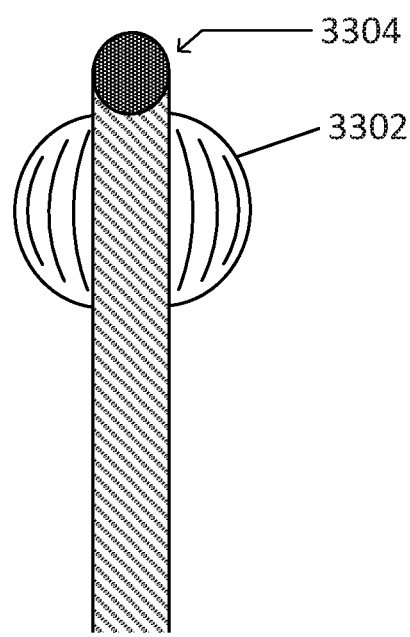
FIG. 33C shows an embodiment with an ablation member and a light sensing unit.

In embodiments, a probe may include an ablation member 3302 and a light sensing unit 3304, as shown in FIGS. 33A-C. The light sensing unit includes light source 3306 and light detector 3308 adjacent to each other. The light source may direct IR light or visible light into the tissue and the processing unit measures the reflected light spectra. The processing unit analyzes the spectra to different light reflected from arteries compared to light reflected from other tissues. Based on this differentiation, the processing unit may determine the location of the SPA. As discussed above, integrated probes including an element to detect SPA location and an ablation member, may be used to locate the SPA in real time and be used orient the integrated probe relative to the SPA at an ablation target, and then ablating the ablation target to ablate the PNN to treat rhinitis.

Figure 34:
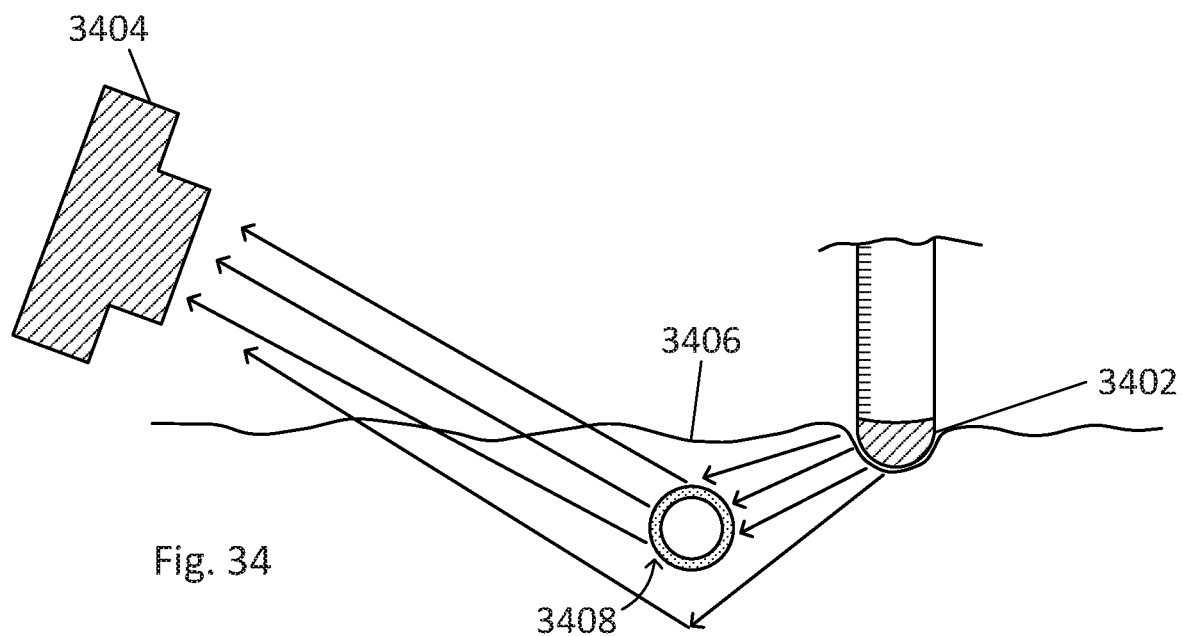
FIG. 34 shows an embodiment with a probe with a light source and a measuring unit to measure the transmitted light spectra through the tissue.

In embodiments, a probe may include a light source configured to be positioned away from or behind the tissue and a measuring unit located to measure the transmitted light spectra trough the tissue, as shown in FIG. 34. The anatomy of the nasal cavity is not conducive to placing the light source and reflector opposite each other orthogonal to the tissue surface 3406 with the tissue positioned between them, therefore as shown the light source 3402 and detector (IR camera 3404) may be placed at angles to each other and a fraction of transmitted energy from the blood vessel 3408 may be measured. As shown in FIG. 34, the light source 3402 may be on an separate probe from the receiver, which may be an endoscope or IR camera 3404.

In embodiments, a probe may illuminate the tissue using IR light 3502 and view the tissue 3506, including a blood vessel 3508, reflecting the emitted light using a digital camera 3504 capable of detecting IR wavelengths, as shown in FIG. 35.

In embodiments, to improve the coupling of energy between the ultrasound probe and the tissue being interrogated the ultrasound probe may include an internal gel delivery lumen, wherein the gel is delivered proximate to the ultrasound unit in order to improve coupling between the tissue and ultrasound unit. In embodiments, other methods and devices may be used to improve the coupling of ultrasound energy to tissue within the nasal cavity. For example, in embodiments, an ultrasound transducer may be disposed within a balloon or sack containing a gel, water bath, or other suitable coupling agent and may be filled prior to imaging. During use, the coupling balloon is located between the ultrasound transducer and the nasal tissue, and serves as an acoustic impedance matching zone that allows energy to flow more efficiently into tissues. This is useful because it allows for a transducer to not be in direct contact, or even in the immediate proximity of, tissues it is intended to interrogate with ultrasound. In embodiments, the coupling balloon may be filled and drained and re-filled, as the ultrasound probe may be easier to navigate in and out, and through the nasal cavity while it is in a smaller collapsed geometry with the balloon drained. In embodiments, the coupling balloon is filled a certain amount, for example 40% or 70% of maximum capacity. In embodiments, the degree of balloon filling is automatically governed by the device, for example the balloon may cease filling in response to an event such as detecting that the exterior of the balloon initiating contact with the nasal cavity wall. In embodiments, the coupling balloon may fill an entire portion of the nasal cavity and the transducer with or without ablation element can move freely inside the filled cavity to identify key locations of the nasal cavity. The coupling balloon may be used as an anchor device and allow energy to flow more efficiently into the tissue.

In embodiments, a system may include a navigation system which detects the location of portions of the ultrasound probe in a coordinate system and maps the detected locations of the anatomical features, such as the SPA and/or other blood vessels. The mapping may be used to position an ablation member at an ablation target site to ablate the PNN. For example, a mapping system identifies the path of the SPA which identifies the proximity of the nerves and the ablation probe is placed just adjacent to the SPA to allow ablation of the surrounding area without ablating directly on top of the large blood vessel.

In embodiments the sensing probe is a compliant volume filling member similar but not limited to a urethane balloon. On the outer surface of the probe, ultrasound transducers are affixed or surround the surface confined in an expandable net. The sensing probe is attached to a malleable to rigid shaft that allows the probe to be advanced to the posterior side of the nasal cavity while allowing the user to maneuver the probe from outside the nasal cavity. Once the sensing probe is in place, the probe is expanded so the probe conforms to the anatomy and presses the transducers, or at least one of the transducers, against the lateral wall. Once transducers are touching the wall, they are utilized to generate an image of the blood vessels, for example an A-Mode, B-Mode, or M-Mode image, in this area defining a target region on the display of the console in relationship to a visible anatomical landmark. Once the target region is defined, the sensing probe is collapsed and removed from the nasal cavity. The ablation probe will then be advanced to the target region using the aid of the blood vessel image defined by the sensing probe. In embodiments, this is accomplished by recognizing that the vessel on the image appears to be a certain distance d from a bony prominence which serves as a landmark, and knowing the target treatment region is for example approximately at the midpoint of this span (i.e. a distance of d/2 from landmark), and adjusting the position of the ablation probe accordingly. Once in place the ablation will be activated.

The teachings of the technology provided herein can be applied to other systems including systems, methods and devices disclosed in the applications incorporated by reference. The elements and acts of the various examples described above and in the patents and applications incorporated by reference can be combined to provide further implementations of the technology. Some alternative implementations of the technology may include not only additional elements to those implementations noted above, but also may include fewer elements. Further any specific numbers noted herein are only examples; alternative implementations may employ differing values or ranges, and can accommodate various increments and gradients of values within and at the boundaries of such ranges. Furthermore, the described features, advantages, and characteristics of the present technology and the technology disclosed in the applications incorporated by reference may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments of the present technology.

What is claimed is:

1. A method for treating rhinitis of a patient, the method comprising:
providing a surgical probe comprising an elongated probe shaft with a proximal end and a distal end, a handle coupled to the proximal end, and an ultrasound transducer and a cryo-ablation element integrated into the probe shaft, the cryo-ablation element disposed proximally on the probe shaft relative to the ultrasound transducer, the probe shaft including an articulation joint disposed between the cryo-ablation element and the ultrasound transducer, wherein the ultrasound transducer emits an ultrasound beam at an angle that is adjustable relative to the cryo-ablation element by bending the probe shaft at the articulation joint;
adjusting the angle of the ultrasound beam to an adjusted angle relative to the cryo-ablation element;
advancing the surgical probe into a nasal cavity of a patient;
determining, with a processing unit, a location of a target treatment site within the nasal cavity with the ultrasound beam of the ultrasound transducer;
positioning the cryo-ablation element at the location of the target treatment site;
operating the cryo-ablation element to cause cryogenic ablation at the target treatment site in order to ablate at least one nasal nerve to reduce at least one symptom of rhinitis; and
monitoring, with the processing unit, the cryogenic ablation with the ultrasound transducer with the ultrasound beam at the adjusted angle.

2. The method of claim 1, wherein determining the location of the target treatment site comprises detecting relative thicknesses of mucosal tissue in the nasal cavity with the ultrasound transducer to identify an anatomical landmark correlated to the location of the target treatment site.

3. The method of claim 1, wherein determining the location of the target treatment site comprises detecting relative thicknesses of a palatine or sphenoid bone in the nasal cavity with the ultrasound transducer to identify an anatomical landmark correlated to the location of the target treatment site.

4. The method of claim 1, wherein determining the location of the target treatment site comprises detecting a relative boundary or transition between two bones in the nasal cavity or between a bone and cartilage in the nasal cavity with the ultrasound transducer to identify an anatomical landmark correlated to the location of the target treatment site.

5. The method of claim 4, wherein the transition comprises 0.5-1 mm of cartilage adjacent to 1-3 mm of bone used to identify a perpendicular plate of a palatine bone.

6. The method of claim 1,
wherein a distance between the cryo-ablation element and the ultrasound transducer corresponds to a distance between an anatomical feature detectable with the ultrasound transducer and the at least one nasal nerve,
wherein determining the location of the target treatment site comprises locating the anatomical feature with the ultrasound transducer, and
wherein monitoring the cryogenic ablation with the ultrasound transducer includes detecting a signal indicating that the ultrasound transducer is proximate to the anatomical feature.

7. The method of claim 6, wherein the anatomical feature is a blood vessel.

8. The method of claim 1, wherein advancing the surgical probe into the nasal cavity comprises determining that the surgical probe is advancing through a middle meatus by detecting a middle turbinate in the nasal cavity with the ultrasound transducer.

9. The method of claim 1, wherein the surgical probe further comprises a light emitting element coupled to the probe shaft, and wherein when the location of the target treatment site is determined the light emitting element emits a visual indication within the nasal cavity.

10. The method of claim 1, wherein the surgical probe further comprises a haptic feedback element coupled to the handle, and wherein when the location of the target treatment site is determined the haptic feedback element emits a haptic indication.

11. The method of claim 1, wherein the cryo-ablation element comprises an expandable structure, and
wherein cryogenically ablating the target treatment site comprises inflating the expandable structure through evaporation of a cryogenic fluid within the expandable structure.

12. The method of claim 1, wherein monitoring the cryogenic ablation with the ultrasound transducer includes monitoring a size of an ice ball formed while cryogenically ablating the target treatment site,
wherein the ultrasound beam intersects tissue in the nasal cavity where the ice ball forms.

13. The method of claim 12, further comprising terminating cryogenic ablation when the size of the ice ball reaches a predetermined size range.

14. The method of claim 1, wherein the cryo-ablation element is slidably coupled to the probe shaft, wherein after the location of the target treatment site is determined the cryo-ablation element is advanced into the nasal cavity by sliding the cryo-ablation element along the probe shaft toward the distal end of the probe shaft to the target treatment site.

15. A method for treating rhinitis of a patient, the method comprising:
providing a surgical probe comprising an elongated probe shaft with a proximal end and a distal end, a handle coupled to the proximal end, an ultrasound transducer coupled at the distal end of the probe shaft, and a cryo-ablation element slidably coupled to the probe shaft and disposed on the probe shaft proximally relative to the ultrasound transducer, wherein the ultrasound transducer emits an adjustable ultrasound beam at an angle that is adjustable relative to a longitudinal axis of the probe shaft;
adjusting the angle of the ultrasound beam to an adjusted angle relative to the longitudinal axis of the probe shaft;
advancing the surgical probe into a nasal cavity of a patient;
detecting, with a processing unit, an anatomical feature within the nasal cavity with the ultrasound beam of the ultrasound transducer in order to determine a location of a target treatment site;
advancing the cryo-ablation element slidably toward the distal end to the determined location of the target treatment site while the ultrasound transducer is positioned distally relative to the cryo-ablation element and proximate to the detected anatomical feature with the ultrasound beam at the adjusted angle, wherein a position of the ultrasound transducer is variable with respect to the cryo-ablation element; and cryogenically ablating the target treatment site, while the ultrasound transducer is positioned proximate to the detected anatomical feature with the ultrasound beam at the adjusted angle, in order to ablate at least one nasal nerve to reduce at least one symptom of rhinitis.

16. The method of claim 15, wherein the anatomical feature is a blood vessel, and wherein detecting the location of the anatomical feature comprises detecting a blood flow in the blood vessel.

17. The method of claim 16, wherein the blood vessel is the sphenopalatine artery or vein.

18. The method of claim 15, wherein the cryo-ablation element comprises an expandable structure, and
wherein cryogenically ablating the target treatment site comprises inflating the expandable structure through evaporation of a cryogenic fluid within the expandable structure.

19. The method of claim 18, wherein the expandable structure has a lumen, and wherein advancing the cryo-ablation element comprises sliding the probe shaft through the lumen.

20. The method of claim 15, wherein a distance between the detected anatomical feature and the location of the target treatment site corresponds to a distance between a sphenopalatine artery or vein and the at least one nasal nerve.

21. A method for evaluating a treatment procedure within a nasal cavity of a patient based on a tissue characteristic measured with ultrasound, the method comprising:
providing a surgical probe comprising an elongated probe shaft with a proximal end and a distal end, a handle coupled to the proximal end, and an ultrasound transducer and a cryo-ablation element integrated into the probe shaft, the cryo-ablation element disposed proximally on the probe shaft relative to the ultrasound transducer, the probe shaft including an articulation joint disposed between the cryo-ablation element and the ultrasound transducer, wherein the ultrasound transducer emits an ultrasound beam at an angle that is adjustable relative to the cryo-ablation element by bending the probe shaft at the articulation joint;
adjusting the angle of the ultrasound beam to an adjusted angle relative to the cryo-ablation element;
advancing the surgical probe into a nasal cavity of a patient;
evaluating, with a processing unit, a pre-treatment tissue characteristic with a first ultrasound scan of the nasal cavity with the ultrasound beam of the ultrasound transducer at the adjusted angle;
performing a treatment procedure within the nasal cavity with the cryo-ablation element;
evaluating, with the processing unit, a post-treatment tissue characteristic with a second ultrasound scan of the nasal cavity with the ultrasound beam of the ultrasound transducer at the adjusted angle; and
evaluating, with the processing unit, a change between the pre-treatment tissue characteristic and the post-treatment tissue characteristic to assess an effectiveness of the treatment procedure.

22. The method of claim 21, wherein performing the treatment procedure comprises cryogenically ablating at least one nasal nerve to reduce at least one symptom of rhinitis.

23. The method of claim 22, wherein the pre-treatment tissue characteristic and the post-treatment characteristic comprise mucosal tissue thickness, edema, or fluid content.

24. The method of claim 23, wherein evaluating the change between the pre-treatment tissue characteristic and the post-treatment tissue characteristic further comprises accounting for a contact force applied to a nasal cavity wall.

25. The method of claim 23, wherein the first and second ultrasound scans comprise echogenicity, elastography, or elasticity measurements of the mucosal tissue.

26. The method of claim 21, further comprising re-treating the nasal cavity in response to the evaluation of the change between pre-treatment tissue characteristic and the post-treatment tissue characteristic.

\* \* \* \* \*